US011608412B2

(12) United States Patent
Kaczmarek et al.

(10) Patent No.: US 11,608,412 B2
(45) Date of Patent: Mar. 21, 2023

(54) POLYMER-LIPIDS AND COMPOSITIONS

(71) Applicant: Massachusetts Institute of Technology, Cambridge, MA (US)

(72) Inventors: James C. Kaczmarek, Somerville, MA (US); Daniel Griffith Anderson, Framingham, MA (US); Luke Hyunsik Rhym, Cambridge, MA (US); Kevin John Kauffman, Somerville, MA (US); Asha Kumari Patel, Ilford (GB)

(73) Assignee: Massachusetts Institute of Technology, Cambridge, MA (US)

(*) Notice: Subject to any disclaimer, the term of this patent is extended or adjusted under 35 U.S.C. 154(b) by 557 days.

(21) Appl. No.: 16/663,585

(22) Filed: Oct. 25, 2019

(65) Prior Publication Data

US 2020/0172663 A1  Jun. 4, 2020

Related U.S. Application Data

(60) Provisional application No. 62/751,116, filed on Oct. 26, 2018.

(51) Int. Cl.
| | |
|---|---|
| *C08G 63/685* | (2006.01) |
| *A61K 47/59* | (2017.01) |
| *A61K 47/54* | (2017.01) |
| *A61K 47/28* | (2006.01) |
| *C08G 63/56* | (2006.01) |
| *A61K 31/7105* | (2006.01) |

(52) U.S. Cl.
CPC ............ *C08G 63/685* (2013.01); *A61K 47/28* (2013.01); *A61K 47/544* (2017.08); *A61K 47/593* (2017.08); *C08G 63/56* (2013.01); *A61K 31/7105* (2013.01)

(58) Field of Classification Search
CPC .... A61K 47/28; A61K 47/544; A61K 47/593; A61K 31/7105; A61K 9/0019; A61K 9/5146; C08L 79/02; C08G 63/56; C08G 63/685; C08G 73/024
See application file for complete search history.

(56) References Cited

U.S. PATENT DOCUMENTS

| | | |
|---|---|---|
| 2,759,913 A | 8/1956 | Hulse |
| 3,963,771 A | 6/1976 | Robson et al. |
| 4,224,365 A | 9/1980 | Ali-Zaidi |
| 4,348,511 A | 9/1982 | Haug |
| 5,180,424 A | 1/1993 | Hutter |
| 5,364,634 A | 11/1994 | Lew |
| 5,462,990 A | 10/1995 | Hubbell et al. |
| 5,525,357 A | 6/1996 | Keefer et al. |
| 5,573,934 A | 11/1996 | Hubbell et al. |
| 5,705,188 A | 1/1998 | Junichi et al. |
| 5,770,637 A | 6/1998 | Vanderlaan et al. |
| 5,858,746 A | 1/1999 | Hubbell et al. |
| 5,904,927 A | 5/1999 | Amiji |
| 5,962,520 A | 10/1999 | Smith et al. |
| 6,060,582 A | 5/2000 | Hubbell et al. |
| 6,444,725 B1 | 9/2002 | Trom et al. |
| 6,984,404 B1 | 1/2006 | Talton et al. |
| 6,998,115 B2 | 2/2006 | Langer et al. |
| 7,427,394 B2 | 9/2008 | Anderson et al. |
| 8,071,082 B2 | 12/2011 | Zugates et al. |
| RE43,612 E | 8/2012 | Anderson et al. |
| 8,287,849 B2 | 10/2012 | Langer et al. |
| 8,557,231 B2 | 10/2013 | Langer et al. |
| 8,562,966 B2 | 10/2013 | Zugates et al. |
| 8,748,551 B2 | 6/2014 | Puerta et al. |
| 8,808,681 B2 | 8/2014 | Anderson et al. |
| 9,101,666 B2 | 8/2015 | Langer et al. |
| 2001/0048940 A1 | 12/2001 | Tousignant et al. |
| 2002/0131951 A1 | 9/2002 | Langer et al. |
| 2004/0028694 A1 | 2/2004 | Young et al. |
| 2004/0071654 A1 | 4/2004 | Anderson et al. |
| 2004/0175328 A1 | 9/2004 | Sutton et al. |
| 2005/0059005 A1 | 3/2005 | Tuschl et al. |
| 2005/0122550 A1 | 6/2005 | Plewa et al. |
| 2005/0238716 A1 | 10/2005 | Verrijk et al. |
| 2005/0244504 A1 | 11/2005 | Little et al. |
| 2005/0265961 A1 | 12/2005 | Langer et al. |
| 2006/0062821 A1 | 3/2006 | Simhambhatla et al. |
| 2006/0105975 A1 | 5/2006 | Pendergrast et al. |
| 2007/0178126 A1 | 8/2007 | Angot et al. |
| 2008/0145338 A1 | 6/2008 | Anderson et al. |

(Continued)

FOREIGN PATENT DOCUMENTS

| | | |
|---|---|---|
| DE | 16 68 502 A1 | 9/1971 |
| DE | 25 20 814 A1 | 11/1976 |

(Continued)

OTHER PUBLICATIONS

Kaczmarek et al.; Angew. Chem. Int. Ed., 2016, vol. 55, No. 44, p. 13808-13182 and Supporting Information, p. 1-21.*
Bals et al., Innate immunity in the lung: how epithelial cells fight against respiratory pathogens. Eur Respir J. Feb. 2004;23(2):327-33.
Bantikassegn et al., Isolation of epithelial, endothelial, and immune cells from lungs of transgenic mice with oncogene-induced lung adenocarcinomas. Am J Respir Cell Mol Biol. Apr. 2015;52(4):409-17. doi: 10.1165/rcmb.2014-0312MA.
Blanco et al., Principles of nanoparticle design for overcoming biological barriers to drug delivery. Nat Biotechnol. Sep. 2015;33(9):941-51. doi:10.1038/nbt.3330.
Chen et al., Rapid discovery of potent siRNA-containing lipid nanoparticles enabled by controlled microfluidic formulation. J Am Chem Soc. Apr. 25, 2012;134(16):6948-51. doi: 10.1021/ja301621z. Epub Apr. 10, 2012.

(Continued)

*Primary Examiner* — Robert S Jones, Jr.
(74) *Attorney, Agent, or Firm* — Wolf, Greenfield & Sacks, P.C.

(57) ABSTRACT

The present disclosure relates to improvements in the selection and formulation of PBAE polymers using a design of experiment approach, in which statistical methods are used to limit possible experimental conditions. The present disclosure relates to improved PBAE polymers and formulations.

34 Claims, 26 Drawing Sheets

Specification includes a Sequence Listing.

(56) References Cited

U.S. PATENT DOCUMENTS

| | | | |
|---|---|---|---|
| 2008/0242626 A1* | 10/2008 | Zugates | A61K 47/34 |
| | | | 526/312 |
| 2010/0036084 A1 | 2/2010 | Langer et al. | |
| 2010/0196492 A1 | 8/2010 | Green et al. | |
| 2012/0065358 A1 | 3/2012 | Langer et al. | |
| 2012/0149630 A1 | 6/2012 | Zugates et al. | |
| 2012/0294944 A1* | 11/2012 | Emanuel | A61K 31/7088 |
| | | | 514/44 R |
| 2013/0302401 A1 | 11/2013 | Ma et al. | |
| 2014/0094399 A1 | 4/2014 | Langer et al. | |
| 2014/0271861 A1* | 9/2014 | Emanuel | A61K 9/70 |
| | | | 514/2.3 |
| 2015/0273071 A1 | 10/2015 | Green | |
| 2016/0022821 A1 | 1/2016 | Langer et al. | |
| 2017/0216455 A1 | 8/2017 | Wang et al. | |

FOREIGN PATENT DOCUMENTS

| | | |
|---|---|---|
| DE | 19626567 A1 | 1/1998 |
| EP | 0959092 A1 | 11/1999 |
| EP | 1489126 A1 | 12/2004 |
| JP | 52-045327 A | 4/1977 |
| JP | 08-092369 A | 4/1996 |
| JP | 2004-506000 T | 2/2004 |
| WO | WO 1998/016202 A2 | 4/1998 |
| WO | WO 2002/013767 A2 | 2/2002 |
| WO | WO 2002/031025 | 4/2002 |
| WO | WO 2002/031025 A2 | 4/2002 |
| WO | WO 2004/106411 | 12/2004 |
| WO | WO 2004/106411 A2 | 12/2004 |
| WO | WO 2008/011561 | 1/2008 |
| WO | WO 2008/011561 A2 | 1/2008 |
| WO | WO 2016/020374 A1 | 2/2016 |

OTHER PUBLICATIONS

Dong et al., Lipopeptide nanoparticles for potent and selective siRNA delivery in rodents and nonhuman primates. Proc Natl Acad Sci U S A. Mar. 18, 2014;111(11):3955-60. doi: 10.1073/pnas.1322937111. Epub Feb. 10, 2014. Erratum in: Proc Natl Acad Sci U S A. Apr. 15, 2014;111(15):5753.

Dowdy, Overcoming cellular barriers for RNA therapeutics. Nat Biotechnol. Mar. 2017;35(3):222-229. doi: 10.1038/nbt.3802. Epub Feb. 27, 2017.

Eltoukhy et al., Degradable terpolymers with alkyl side chains demonstrate enhanced gene delivery potency and nanoparticle stability. Adv Mater. Mar. 13, 2013;25(10):1487-93. doi:10.1002/adma.201204346. Epub Jan. 4, 2013.

Eltoukhy et al., Effect of molecular weight of amine end-modified poly(β-amino ester)s on gene delivery efficiency and toxicity. Biomaterials. May 2012;33(13):3594-603. doi:10.1016/j.biomaterials.2012.01.046. Epub Feb. 14, 2012.

Fenton et al., Bioinspired Alkenyl Amino Alcohol Ionizable Lipid Materials for Highly Potent In Vivo mRNA Delivery. Adv Mater. Apr. 20, 2016;28(15):2939-43. doi:10.1002/adma.201505822. Epub Feb. 18, 2016.

Green et al., The role of the endothelium in asthma and chronic obstructive pulmonary disease (COPD). Respir Res. Jan. 18, 2017;18(1):20. doi:10.1186/s12931-017-0505-1.

Grumelli et al., An immune basis for lung parenchymal destruction in chronic obstructive pulmonary disease and emphysema. PLoS Med. Oct. 2004;1(1):e8. Epub Oct. 19, 2004.

Guan et al., Nanotechnologies in delivery of mRNA therapeutics using nonviral vector-based delivery systems. Gene Ther. Mar. 2017;24(3):133-143. doi:10.1038/gt.2017.5. Epub Jan. 17, 2017.

Kaczmarek et al., Advances in the delivery of RNA therapeutics: from concept to clinical reality. Genome Med. Jun. 27, 2017;9(1):60. doi: 10.1186/s13073-017-0450-0.

Kanasty et al., Delivery materials for siRNA therapeutics. Nat Mater. Nov. 2013;12(11):967-77. doi: 10.1038/nmat3765.

Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.

Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.

Kim et al., Persistent activation of an innate immune response translates respiratory viral infection into chronic lung disease. Nat Med. Jun. 2008;14(6):633-40. doi:10.1038/nm1770. Epub May 18, 2008.

Leus et al., VCAM-1 specific PEGylated SAINT-based lipoplexes deliver siRNA to activated endothelium in vivo but do not attenuate target gene expression. Int J Pharm. Jul. 20, 2014;469(1):121-31. doi: 10.1016/j.ijpharm.2014.04.041. Epub Apr. 18, 2014.

Schrom et al., Translation of Angiotensin-Converting Enzyme 2 upon Liver- and Lung-Targeted Delivery of Optimized Chemically Modified mRNA. Mol Ther Nucleic Acids. Jun. 16, 2017;7:350-365. doi: 10.1016/j.omtn.2017.04.006. Epub Apr. 13, 2017.

Shmueli et al., Gene delivery nanoparticles specific for human microvasculature and macrovasculature. Nanomedicine. Oct. 2012;8(7):1200-7. doi: 10.1016/j.nano.2012.01.006. Epub Feb. 1, 2012.

Whitehead et al., In vitro-in vivo translation of lipid nanoparticles for hepatocellular siRNA delivery. ACS Nano. Aug. 28, 2012;6(8):6922-9. doi:10.1021/nn301922x. Epub Jul. 6, 2012.

Zugates et al., Rapid Optimization of Gene Delivery by Parallel End-modification of Poly(β-amino ester)s. Mol Ther. Jul. 2007;15(7):1306-1312. doi:10.1038/sj.mt.6300132. Epub Dec. 7, 2016.

International Search Report and Written Opinion for PCT/US2019/058064, dated Apr. 9, 2020.

International Preliminary Report on Patentability for PCT/US2019/058064, dated May 6, 2021.

Akinc et al., Measuring the pH environment of DNA delivered using nonviral vectors: implications for lysosomal trafficking. Biotechnol Bioeng. Jun. 5, 2002;78(5):503-8.

Akinc et al., Parallel synthesis and biophysical characterization of a degradable polymer library for gene delivery. J Am Chem Soc. May 7, 2003;125(18):5316-23.

Allison, The mode of action of immunological adjuvants. Dev Biol Stand. 1998;92:3-11.

Anderson et al., A polymer library approach to suicide gene therapy for cancer. Proc Natl Acad Sci USA. Nov. 9, 2004;101(45):16028-33. Epub Nov. 1, 2004.

Anderson et al., Biodegradation and biocompatibility of PLA and PLGA microspheres. Adv Drug Deliv Rev. Oct. 13, 1997;28(1):5-24.

Anderson et al., Nanoliter-scale synthesis of arrayed biomaterials and application to human embryonic stem cells. Nat Biotechnol. Jul. 2004;22(7):863-6. Epub Jun. 13, 2004.

Anderson et al., Semi-automated synthesis and screening of a large library of degradable cationic polymers for gene delivery. Angew Chem Int Ed Engl. Jul. 14, 2003;42(27):3153-8.

Anderson et al., Structure/property studies of polymeric gene delivery using a library of poly(beta-amino esters). Mol Ther. Mar. 2005;11(3):426-34.

Ando et al., PLGA microspheres containing plasmid DNA: preservation of supercoiled DNA via cryopreparation and carbohydrate stabilization. J Pharm Sci. Jan. 1999;88(1):126-30.

Angeloni et al., Liquid crystalline poly (ß-aminoester)s containing different mesogenic groups. Makromlekulare Chemie. 1985;186:977-97.

Anseth et al., In situ forming degradable networks and their application in tissue engineering and drug delivery. J Control Release. Jan. 17, 2002;78(1-3):199-209.

Anseth et al., New Directions in Photopolymerizable Biomaterials. Mrs Bull. 2002;27:130-136.

Anseth et al., Photopolymerizable degradable polyanhydrides with osteocompatibility. Nat Biotechnol. Feb. 1999;17(2):156-9.

Anseth et al., Polymeric Dental Composites: Properties and Reaction Behavior of Multimethacrylate Dental Restorations. Advances in Polymer Science. 1995;122:177-217.

(56) References Cited

OTHER PUBLICATIONS

Barbucci et al. Macroinorganics. 7. Property-Structure Relationships for Polymeric Bases Whose Monomeric Units Behave Independently towards Protonation. Macromolecules 1981;14:1203-09.
Barbucci et al., Protonation studies of multifunctional polymers with a poly(amido-amine) structure. Polymer. 1978;19:1329-34.
Barbucci et al., Thermodynamic ad 13C n.m.r. data on the protonation of polymeric bases whose repeating units behave independently towards protonation. Polymer. 1980;21:81-85.
Barrera et al., Synthesis and RGD Peptide Modification of a New Biodegradable Copolymer: Poly(lactic acid-co-lysine). J Am Chem Soc. 1993;115:11010-11.
Beebe et al., Microfluidic tectonics: a comprehensive construction platform for microfluidic systems. Proc Natl Acad Sci U S A. Dec. 5, 2000;97(25):13488-93.
Behr, Synthetic Gene-Transfer Vectors. Acc Chem Res. 1993;26:274-78.
Behr, The Proton Sponge: a Trick to Enter Cells the Viruses Did Not Exploit. Chimia. 1997;51:34-36.
Benns et al., pH-sensitive cationic polymer gene delivery vehicle: N-Ac-poly(L-histidine)-graft-poly(L-lysine) comb shaped polymer. Bioconjug Chem. Sep.-Oct. 2000;11(5):637-45.
Boussif et al., A versatile vector for gene and oligonucleotide transfer into cells in culture and in vivo: polyethylenimine. Proc Natl Acad Sci U S A. Aug. 1, 1995;92(16):7297-301.
Brazeau et al., In vitro myotoxicity of selected cationic macromolecules used in non-viral gene delivery. Pharm Res. May 1998;15(5):680-4.
Brocchini et al., A Combinatorial Approach for Polymer Designs. J Am Chem Soc. 1997;119:4553-54.
Brocchini, Combinatorial chemistry and biomedical polymer development. Adv Drug Deliv Rev. Dec. 3, 2001;53(1):123-30.
Bryant et al., Cytocompatibility of UV and visible light photoinitiating systems on cultured NIH/3T3 fibroblasts in vitro. J Biomater Sci Polym Ed. 2000;11(5):439-57.
Burdick et al., Photoencapsulation of osteoblasts in injectable RGD-modified PEG hydrogels for bone tissue engineering. Biomaterials. Nov. 2002;23(22):4315-23.
Burdick et al., Stimulation of neurite outgrowth by neurotrophins delivered from degradable hydrogels. Biomaterials. Jan. 2006;27(3):452-9. Epub Aug. 22, 2005.
Byloos et al., Phase Transitions of Alkanethiol Self-Assembled Monolayers at an Electrified Gold Surface. J Phys Chem B. 2001;105:5900-05.
Caminschi et al., Molecular cloning of F4/80-like-receptor, a seven-span membrane protein expressed differentially by dendritic cell and monocyte-macrophage subpopulations. J Immunol. Oct. 1, 2001;167(7):3570-6.
Capan et al., Preparation and characterization of poly (D,L-lactide-co-glycolide) microspheres for controlled release of poly(L-lysine) complexed plasmid DNA. Pharm Res. Apr. 1999;16(4):509-13.
Casimiro et al., Vaccine-induced immunity in baboons by using DNA and replication-incompetent adenovirus type 5 vectors expressing a human immunodeficiency virus type 1 gag gene. J Virol. Jul. 2003;77(13):7663-8.
Chan et al., Triplex DNA: fundamentals, advances, and potential applications for gene therapy. J Mol Med. Apr. 1997;75(4):267-82.
Cho et al., A proposed mechanism for the induction of cytotoxic T lymphocyte production by heat shock fusion proteins. Immunity. Mar. 2000;12(3):263-72.
Cho et al., Homeostasis-stimulated proliferation drives cotton T cells to differentiate directly into memory T cells. J Exp Med. Aug. 21, 2000;192(4):549-56.
Choksakulnimitr et al., In vitro cytotoxicity of macromolecules in different cell culture systems. J Control Rel. 1995;34:233-41.
Cotten et al., Receptor-mediated transport of DNA into eukaryotic cells. Methods Enzymol. 1993;217:618-44.
Crooke, Evaluating the mechanism of action of antiproliferative antisense drugs. Antisense Nucleic Acid Drug Dev. Apr. 2000;10(2):123-6; discussion 127.
Crooke, Molecular mechanisms of action of antisense drugs. Biochim Biophys Acta. Dec. 10, 1999;1489(1):31-44.
Crystal, Transfer of genes to humans: early lessons and obstacles to success. Science. Oct. 20, 1995;270(5235):404-10.
De Smedt et al., Cationic polymer based gene delivery systems. Pharm Res. Feb. 2000;17(2):113-26.
Demeneix et al., Chapter 14. The Proton Sponge: A Trick the Viruses Did Not Exploit. Artificial Self Assembly Systems for Gene Delivery (Felgner et al Eds). 1996:146-51.
Deshmukh et al., Liposome and polylysine mediated gene transfer. New J Chem. 1997;21:113-24.
Eddington et al., Flow control with hydrogels. Adv Drug Deliv Rev. Feb. 10, 2004;56(2):199-210.
Elisseeff et al., Transdermal photopolymerization for minimally invasive implantation. Proc Natl Acad Sci U S A. Mar. 16, 1999;96(6):3104-7.
Ferruti et al., A novel modification of poly(1-lysine) leading to a soluble cationic polymer with reduced toxicity and with potential as a transfection agent. Macromol Chem Phys 1998;199:2565-75.
Ferruti et al., Linear Amino Polymers: Synthesis, Protonation and Complex Formation. Advances in Polymer Sci. 1984;58:55-92.
Ferruti et al., Recent results on functional polymers and macromonomers of interest as biomaterials or for biomaterial modification. Biomaterials. Dec. 1994;15(15):1235-41.
Ferruti et al., Synthesis, characterisation and antitumour activity of platinum (II) complexes of novel functionalised poly(amido amine)s. Macromol Chem Phys. 1999;200:1644-54.
Ferruti et al., Synthesis, physico-chemical properties and biomedical applications of poly(amido-amine)s. Polymyer. 1985;26:1336-48.
Field et al., A simple predictive model for spherical indentation. J Mater Res. 1993;8(2):297-306.
Fire et al., Potent and specific genetic interference by double-stranded RNA in Caenorhabditis elegans. Nature. Feb. 19, 1998;391(6669):806-11.
Fisher et al., Photoinitiated Polymerization of Biomaterials. Annu Rev Mater Res. 2001;31:171-181.
Fisher et al., Synthesis and properties of photocross-linked poly-(propylene fumarate) scaffolds. J Biomater Sci Polym Ed. 2001;12(6):673-87.
Fominaya et al., Target cell-specific DNA transfer mediated by a chimeric multidomain protein. Novel non-viral gene delivery system. J Biol Chem. May 3, 1996;271(18):10560-8.
Friedmann, Human gene therapy—an immature genie, but certainly out of the bottle. Nat Med. Feb. 1996;2(2):144-7.
Fritz et al., Gene transfer into mammalian cells using histone-condensed plasmid DNA. Hum Gene Ther. Aug. 1, 1996;7(12):1395-404.
Fu et al., Visual Evidence of Acidic Environment Within Degrading Poly(lactic-co-glycolic acid) (PLGA) Microspheres. Pharma Res. 2000;17(1):100-06.
Gao et al., Hyperbranched polymers: from synthesis to applications. Prog. Polym. Sci. 29, 183-275.
Garg et al., Genetic tagging shows increased frequency and longevity of antigen-presenting, skin-derived dendritic cells in vivo. Nat Immunol. Sep. 2003;4(9):907-12. Epub Aug. 10, 2003. Corrigendum Nat Immunol Oct. 2003:4(10):1037.
Gebhart et al., Evaluation of polyplexes as gene transfer agents. J Control Release. Jun. 15, 2001;73(2-3):401-16.
Gerasimov et al., Cytosolic drug delivery using pH- and light-sensitive liposomes. Adv Drug Deliv Rev. Aug. 20, 1999;38(3):317-338.
Gonzalez et al., New class of polymers for the delivery of macromolecular therapeutics. Bioconjug Chem. Nov.-Dec. 1999;10(6):1068-74.
Haensler et al., Polyamidoamine cascade polymers mediate efficient transfection of cells in culture. Bioconjug Chem. Sep.-Oct. 1993;4(5):372-9.
Hanes et al., New advances in microsphere-based single-dose vaccines. Adv Drug Deliv Rev. Oct. 13, 1997;28(1):97-119.
Hansen et al., Re-examination and further development of a precise and rapid dye method for measuring cell growth/cell kill. J Immunol Methods. May 12, 1989;119(2):203-10.

(56) References Cited

OTHER PUBLICATIONS

He et al., Experimental Investigation into One-Step and Two-Steps Polymerization Via Michael Addition from Primary Amine. Polymer Preprints. 2001;42(2):335-36.
Hedley et al., Microspheres containing plasmid-encoded antigens elicit cytotoxic T-cell responses. Nat Med. Mar. 1998;4(3):365-8.
Hill et al., In vitro cytotoxicity of poly(amidoamine)s: relevance to DNA delivery. Biochim Biophys Acta. Apr. 19, 1999;1427(2):161-74.
Holter et al., Degree of branching in hyperbranched polymers. Acta Polymer 1997, 48:30-35.
Hope et al., Cationic lipids, phosphatidylethanolamine and the intracellular delivery of polymeric, nucleic acid-based drugs (review). Mol Membr Biol. Jan.-Mar. 1998;15(1):1-14.
Huang et al., Long-term in vivo gene expression via delivery of PEI-DNA condensates from porous polymer scaffolds. Hum Gene Ther. May 2005;16(5):609-17.
Hutchison et al., Robust polymer microfluidic device fabrication via contact liquid photolithographic polymerization (CLiPP). Lab Chip. 2004;4:658-662.
Hwang et al., Effects of structure of beta-cyclodextrin-containing polymers on gene delivery. Bioconjug Chem. Mar.-Apr. 2001;12(2):280-90.
Kabanov et al., DNA complexes with polycations for the delivery of genetic material into cells. Bioconjug Chem. Jan.-Feb. 1995;6(1):7-20.
Kabanov, Taking polycation gene delivery systems from in vitro to in vivo. Pharm Sci Technolo Today. Sep. 1999;2(9):365-372.
Kaczmarek et al., Optimization of a Degradable Polymer-Lipid Nanoparticle for Potent Systemic Delivery of mRNA to the Lung Endothelium and Immune Cells. Nano Lett. Oct. 10, 2018;18(10):6449-6454. doi: 10.1021/acs.nanolett.8b02917. Epub Sep. 20, 2018. PMID: 30211557; PMCID: PMC6415675.
Kaczmarek, Development of polymer—lipid nanoparticles for potent mRNA delivery to the lung. Sep. 2018. Thesis: Ph. D., Massachusetts Institute of Technology, Department of Chemical Engineering.
Kaczmarek et al., Polymer-Lipid Nanoparticles for Systemic Delivery of mRNA to the Lungs. Angew Chem Int Ed Engl. Oct. 24, 2016;55(44):13808-13812. doi: 10.1002/anie.201608450. Epub Sep. 30, 2016.
Kamat et al., Poly(β-amino ester) nanoparticle delivery of TP53 has activity against small cell lung cancer in vitro and in vivo. Mol Cancer Ther. Apr. 2013;12(4):405-15. doi: 10.1158/1535-7163.MCT-12-0956. Epub Jan. 30, 2013. PMID: 23364678; PMCID: PMC3624031.
Kargina et al., Self-Splitted Water-Soluble Ionogenic Polymers. Vysokomol Soedin Seriya. 1986;28:1139-44. Russian.
Kawata et al., Finer features for functional microdevices. Nature. Aug. 16, 2001;412(6848):697-8.
Khademhosseini et al., Molded polyethylene glycol microstructures for capturing cells within microfluidic channels. Lab Chip. Oct. 2004;4(5):425-30. Epub Jul. 26, 2004.
Korshak et al., Water-soluble anion exchange resins based on methacrylic beta-aminoesters. Vysokomolekulyarnye Soedineniya, Seriya B: Kratkie Soobscheniya. 1975;17(5):401-04.
Kukowska-Latallo et al., Efficient transfer of genetic material into mammalian cells using Starburst polyamidoamine dendrimers. Proc Natl Acad Sci U S A. May 14, 1996;93(10):4897-902.
Kwon et al., Pseudopoly(amino acids): A Study of the Synthesis and Characterization of Poly(trans-4-hydroxy-N-acyl-1-proline esters). Macromolecules. 1989;22:3250-55.
Leach et al., Bone engineering by controlled delivery of osteoinductive molecules and cells. Expert Opin Biol Ther. Jul. 2004;4(7):1015-27.
Leach et al., Photocrosslinked hyaluronic acid hydrogels: natural, biodegradable tissue engineering scaffolds. Biotechnology and Bioengineering. 2003;82:578-589.
Ledley, Nonviral gene therapy: the promise of genes as pharmaceutical products. Hum Gene Ther. Sep. 1995;6(9):1129-44.
Lim et al., A Self-Destroying Polycationic Polymer: Biodegradable Poly(4-hydroxy-1-proline ester). J Am Chem Soc. 1999;121:5633-39.
Lim et al., Biodegradable, endosome disruptive, and cationic network-type polymer as a highly efficient and nontoxic gene delivery carrier. Bioconjug Chem. Sep.-Oct. 2002;13(5):952-7.
Lim et al., Cationic hyperbranched poly(amino ester): a novel class of DNA condensing molecule with cationic surface, biodegradable three-dimensional structure, and tertiary amine groups in the interior. J Am Chem Soc. Mar. 14, 2001;123(10):2460-1.
Lim et al., Development of a Safe Gene Delivery System Using Biodegradable Polymer, Poly[α-(4-aminobutyl)-1-glycolic acid].J Am Chem Soc. 2000;122:6524-25.
Lim et al., Self-assembled ternary complex of cationic dendrimer, cucurbituril, and DNA: noncovalent strategy in developing a gene delivery carrier. Bioconjug Chem. Nov.-Dec. 2002;13(6):1181-5.
Linhardt et al., Free-Radical Synthesis of Poly(2-ethylacrylic acid) Fractions of Low Polydispersity: Effects of Molecular Weight and Polydispersity on the pH-Dependent Conformational Transition in Aqueous Solutions. Macromolecules. 1999;32:4457-59.
Linhardt et al., pH-Induced Fusion and Lysis of Phosphatidylcholine Vesicles by the Hydrophobic Polyelectrolyte Poly(2-ethylacrylic Acid). Langmuir. 2000;16:122-27.
Liu et al., Three-dimensional photopatterning of hydrogels containing living cells. Biomedical Microdevices. 2002;4:257-266.
Loan et al., Oligoamidoamines and oligoesteramines based on antibiotics containing ß-lactam ring. Euro Poly J. 1996;32:957-62.
Loan et al., Poly(amdio amine)s and poly(ester amine)s based on aromatic amines containg carboxyl groups. Macromolecular Chem and Phys. 1995;11:3525-33.
Luman et al., The convergent synthesis of poly(glycerol-succinic acid) dendritic macromolecules. Chemistry. Nov. 21, 2003;9(22):5618-26.
Luo et al., Synthetic DNA delivery systems. Nat Biotechnol. Jan. 2000;18(1):33-7.
Lynn et al., Degradable poly (ß-amino eaters): synthesis, characterization, and self-assembly with plasmid DNA. J Am Chem Soc. 2000;122:10761-68.
Lynn et al., pH-Responsive Polymer Microspheres: Rapid Release of Encapsulated Material within the Range of Intracellular pH. Angew Chem Int Ed Engl. May 4, 2001;40(9):1707-1710.
Mann et al., Smooth muscle cell growth in photopolymerized hydrogels with cell adhesive and proteolytically degradable domains: synthetic ECM analogs for tissue engineering. Biomaterials. Nov. 2001;22(22):3045-51.
Maruo et al., Three-dimensional microfabrication with two-photon-absorbed photopolymerization. Opt Lett. Jan. 15, 1997;22(2):132-4.
Mathiowitz et al., Novel Mircocapsules for Delivery Sytems. Reactive Polymers. 1987;6:275-283.
Mathiowitz et al., Polyanhydride Microspheres as Drug Carriers. I. Hot-Melt Microencapsulation. J Control Rel. 1987;5:13-22.
Mathiowitz et al., Polyanhydride Microspheres as Drug Carriers. II. Microencapsulation by Solvent Removal. J Appl Polymer Sci. 1988;35:755-74.
Midoux et al., Efficient gene transfer by histidylated polylysine/pDNA complexes. Bioconjug Chem. May-Jun. 1999;10(3):406-11.
Miller, Cationic Liposomes for Gene Therapy. Angew Chem Int Ed. 1998;37:1769-85.
Mulligan, The basic science of gene therapy. Science. May 14, 1993;260(5110):926-32.
Murphy et al., A combinatorial approach to the discovery of efficient cationic peptoid reagents for gene delivery. Proc Natl Acad Sci U S A. Feb. 17, 1998;95(4):1517-22.
Nguyen et al., Photopolymerizable hydrogels for tissue engineering applications. Biomaterials. Nov. 2002;23(22):4307-14.
O'Donnell et al., Preparation of microspheres by the solvent evaporation technique. Adv Drug Delivery Rev. 1997;28:25-42.
O'Hagan et al., Induction of potent immune responses by cationic microparticles with adsorbed human immunodeficiency virus DNA vaccines. J Virol. Oct. 2001;75(19):9037-43.
Odian et al., Step Polymerization. In: Principles of Polymerization. John Wiley & Sons, Inc. New York. 1991:73-89.

(56) References Cited

OTHER PUBLICATIONS

Okada, One- and three-month release injectable microspheres of the LH-RH superagonist leuprorelin acetate. Adv Drug Deliv Rev. Oct. 13, 1997;28(1):43-70.
Pack et al., Design of imidazole-containing endosomolytic biopolymers for gene delivery. Biotechnol Bioeng. Jan. 20, 2000;67(2):217-23.
Phillips et al., Enhanced antibody response to liposome-associated protein antigens: preferential stimulation of IgG2a/b production. Vaccine. 1992;10(3):151-8.
Prabha et al., Size-dependency of nanoparticle-mediated gene transfection: studies with fractionated nanoparticles. Int J Pharm. Sep. 5, 2002;244(1-2):105-15.
Putnam et al., Poly(4-hydroxy-1-proline ester): Low-Temperature Polycondensation and Plasmid DNA Complexation. Macromolecules 1999;32:3658-62.
Putnam et al., Polymer-based gene delivery with low cytotoxicity by a unique balance of side-chain termini. Proc Natl Acad Sci U S A. Jan. 30, 2001;98(3):1200-5. Epub Jan. 23, 2001.
Rao et al., Poly(butanediol Spermate): A Hydrolytically Labile Polyester-Based Nitric Oxide Carrier. J Bioactive Compatible Polymers. 1999;14:54-63.
Remy et al., Gene transfer with lipospermines and polyethylenimines. Adv Drug Deliv Rev. Mar. 2, 1998;30(1-3):85-95.
Roberts et al., Preliminary biological evaluation of polyamidoamine (PAMAM) Starburst dendrimers. J Biomed Mater Res. Jan. 1996;30(1):53-65.
Sahoo et al., Residual polyvinyl alcohol associated with poly (D,L-lactide-co-glycolide) nanoparticles affects their physical properties and cellular uptake. J Control Release. Jul. 18, 2002;82(1):105-14.
Sanford, The biolistic process. Trends Biotechnol. 1988;6:299-302.
Schaffer et al., Vector unpacking as a potential barrier for receptor-mediated polyplex gene delivery. Biotechnol Bioeng. Mar. 5, 2000;67(5):598-606.
Schwartz et al., Peptide-mediated cellular delivery. Curr Opin Mol Ther. Apr. 2000;2(2):162-7.
Schweikl et al., Triethylene glycol dimethacrylate induces large deletions in the hprt gene of V79 cells. Mutat Res. Jan. 2, 1999;438(1):71-8.
Shchori, Poly(secondary Amine)s from Diacrylates and Diamines. J Polym Sci Polymer. 1983;21:413-15.
Singh et al., Cationic microparticles: A potent delivery system for DNA vaccines. Proc Natl Acad Sci U S A. Jan. 18, 2000;97(2):811-6.
Smeds et al., Photocrosslinkable polysaccharides for in situ hydrogel formation. J Biomed Mater Res. Jan. 2001;54(1):115-21.
Somia et al., Gene therapy: trials and tribulations. Nat Rev Genet. Nov. 2000;1(2):91-9.
Strong et al., A General Synthetic Route to Defined, Biologically Active Multivalent Arrays. J Am Chem Soc. 1999;121:6193-96.
Su et al., In vitro and in vivo mRNA delivery using lipid-enveloped pH-responsive polymer nanoparticles. Mol Pharm. Jun. 6, 2011;8(3):774-87. doi: 10.1021/mp100390w. Epub Apr. 1, 2011.
Tang et al., In vitro gene delivery by degraded polyamidoamine dendrimers. Bioconjug Chem. Nov.-Dec. 1996;7(6):703-14.
Trubetskoy et al., Recharging cationic DNA complexes with highly charged polyanions for in vitro and in vivo gene delivery. Gene Ther. Feb. 2003;10(3):261-71.
Tweedie et al., Combinatorial material mechanics: high-throughput polymer synthesis and nanomechanical screening. Adv Mater. 2005;17:2599-2604.
Uhrich, Hyperbranched Polymers for Drug Discovery. Trends Polymer Sci. 1997;5:388-93.
Unal et al., Influence of filler addition on the mechanical properties of nylon-6 polymer. Journal of Reinforced Plastics and Composites. 2004;23(5):461-469.
Unkeless et al., Structure and function of human and murine receptors for IgG. Annu Rev Immunol. 1988;6:251-81.
Van De Wetering et al., Structure-activity relationships of water-soluble cationic methacrylate/methacrylamide polymers for nonviral gene delivery. Bioconjug Chem. Jul.-Aug. 1999;10(4):589-97.
Vázquez et al., Construction of hydrolytically-degradable thin films via layer-by-layer deposition of degradable polyelectrolytes. J Am Chem Soc. Nov. 27, 2002;124(47):13992-3.
Wagner et al., Influenza virus hemagglutinin HA-2 N-terminal fusogenic peptides augment gene transfer by transferrin-polylysine-DNA complexes: toward a synthetic virus-like gene-transfer vehicle. Proc Natl Acad Sci U S A. Sep. 1, 1992;89(17):7934-8.
Walter et al., Microencapsulation of DNA using poly(DL-lactide-co-glycolide): stability issues and release characteristics. J Control Release. Sep. 20, 1999;61(3):361-74.
Wang et al., Synthesis and Gene Delivery of Poly(amido amine)s with Different Branched Architecture. Biomacromolecules 2010;11(2):489-495. DOI: 10.1021/bm901215s.
Wang et al., Mechanical and rheological properties of HDPE/graphite composite with enhanced thermal conductivity. Polymer Composites. 2001;22(1):97-103.
West et al., Photopolymerized hydrogel materials for drug delivery applications. Reactive Polymers. 1995;25:139-147.
Wiethoff et al., Barriers to nonviral gene delivery. J Pharm Sci. Feb. 2003;92(2):203-17.
Wu et al., Effects of Chemistries of Trifunctional Amines on Mechanisms of Michael Addition Polymerizations with Diacrylates. Macromolecules, 2004;37(18):6763-6770. DOI: 10.1021/ma0493832.
Wu et al., Hyperbranched poly(amino ester)s with different terminal amine groups for DNA delivery. Biomacromolecules. Jun. 2006;7(6):1879-83.
Yang et al., A new approach to identifying genotoxic carcinogens: p53 induction as an indicator of genotoxic damage. Carcinogenesis. Jun. 1998;19(6):1117-25.
Zauner et al., Polylysine-based transfection systems utilizing receptor-mediated delivery. Adv Drug Deliv Rev. Mar. 2, 1998;30(1-3):97-113.
Zhou et al., Development of Branched Poly(5-Amino-1-pentanol-co-1,4-butanediol Diacrylate) with High Gene Transfection Potency Across Diverse Cell Types. ACS Appl Mater Interfaces. Dec. 21, 2016;8(50):34218-34226. Epub Dec. 6, 2016.
Zhou et al., Preparation of Poly(1-serine ester): A Structural Analogue of Conventional Poly(1-serine). Macromolecules. 1990;23:3399-406.
Zugates et al., Rapid optimization of gene delivery by parallel end-modification of poly(beta-amino ester)s. Mol Ther. Jul. 2007;15(7):1306-12. Epub Mar. 20, 2007.
PCT/US2019/058064, Apr. 9, 2020, International Search Report and Written Opinion.
PCT/US2019/058064, May 26, 2021, International Preliminary Report on Patentability.

* cited by examiner

| Parameter Estimates | | | | |
|---|---|---|---|---|
| Term | Estimate | Std Error | t Ratio | Prob>\|t\| |
| Intercept | 3.5743746 | 0.445379 | 8.03 | 0.0002* |
| N/P Ratio(25,100) | -1.146365 | 0.507811 | -2.26 | 0.0648 |
| PEG-Lipid C Length(14,18) | 0.7117284 | 0.507811 | 1.40 | 0.2106 |
| PEG-Lipid PEGMW(1000,5000) | -0.452306 | 0.507811 | -0.89 | 0.4074 |
| PEG-Lipid Molar Comp(1,10) | -0.521135 | 0.507811 | -1.03 | 0.3444 |
| Cholesterol(0,50) | 0.3810071 | 0.507811 | 0.75 | 0.4815 |
| DOPE(0,20) | 2.1489845 | 0.507811 | 4.23 | 0.0055* |

| Parameter Estimates | | | | |
|---|---|---|---|---|
| Term | Estimate | Std Error | t Ratio | Prob>\|t\| |
| Intercept | 3.5743746 | 0.528161 | 6.77 | <.0001* |
| DOPE(0,20) | 2.1489845 | 0.602196 | 3.57 | 0.0044* |

Parameter Estimates

| Term | Estimate | Std Error | t Ratio | Prob>|t| |
|---|---|---|---|---|
| Intercept | 5.6561734 | 0.14826 | 38.15 | <.0001* |
| DOPE mol%(20,50) | -0.635963 | 0.181581 | -3.50 | 0.0035* |
| PEG-Lipid mol%(2,9) | -0.935169 | 0.181581 | -5.15 | 0.0001* |
| PEG MW(1000,3000) | -0.529996 | 0.181581 | -2.92 | 0.0112* |

SEQUENCE LISTING

<160> NUMBER OF SEQ ID NOS: 2

<210> SEQ ID NO 1
<211> LENGTH: 1653
<212> TYPE: RNA
<213> ORGANISM: Artificial Sequence
<220> FEATURE:
<223> OTHER INFORMATION: Synthetic polynucleotide

<400> SEQUENCE: 1

```
auggaagaug ccaaaaacau uaagaagggc ccagcgccau ucuacccacu cgaagacggg      60
accgccggcg agcagcugca caaagccaug aagcgcuacg cccuggugcc cggcaccauc     120
gccuuuaccg acgcacauau cgagguggac auuaccuacg ccgaguacuu cgagaugagc     180
guucggcugg cagaagcuau gaagcgcuau gggcugaaua caaaccaucg gaucguggug     240
ugcagcgaga auagcuugca guucuucaug cccguguugg ugcccuguu caucgguguc     300 gcuguggccc cagcuaacga caucuacaac gagcgcgagc ugcugaacag caugggcauc     360
agccagccca ccgucguauu cgugagcaag aaagggcugc aaaagauccu caacgugcaa     420
aagaagcuac cgaucauaca aaagaucauc aucauggaua gcaagaccga cuaccagggc     480
uuccaaagca uguacaccuu cgugacuucc cauugccac ccggcuucaa cgaguacgac     540
uucgugcccg agagcuucga ccgggacaaa accaucgccc ugaucaugaa caguagugc     600 aguaccggau ugcccaaggg cguagcccua ccgcaccgca ccgcuugugu ccgauucagu     660
caugcccgcg accccaucuu cggcaaccag aucaucccg acaccgcuau ccucagcgug     720
```

```
gugccauuuc accacggcuu cggcauguuc accacgcugg gcuacuugau cugcggcuuu    780
cgggucgugc ucauguaccg cuucgaggag gagcuauucu ugcgcagcuu gcaagacuau    840
aagauucaau cugcccugcu ggugcccaca cuauuuagcu ucuucgcuaa gagcacucuc    900
aucgacaagu acgaccuaag caacuugcac gagaucgcca gcggcggggc gccgcucagc    960
aaggagguag gugaggccgu ggccaaacgc uuccaccuac caggcauccg ccagggcuac   1020
ggccugacag aaacaaccag cgccauucug aucacccccg aaggggacga caagccuggc   1080
gcaguaggca aggugugcc cuucuucgag gcuaaggugg uggacuugga caccgguaag   1140
acacugggug ugaaccagcg cggcgagcug ugcguccgug gccccaugau caugagcggc   1200
uacguuaaca accccgaggc uacaaacgcu cucaucgaca aggacggcug gcugcacagc   1260
ggcgacaucg ccuacuggga cgaggacgag cacuucuuca ucguggaccg gcugaagagc   1320
cugaucaaau acaagggcua ccagguagcc ccagccgaac uggagagcau ccugcugcaa   1380 cacccccaaca ucuucgacgc cggggucgcc ggccugcccg acgacgaugc cggcgagcug   1440
cccgccgcag ucgucgugcu ggaacacggu aaaaccauga ccgagaagga gaucguggac   1500
uauguggcca gccagguuac aaccgccaag aagcugcgcg gugguguugu guucguggac   1560
gaggugccua aaggacugac cggcaaguug gacgcccgca agauccgcga gauucucauu   1620
aaggccaaga agggcggcaa gaucgccgug uaa                                1653

<210> SEQ ID NO 2
<211> LENGTH: 581
<212> TYPE: RNA
<213> ORGANISM: Artificial Sequence
<220> FEATURE:
<223> OTHER INFORMATION: Synthetic polynucleotide

<400> SEQUENCE: 2
augguucgag ggugaacgaa gcgacugucu cggcgguucc cccuagccac gggugagaga     60
guugacgccg cgagucgcga guggacagug cggcugcggc ucggacguug accgacagug    120
agaggaccgg cacacagagc ccacaccucc cgucagccau cgcuaccuu gugaggcguu    180 gggacucuuu uccggugggg auccgccgau cacgacgccu ugcuagaccg ggggcuguga    240
auccacccaa gaucuuuauc uggcugggug gcgacugcgc gcuugacgcg cgaccgaccc    300
cgagcaaagu cauaacauag uggagccugg uugugggcu gucgaauacc ccuuggcgu    360 guucaggacg aaggggcguc auuugucacc ggugaucacc aucgugccag accgagcgca    420
cacuacacga gcugcuuaga ccgcauauca uacggaaggg ucuccuacu ucccacgacu    480 ccuuuugaca guucucacau ccucgugagu cagcgcccgc gagccuauuu uacgugggcac    540 uaggccuccg acccagucgc cucaccacac gaaacccugu a                        581
```

POLYMER-LIPIDS AND COMPOSITIONS

RELATED APPLICATIONS

This application claims priority under 35 USC 119(e) to U.S. Provisional Application No. 62/751,116, filed Oct. 26, 2018, the content of which is incorporated herein by reference in its entirety.

SEQUENCE LISTING

The Sequence Listing for this application is labeled "M1237.70085US01-SEQ.txt" which was created on Feb. 10, 2020 and is 3 KB in size. The entire content of the sequence listing is incorporated herein by reference in its entirety.

BACKGROUND mRNA therapeutics hold great potential for treating a variety of diseases through protein-replacement, immunomodulation, and gene editing.

Recent advances in the synthesis of in vitro transcribed (IVT) mRNA have triggered an expansion of research into the delivery of such mRNAs for a variety of therapeutic purposes.[1] For the controlled production of specific proteins in vivo, delivery of mRNA is particularly attractive given its transient expression and elimination of risk for genomic insertion compared to DNA.[2] Therapeutic mRNA delivery requires bypassing a number of barriers, including RNAse-mediated degradation, cellular entry, and endosomal escape.[3] Considerable effort has been dedicated to the development of vectors that can transport nucleic acids to target cells in vivo.[4,5] Non-viral nanoparticles, in particular, have emerged as an promising mRNA delivery vehicles for a variety of applications including immunotherapy[6-9], protein replacement[10-12], and gene editing.[13,14] However, like siRNA, the majority of work has focused on delivery to the liver following systemic delivery.[4,5,11,15-17] Thus, the broadest realization of RNA therapeutics in the clinic requires the development of delivery vehicles capable of potent, specific mRNA delivery to range of tissues, and in particular non-liver organs.

SUMMARY

In one aspect, provided herein is a polymer of Formula (I):

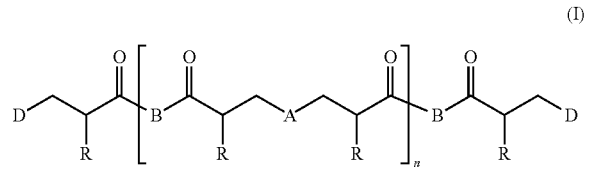

(I)

or a pharmaceutically acceptable salt thereof, wherein A, B, D, R, and n are as defined herein.

In certain embodiments, the molar ratio of A:B is about 1:1.2. In certain embodiments of the polymer, A is $A_1$ or $A_2$, wherein $A_1$ and $A_2$ are different amine diradicals, and wherein $A_1$ comprises an alkyl substituent. In certain embodiments, the molar ratio of $A_1:A_2$ is about 1:1.

In another aspect, provided herein is a composition comprising the polymer of Formula (I) and one or more of: a PEG lipid, a steroid, a phospholipid, and an agent. In certain embodiments, the agent is mRNA. In certain particular embodiments, the composition comprises the polymer of Formula (I), a steroid, a phospholipid, and mRNA. In certain embodiments, the composition is a nanoparticle. In certain embodiments, the composition is a pharmaceutical composition.

In another aspect, provided herein is a method of delivering an agent to a cell, comprising exposing the cell to a composition as described herein. In particular embodiments, the agent is a polynucleotide, such as mRNA. For mRNA delivery, the lungs are a particularly interesting target, given the variety of disease targets in endothelial[18,19], epithelial[20,21], and immune[22,23] pulmonary cells.

In another aspect, provided herein is a method of treating a disease, disorder, or condition from which a subject suffers, comprising administering to the subject in need thereof an effective amount of a composition as described herein. In certain particular embodiments, such a disease, disorder or condition is selected from proliferative disorders, inflammatory disorders, autoimmune disorders, painful conditions, and diseases of the lung, spleen, and liver.

BRIEF DESCRIPTION OF THE DRAWINGS

(FIG. 1A) Monomers used in synthesis screen for PBAE terpolymers. The diacrylate and amines step-polymerize via Michael addition, and can be end-capped in a separate step by keeping the diacrylate in excess during polymerization. (FIG. 1B) Schematic depicting the formulation moieties used in the formulation screen for in vivo mRNA delivery. mRNA binds with the polymer on the basis of its cationic charge, while the alkylamine in the polymer provides a non-covalent handle for hydrophobic moieties to incorporate into the nanoparticle.

(FIG. 3A) A definitive screen revealed one formulation that was more potent than the original (i.e. A1 polymer with 7 mol % C14-PEG2000 PEG-lipid). This formulation, along with statistical data from the screen, was used to develop the parameter space for a subsequent partial factorial screen. (FIG. 3B) The partial factorial screen had a greater number of formulations more potent in the lung (22% vs. 7%), but several formulations showed high luciferase signal in the spleen. (FIG. 3C) By optimizing the mol % of PEG-lipid in the formulation, high lung-specificity could be obtained. (FIG. 3D) The optimized PBAE polymer/formulation (A1/L3) is orders of magnitude more potent than jetPEI across multiple mRNA doses (n=3 for all experiments).

(FIG. 4A) Percentages of cell types that were TdTomato+ (bars, left axis), indicating successful transfection with Cre mRNA using A1-L3 nanoparticles. Symbols (● for treated mice, ▼ for control mice, right axis) represent percentages of total cells which were either endothelial or immune cells (n=3). (FIG. 4B) Identification of immune cell (CD45+) subtypes which express tdTomato following delivery of Cre mRNA via A1-L3 nanoparticles in Ai14 mice (n=2).

DEFINITIONS

Figure 1A:
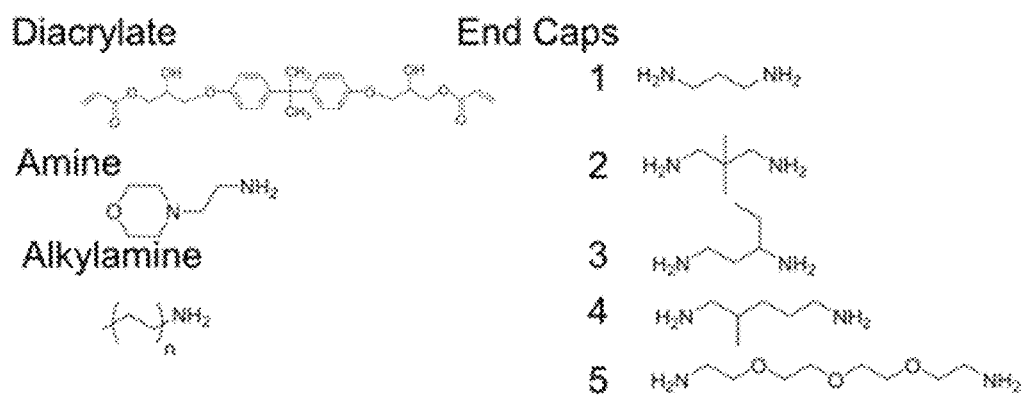
FIGS. 1A-1B.

For convenience, certain terms employed herein, in the specification, examples and appended claims are collected herein.

Unless otherwise required by context, singular terms shall include pluralities, and plural terms shall include the singular.

The following definitions are more general terms used throughout the present application:

The singular terms "a," "an," and "the" include plural references unless the context clearly indicates otherwise. Similarly, the word "or" is intended to include "and" unless the context clearly indicates otherwise.

Other than in the examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, or more typically, within 5%, 4%, 3%, 2%, or 1% of a given value or range of values.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can include one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

In a formula, ~~~ is a single bond where the stereochemistry of the moieties immediately attached thereto is not specified, --- is absent or a single bond, and === or ≡≡≡ is a single or double bond.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The term "aliphatic" includes both saturated and unsaturated, straight chain (i.e., unbranched), branched, acyclic, cyclic, or polycyclic aliphatic hydrocarbons, which are optionally substituted with one or more functional groups. Likewise, the term "heteroaliphatic" refers to heteroalkyl, heteroalkenyl, heteroalkynyl, and heterocyclic groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-100 aliphatic carbon atoms. In certain other embodiments, the alkyl, alkenyl, and alkynyl groups employed in the disclosure contain 1-50 aliphatic carbon atoms. In certain other embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, npropyl, isopropyl, cyclopropyl, —CH$_2$-cyclopropyl, vinyl, allyl, n-butyl, sec-butyl, isobutyl, tertbutyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties, and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group. In some embodiments, an alkyl group has 1 to 1000 carbon atoms ("$C_1$-$C_{1000}$ alkyl"), 1 to 900 carbon atoms ("$C_1$-$C_{900}$ alkyl"), 1 to 800 carbon atoms ("$C_1$-$C_{800}$ alkyl"), 1 to 700 carbon atoms ("$C_1$-$C_{700}$ alkyl"), 1 to 600 carbon atoms ("$C_1$-$C_{600}$ alkyl"), 1 to 500 carbon atoms ("$C_1$-$C_{500}$ alkyl"), 1 to 400 carbon atoms ("$C_1$-$C_{400}$ alkyl"), 1 to 300 carbon atoms ("$C_1$-$C_{300}$ alkyl"), 1 to 200 carbon atoms ("$C_1$-$C_{200}$ alkyl"), 1 to 100 carbon atom ("$C_1$-$C_{100}$ alkyl"). In some embodiments, an alkyl group has 1 to 10 carbon atoms ("$C_1$-$C_{10}$ alkyl"), 1 to 9 carbon atoms ("$C_1$-$C_9$ alkyl"), 1 to 8 carbon atoms ("$C_1$-$C_8$ alkyl"), 1 to 7 carbon atoms ("$C_1$-$C_7$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents.

The term "alkenyl" refers to a radical of a straight-chain or branched hydrocarbon group having from 2 to 1000 carbon atoms and one or more carbon-carbon double bonds (e.g., 1, 2, 3, or 4 double bonds). In some embodiments, an alkenyl group has 2 to 1000 carbon atoms ("$C_2$-$C_{1000}$ alkenyl"), 2 to 900 carbon atoms ("$C_2$-$C_{900}$ alkenyl"), 2 to 800 carbon atoms ("$C_2$-$C_{800}$ alkenyl"), 2 to 700 carbon atoms ("$C_2$-$C_{700}$ alkenyl"), 2 to 600 carbon atoms ("$C_2$-$C_{600}$ alkenyl"), 2 to 500 carbon atoms ("$C_2$-0500 alkenyl"), 2 to 400 carbon atoms ("$C_2$-$C_{400}$ alkenyl"), 2 to 300 carbon atoms ("$C_2$-$C_{300}$ alkenyl"), 2 to 200 carbon atoms ("$C_2$-$C_{200}$ alkenyl"), 2 to 100 carbon atom ("$C_2$-$C_{100}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Unless otherwise specified, each instance of an alkenyl group is independently unsubstituted (an "unsubstituted alkenyl") or substituted (a "substituted alkenyl") with one or more substituents. In an alkenyl group, a C=C double bond for which the stereochemistry is not specified (e.g., —CH=CHCH$_3$,

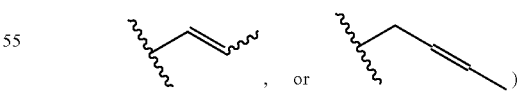

, or )

may be in the (E)- or (Z)-configuration.

The term "alkynyl" refers to a radical of a straight-chain or branched hydrocarbon group having from 2 to 1000 carbon atoms and one or more carbon-carbon triple bonds (e.g., 1, 2, 3, or 4 triple bonds). In some embodiments, an alkynyl group has 2 to 1000 carbon atoms ("$C_2$-$C_{1000}$ alkynyl"), 2 to 900 carbon atoms ("$C_2$-$C_{900}$ alkynyl"), 2 to 800 carbon atoms ("$C_2$-$C_{800}$ alkynyl"), 2 to 700 carbon atoms ("$C_2$-$C_{700}$ alkynyl"), 2 to 600 carbon atoms ("$C_2$-$C_{600}$ alkynyl"), 2 to 500 carbon atoms ("$C_2$-$C_{500}$ alkynyl"), 2 to 400 carbon atoms ("$C_2$-$C_{400}$ alkynyl"), 2 to 300 carbon atoms ("$C_2$-$C_{300}$ alkynyl"), 2 to 200 carbon atoms ("$C_2$-$C_{200}$ alkynyl"), 2 to 100 carbon atom ("$C_2$-$C_{100}$ alkynyl"). In some embodiments, an alkynyl group has 2 to 9 carbon atoms ("$C_{2-9}$ alkynyl"), 2 to 8 carbon atoms ("$C_{2-8}$ alkynyl"), 2 to 7 carbon atoms ("$C_{2-7}$ alkynyl"), 2 to 6 carbon atoms ("$C_2$-$C_{500}$ alkynyl"), 2 to 5 carbon atoms ("$C_{2-5}$ alkynyl"), 2 to 4 carbon atoms ("$C_{2-4}$ alkynyl"), 2 to 3 carbon atoms ("$C_{2-3}$ alkynyl"), or 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Unless otherwise specified, each instance of an alkynyl group is independently unsubstituted (an "unsubstituted alkynyl") or substituted (a "substituted alkynyl") with one or more substituents.

The term "heteroalkyl" refers to an alkyl group which further includes at least one heteroatom (e.g., 1, 2, 3, or 4 heteroatoms) selected from oxygen, nitrogen, phosphorus, or sulfur within (i.e., inserted between adjacent carbon atoms of) and/or placed at one or more terminal position(s) of the parent chain. In certain embodiments, a heteroalkyl group refers to a saturated group having from 1 to 1000 carbon atoms and 1 or more heteroatoms within the parent chain ("$C_1$-$C_{1000}$ heteroalkyl"), 1 to 900 carbon atoms and 1 or more heteroatoms within the parent chain ("$C_1$-$C_{900}$ heteroalkyl"), 1 to 800 carbon atoms and 1 or more heteroatoms within the parent chain ("$C_1$-$C_{800}$ heteroalkyl"), 1 to 700 carbon atoms and 1 or more heteroatoms within the parent chain ("$C_1$-$C_{700}$ heteroalkyl"), 1 to 600 carbon atoms and 1 or more heteroatoms within the parent chain ("$C_1$-$C_{600}$ heteroalkyl"), 1 to 500 carbon atoms and 1 or more heteroatoms within the parent chain ("$C_1$-$C_{500}$ heteroalkyl"), 1 to 400 carbon atoms and for more heteroatoms within the parent chain ("$C_1$-$C_{400}$ heteroalkyl"), 1 to 300 carbon atoms and 1 or more heteroatoms within the parent chain ("$C_1$-$C_{300}$ heteroalkyl"), 1 to 200 carbon atoms and 1 or more heteroatoms within the parent chain ("$C_1$-$C_{200}$ heteroalkyl"), or 1 to 100 carbon atoms and 1 or more heteroatoms within the parent chain ("$C_1$-$C_{100}$ heteroalkyl"). In certain embodiments, a heteroalkyl group refers to a saturated group having from 1 to 10 carbon atoms and 1 or more heteroatoms within the parent chain ("$C_1$-$C_{10}$ heteroalkyl"), 1 to 9 carbon atoms and 1 or more heteroatoms within the parent chain ("$C_1$-$C_9$ heteroalkyl"), 1 to 8 carbon atoms and 1 or more heteroatoms within the parent chain ("$C_1$-$C_8$ heteroalkyl"), 1 to 7 carbon atoms and 1 or more heteroatoms within the parent chain ("$C_1$-$C_7$ heteroalkyl"), 1 to 6 carbon atoms and 1 or more heteroatoms within the parent chain ("$C_1$-$C_6$ heteroalkyl"), 1 to 5 carbon atoms and 1 or more heteroatoms within the parent chain ("$C_1$-$C_5$ heteroalkyl"), 1 to 4 carbon atoms and for more heteroatoms within the parent chain ("$C_1$-$C_4$ heteroalkyl"), 1 to 3 carbon atoms and 1 or more heteroatoms within the parent chain ("$C_1$-$C_3$ heteroalkyl"), 1 to 2 carbon atoms and 1 heteroatom within the parent chain ("$C_1$-$C_2$ heteroalkyl"), or 1 carbon atom and 1 heteroatom ("$C_1$ heteroalkyl"). Unless otherwise specified, each instance of a heteroalkyl group is independently unsubstituted (an "unsubstituted heteroalkyl") or substituted (a "substituted heteroalkyl") with one or more substituents.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a saturated group having from 1 to 1000 carbon atoms and 1 or more heteroatoms within the parent chain ("hetero$C_1$-$C_{1000}$ alkenyl"), 1 to 900 carbon atoms and 1 or more heteroatoms within the parent chain ("hetero$C_1$-$C_{900}$ alkenyl"), 1 to 800 carbon atoms and 1 or more heteroatoms within the parent chain ("hetero$C_1$-$C_{800}$ alkenyl"), 1 to 700 carbon atoms and 1 or more heteroatoms within the parent chain ("hetero$C_1$-$C_{700}$ alkenyl"), 1 to 600 carbon atoms and 1 or more heteroatoms within the parent chain ("hetero$C_1$-$C_{600}$ alkenyl"), 1 to 500 carbon atoms and 1 or more heteroatoms within the parent chain ("hetero$C_1$-$C_{500}$ alkenyl"), 1 to 400 carbon atoms and for more heteroatoms within the parent chain ("hetero$C_1$-$C_{400}$ alkenyl"), 1 to 300 carbon atoms and 1 or more heteroatoms within the parent chain ("hetero$C_1$-$C_{300}$ alkenyl"), 1 to 200 carbon atoms and 1 or more heteroatoms within the parent chain ("hetero$C_1$-$C_{200}$ alkenyl"), or 1 to 100 carbon atoms and 1 or more heteroatoms within the parent chain ("hetero$C_1$-$C_{100}$ alkenyl"). In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and for 2 heteroatoms within the parent chain ("hetero$C_{2-4}$ alkenyl"). In some embodiments, a heteroalkenyl group has 2 to 3 carbon atoms, at least one double bond, and 1 heteroatom in the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a saturated group having from 1 to 1000 carbon atoms and 1 or more heteroatoms within the parent chain ("hetero$C_1$-$C_{1000}$ alkynyl"), 1 to 900 carbon atoms and 1 or more heteroatoms within the parent chain ("hetero$C_1$-$C_{900}$ alkynyl"), 1 to 800 carbon atoms and 1 or more heteroatoms within the parent chain ("hetero$C_1$-$C_{800}$ alkynyl"), 1 to 700 carbon atoms and 1 or more heteroatoms within the parent chain ("heteroC$_1$-C$_{700}$ alkynyl"), 1 to 600 carbon atoms and 1 or more heteroatoms within the parent chain ("heteroC$_1$-C$_{600}$ alkynyl"), 1 to 500 carbon atoms and 1 or more heteroatoms within the parent chain ("heteroC$_1$-C$_{500}$ alkynyl"), 1 to 400 carbon atoms and for more heteroatoms within the parent chain ("heteroC$_1$-C$_{400}$ alkynyl"), 1 to 300 carbon atoms and 1 or more heteroatoms within the parent chain ("heteroC$_1$-C$_{300}$ alkynyl"), 1 to 200 carbon atoms and 1 or more heteroatoms within the parent chain ("heteroC$_1$-C$_{200}$ alkynyl"), or 1 to 100 carbon atoms and 1 or more heteroatoms within the parent chain ("heteroC$_1$-C$_{100}$ alkynyl"). In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" or "cycloalkyl" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"), 3 to 7 ring carbon atoms ("C$_{3-7}$ carbocyclyl"), 3 to 6 ring carbon atoms ("C$_{3-6}$ carbocyclyl"), 4 to 6 ring carbon atoms ("C$_{4-6}$ carbocyclyl"), 5 to 6 ring carbon atoms ("C$_{5-6}$ carbocyclyl"), or 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_3$-8 carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, phosphorus, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents.

In some embodiments, a heterocyclyl group is a 5-10 membered non-aromatic ring system having ring carbon atoms and 1-4 ring heteroatoms, wherein each heteroatom is independently selected from nitrogen, oxygen, phosphorus, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorus, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorus, and sulfur ("5-6 membered heterocyclyl"). In some embodiments, the 5-6 membered heterocyclyl has 1-3 ring heteroatoms selected from nitrogen, oxygen, phosphorus, and sulfur. In some embodiments, the 5-6 membered heterocyclyl has 1-2 ring heteroatoms selected from nitrogen, oxygen, phosphorus, and sulfur. In some embodiments, the 5-6 membered heterocyclyl has 1 ring heteroatom selected from nitrogen, oxygen, phosphorus, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl, and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydroyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 r electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group be monovalent or may have more than one point of attachment to another moiety (e.g., it may be divalent, trivalent, etc), although the valency may be specified directly in the name of the group. For example, "triazoldiyl" refers to a divalent triazolyl moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

As understood from the above, alkyl, alkenyl, alkynyl, carbocyclyl, aryl, and heteroaryl groups are, in certain embodiments, optionally substituted. Optionally substituted refers to a group which may be substituted or unsubstituted (e.g., "substituted" or "unsubstituted" alkyl). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Affixing the suffix "ene" to a group indicates the group is a polyvalent (e.g., bivalent, trivalent, tetravalent, or pentavalent) moiety. In certain embodiments, affixing the suffix "ene" to a group indicates the group is a bivalent moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$), —SO$_2$R$^{ee}$, —SO$_2$O R$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl), —N(C$_{1-6}$ alkyl), —N(C$_{1-6}$ alkyl)$_3^+$X$^-$, —NH(C$_{1-6}$ alkyl)$^+$X$^-$, —NH$_2$(C$_{1-6}$ alkyl)+X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl), —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl), —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl), —C(=NH)NH(C$_{1-6}$ alkyl), —C(=NH)NH$_2$, —OC(=NH)N(C$_{1-6}$ alkyl), —OC(NH)NH(C$_{1-6}$ alkyl), —OC(NH)NH$_2$, —NHC(NH)N(C$_{1-6}$ alkyl), —NHC(=NH) NH$_2$, —NHSO$_2$(C$_{1-6}$ alkyl), —SO$_2$N(C$_{1-6}$ alkyl), —SO$_2$NH (C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl), C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl), —P(=O)(C$_{1-6}$ alkyl), —OP(=O)(C$_{1-6}$ alkyl), —OP(=O) (OC$_{1-6}$ alkyl), C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein $X^-$ is a counterion.

In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O) R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, or —NO$_2$.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N (R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl] amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH.

The term "thiol" or "thio" refers to the group —SH.

The term "amine" or "amino" refers to the group —NH— or —NH$_2$, wherein each H is optionally, independently replaced with an alkyl, heteroalkyl, aryl, or heteroaryl group.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this disclosure include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ \text{alkyl})_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ \text{alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions, such as halide, hydroxide, carboxylate, sulfate, phosphate, nitrate, lower alkyl sulfonate, and aryl sulfonate.

As used herein, the term "agent" means a molecule, group of molecules, complex or substance administered to an organism for diagnostic, therapeutic, preventative medical, or veterinary purposes. In certain embodiments, the agent is a pharmaceutical agent (e.g., a therapeutic agent, a diagnostic agent, or a prophylactic agent). In certain embodiments, the compositions disclosed herein comprise an agent(s), e.g., a first therapeutic agent (e.g., at least one (including, e.g., at least two, at least three). In some embodiments, the compositions (e.g., macromonomers, conjugates, or particles) can further comprise a second therapeutic agent, a targeting moiety, a diagnostic moiety as described herein.

As used herein, the term "therapeutic agent" includes an agent that is capable of providing a local or systemic biological, physiological, or therapeutic effect in the biological system to which it is applied. For example, a therapeutic agent can act to control tumor growth, control infection or inflammation, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism.

An agent (e.g., a therapeutic agent) can include a wide variety of different compounds, including chemical compounds and mixtures of chemical compounds (e.g., small organic or inorganic molecules) such as drug compounds (e.g., compounds approved for human or veterinary use by the U.S. Food and Drug Administration as provided in the Code of Federal Regulations (CFR)); targeting agents; isotopically labeled chemical compounds; agents useful in bioprocessing; carbohydrates; saccharines; monosaccharides; oligosaccharides; polysaccharides; biological macromolecules (e.g., peptides, proteins, and peptide analogs and derivatives); peptidomimetics; antibodies and antigen binding fragments thereof; nucleic acids (e.g., DNA or RNA); nucleotides; nucleosides; oligonucleotides; antisense oligonucleotides; polynucleotides; nucleic acid analogs and derivatives; nucleoproteins; mucoproteins; lipoproteins; synthetic polypeptides or proteins; small molecules linked to proteins; glycoproteins; steroids; lipids; hormones; vitamins; vaccines; immunological agents; an extract made from biological materials such as bacteria, plants, fungi, or animal cells; animal tissues; naturally occurring or synthetic compositions; and any combinations thereof.

In some embodiments, the agent is in the form of a prodrug. The term "prodrug" refer to a compound that becomes active, e.g., by solvolysis, reduction, oxidation, or under physiological conditions, to provide a pharmaceutically active compound, e.g., in vivo. A prodrug can include a derivative of a pharmaceutically active compound, such as, for example, to form an ester by reaction of the acid, or acid anhydride, or mixed anhydrides moieties of the prodrug moiety with the hydroxyl moiety of the pharmaceutical active compound, or to form an amide prepared by the acid, or acid anhydride, or mixed anhydrides moieties of the prodrug moiety with a substituted or unsubstituted amine of the pharmaceutically active compound. Simple aliphatic or aromatic esters, amides, and anhydrides derived from acidic groups may comprise prodrugs. In some embodiments, the conjugate or particle described herein incorporates one therapeutic agent or prodrug thereof. In some embodiments, the conjugate or particle described herein incorporates more than one therapeutic agents or prodrugs.

In some embodiments, the agent (e.g., a therapeutic agent) is a small molecule. As used herein, the term "small molecule" can refer to compounds that are "natural product-like." However, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary agents (e.g., a therapeutic agents) in the compositions include, but are not limited to, those found in *Harrison's Principles of Internal Medicine*, 13th Edition, Eds. T. R. Harrison et al. McGraw-Hill N.Y., NY; Physicians' Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

Agents, e.g., therapeutic agents, include the herein disclosed categories and specific examples. It is not intended that the category be limited by the specific examples. Those of ordinary skill in the art will recognize also numerous other compounds that fall within the categories and that are useful according to the present disclosure.

Examples of therapeutic agents include, but are not limited to, antimicrobial agents, analgesics, antiinflammatory agents, counterirritants, coagulation modifying agents, diuretics, sympathomimetics, anorexics, antacids and other gastrointestinal agents; antiparasitics, antidepressants, anti-hypertensive, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anti-cancer properties, or a combination thereof. Other suitable therapeutic agents include contraceptives and vitamins as well as micro- and macronutrients. Still other examples include antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; anti-hypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

In certain instances, the diagnostic agent is an imaging agent or contrast agent. The terms "imaging agent" and "contrast agent" refer to a substance used to enhance the contrast of structures or fluids within the body in medical imaging. It is commonly used to enhance the visibility of blood vessels and the gastrointestinal tract in medical imaging.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellisvan Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/ lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, postsurgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's disease, ankylosing spondylitis, Lyme disease, Guillain-Barré syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

An "effective amount" of a composition described herein refers to an amount sufficient to elicit the desired biological response. An effective amount of a composition described herein may vary depending on such factors as the desired biological endpoint, the pharmacokinetics of the composition, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a composition or pharmaceutical composition described herein in a single dose. In certain embodiments, an effective amount is the combined amounts of a composition or pharmaceutical composition described herein in multiple doses.

A "therapeutically effective amount" of a composition described herein is an amount sufficient to provide a therapeutic benefit in the treatment of a condition or to delay or minimize one or more symptoms associated with the condition. A therapeutically effective amount of a composition means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a composition described herein is an amount sufficient to prevent a condition, or one or more symptoms associated with the condition or prevent its recurrence. A prophylactically effective amount of a composition means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The terms "nucleic acid" or "nucleic acid sequence", "nucleic acid molecule", "nucleic acid fragment" or "polynucleotide" are used interchangeably. A polynucleotide molecule is a biopolymer composed of nucleotide monomers covalently bonded in a chain. DNA (deoxyribonucleic acid) and RNA (ribonucleic acid) are examples of polynucleotides with distinct biological function. DNA consists of two chains of polynucleotides, with each chain in the form of a helical spiral. RNA is more often found in nature as a single-strand folded onto itself. Exemplary types of RNA include double-stranded RNA (dsRNA), small interfering RNA (siRNA), short hairpin (shRNA), microRNA (miRNA), messenger RNA (mRNA), antisense RNA, transfer RNA (tRNA), small nuclear RNA (snRNA), and ribosomal RNA (rRNA).

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

The term "siRNA" or "siRNA molecule" refers to small inhibitory RNA duplexes that induce the RNA interference (RNAi) pathway, where the siRNA interferes with the expression of specific genes with a complementary nucleotide sequence. siRNA molecules can vary in length (e.g., between 18-30 or 20-25 basepairs) and contain varying degrees of complementarity to their target mRNA in the antisense strand. Some siRNA have unpaired overhanging bases on the 5' or 3' end of the sense strand and/or the antisense strand. The term siRNA includes duplexes of two separate strands, as well as single strands that can form hairpin structures comprising a duplex region.

The term "RNA interference" or "RNAi" refers to a biological process in which RNA molecules inhibit gene expression or translation, by neutralizing targets mRNA molecules. Since the discovery of RNAi and its regulatory potentials, it has become evident that RNAi has immense potential in suppression of desired genes. RNAi is now known as precise, efficient, stable, and better than antisense technology for gene suppression. Two types of small ribonucleic acids molecules are central to RNA interference: miRNA and siRNA. These small RNAs can bind to mRNA molecules and either increase or decrease their activity (e.g., preventing an mRNA from being translated into a protein). The RNAi pathway is found in many eukaryotes, including animals, and is initiated by the enzyme Dicer, which cleaves long dsRNA molecules into short double-stranded fragments of ~20 nucleotide siRNAs. Each siRNA is unwound into two single-stranded RNAs (ssRNAs), the passenger strand and the guide strand. The passenger strand is degraded and the guide strand is incorporated into the RNA-induced silencing complex (RISC). The most well-studied outcome is post-transcriptional gene silencing, which occurs when the guide strand pairs with a complementary sequence in a mRNA molecule and induces cleavage by Argonaute 2 (Ago2), the catalytic component of the RISC complex. In some organisms, this process spreads systematically, despite the initially limited molar concentrations of siRNA.

The term "biodegradable" or "biodegradation" refers to the disintegration of materials by biological means. Organic material can be degraded aerobically or anaerobically. Decomposition of biodegradable substances may include both biological and abiotic steps.

The term "biocompatible" or "biocompatibility" refers to the ability of a material to perform with an appropriate host response in a specific situation. In particular, the terms refer to the ability of a biomaterial to perform its desired function with respect to a medical therapy without eliciting any undesirable local or systematic effects in the recipient or beneficiary of that therapy, but generating the most appropriate beneficial cellular or tissue response in that specific situation, and optimizing the clinically relevant performance of that therapy.

The term "average polydispersity" (PDI), as used herein, refers to a measure of the distribution of molecular size in a mixture, e.g., as determined by a chromatographic method, such as gel permeation chromatography (See, e.g., Helmut, D. *Gel Chromatography, Gel Filtration, Gel Permeation, Molecular Sieves: A Laboratory Handbook*; Springer-Verlag, 1969) or size exclusion chromatography (See, e.g., Trathnigg, B. Determination of MWD and Chemical Composition of Polymers by Chromatographic Techniques. *Prog. Polym. Sci.* 1995, 20, 615-650.), or through dynamic light scattering (See, e.g., Berne, B. J.; Pecora, R. *Dynamic Light Scattering*. Courier Dover Publications (2000)).

The disclosure is not intended to be limited in any manner by the above exemplary listing of substituents. Additional terms may be defined in other sections of this disclosure.

DETAILED DESCRIPTION OF CERTAIN EMBODIMENTS

The present disclosure relates to improvements in the selection and formulation of PBAE polymers using a design of experiment approach, which uses statistical methods to limit necessary experimental conditions, and to improved PBAE polymers and formulations. A multiple order-of-magnitude increase is reported in the potency of mRNA delivery in vivo, while maintaining lung specificity.

Polymers of Formula (I)

In one aspect, provided herein is a polymer of Formula (I):

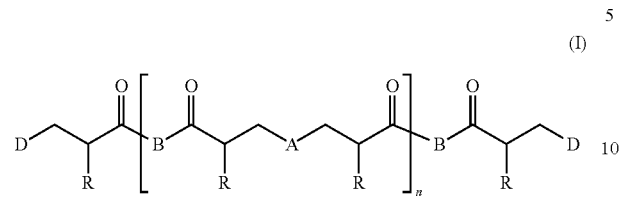
(I)

or a pharmaceutically acceptable salt thereof, wherein:
each A independently is $A_1$ or $A_2$;
$A_1$ is —N($R_1$)—; and
$A_2$ is —N($R_2$)—;
each B independently is optionally substituted aliphatic, optionally substituted heteroaliphatic, optionally substituted aryl, or optionally substituted heteroaryl;
each D is —$XR_3$;
each R is independently is hydrogen, halide, optionally substituted aliphatic, or optionally substituted heteroaliphatic;
each $R_1$ is optionally substituted alkyl;
each $R_2$ independently is optionally substituted aliphatic, optionally substituted heteroaliphatic, optionally substituted aryl, optionally substituted heteroaryl;
each $R_3$ independently is optionally substituted aliphatic, optionally substituted heteroaliphatic, optionally substituted aryl, optionally substituted heteroaryl, or a nitrogen protecting group;
each X independently is O, S, NH, or $NR_X$, wherein $R_X$ is optionally substituted aliphatic, optionally substituted heteroaliphatic, optionally substituted aryl, or optionally substituted heteroaryl; and
n is 1-10000.

Variable A

Variable A is a divalent amine radical having the structure of $A_1$ or $A_2$. $A_1$ is —N($R_1$)—, wherein $R_1$ is optionally substituted alkyl. In certain embodiments, $A_1$ is selected from the following diradicals:

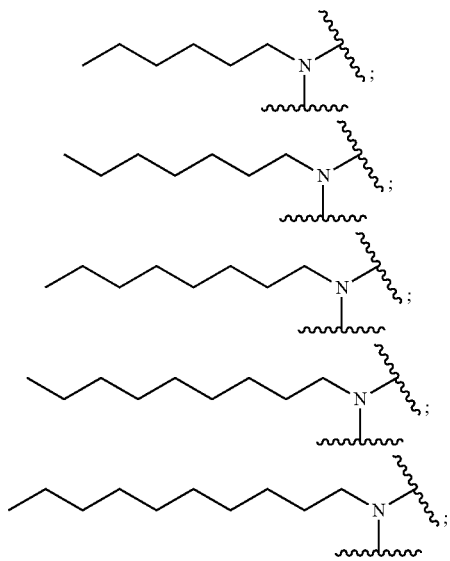

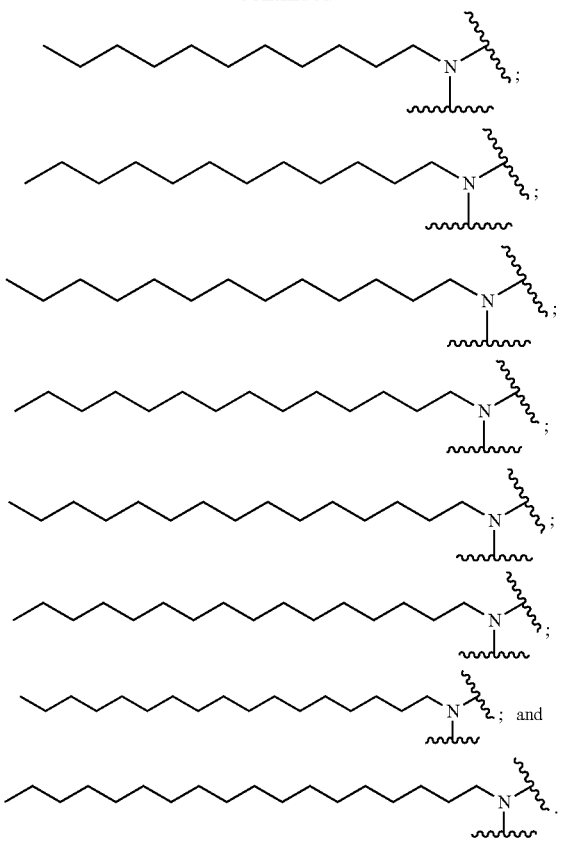

In certain embodiments, $A_2$ is selected from:

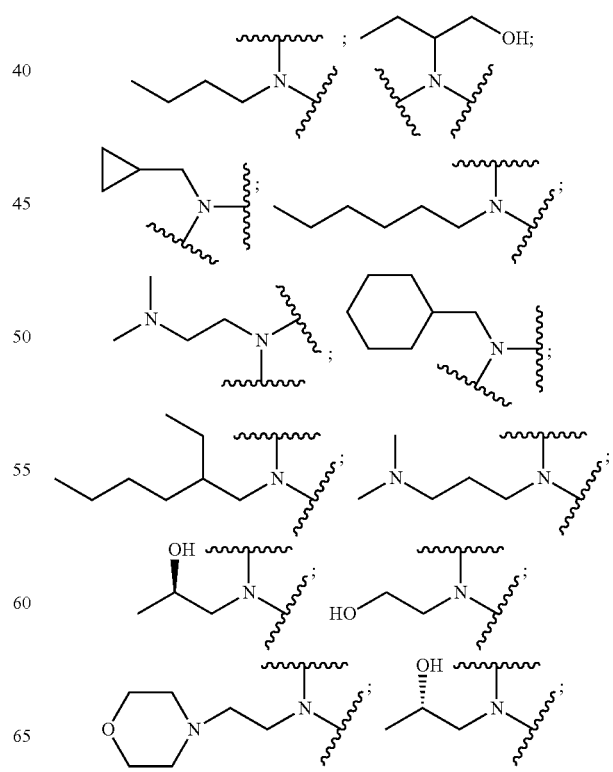

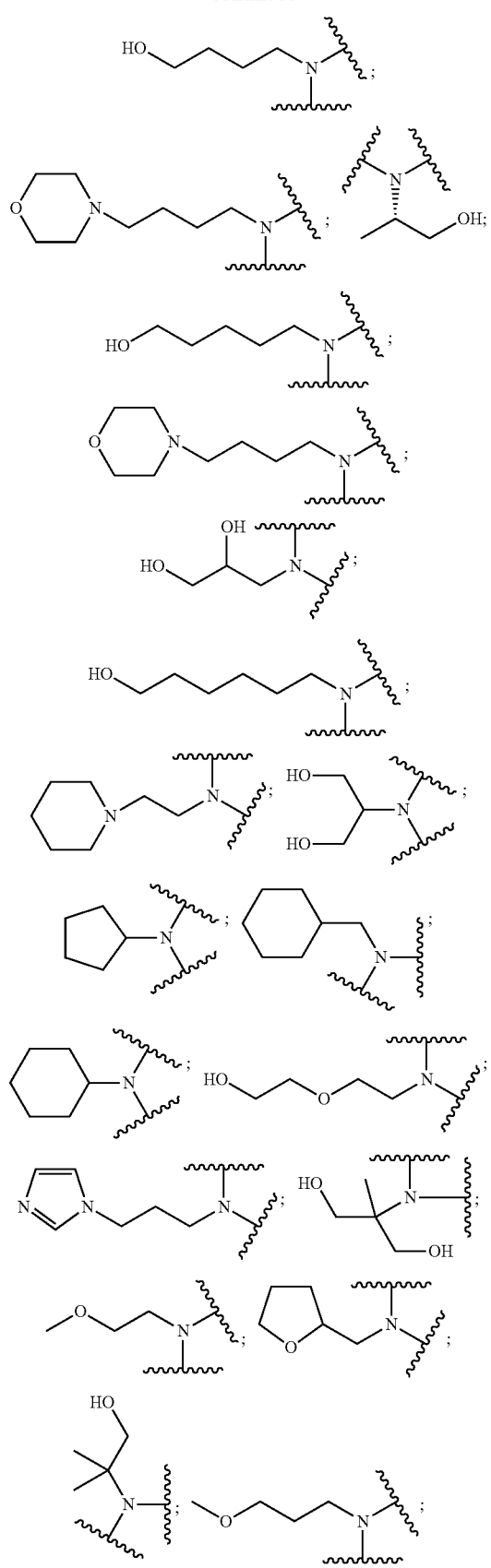
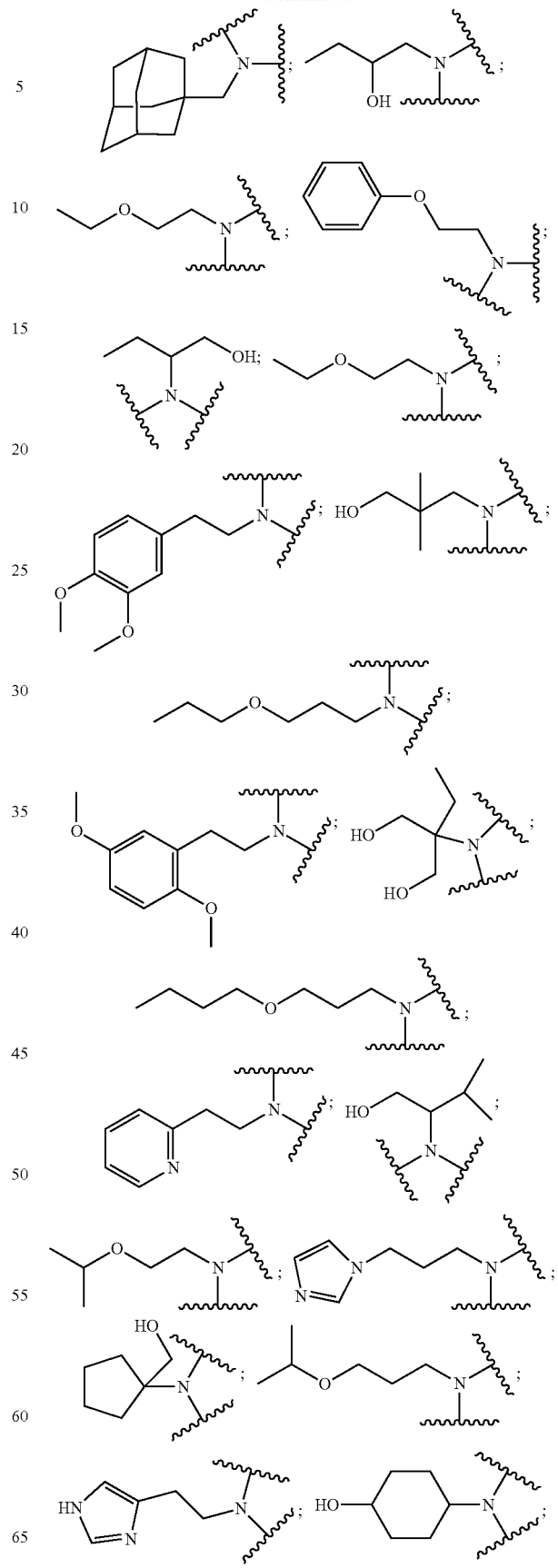

37
-continued
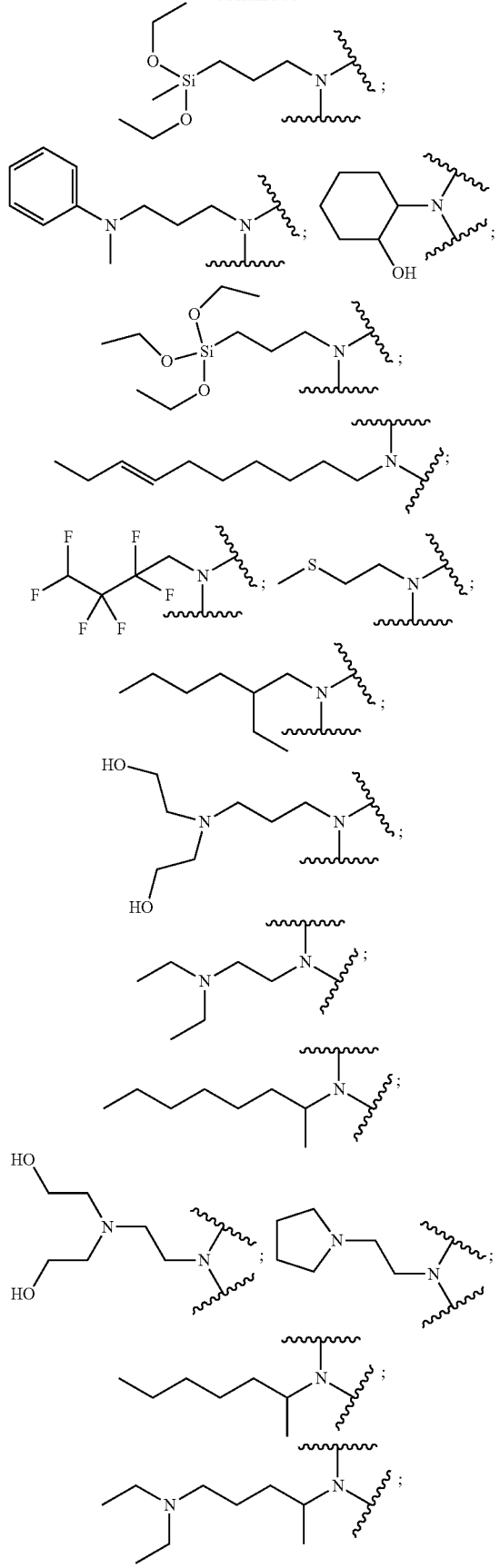
38
-continued
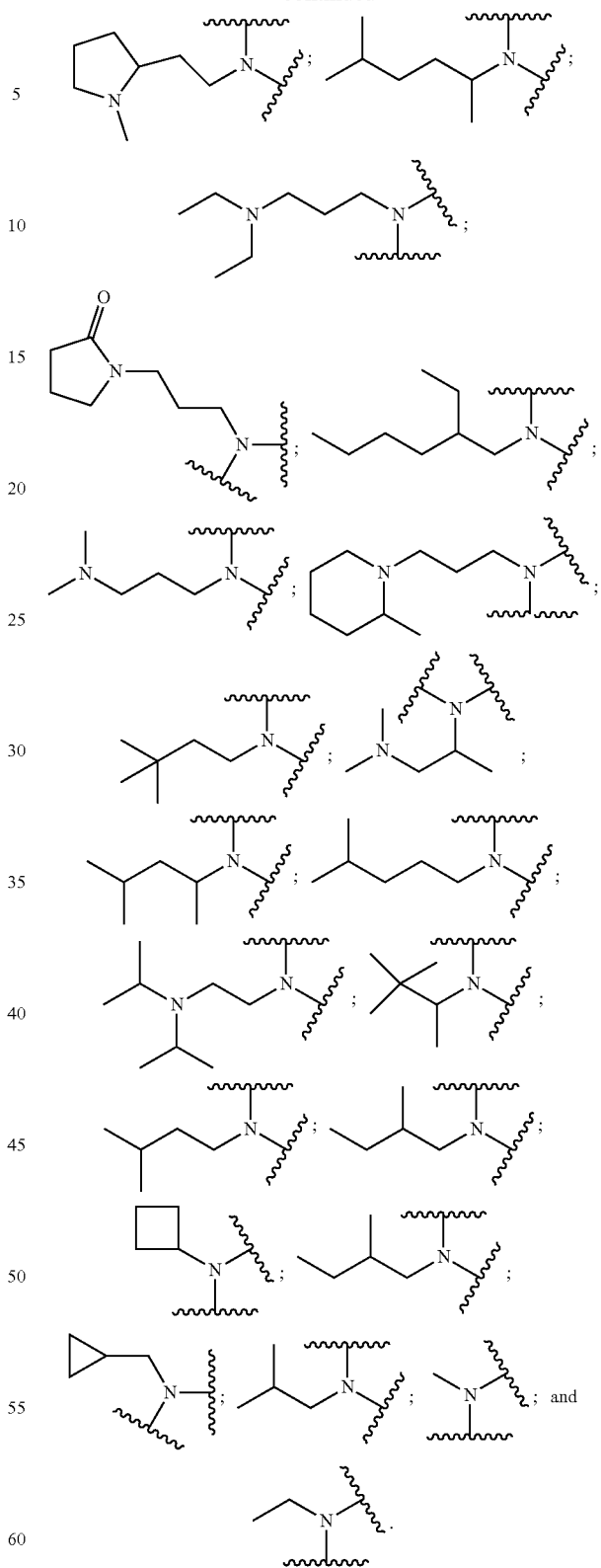
Variable B
Variable B is a divalent radical derived from a di-acrylate monomer. In polymers of Formula (I), each B independently is $B_1$, $B_2$, or $B_3$, wherein:

B₁ is

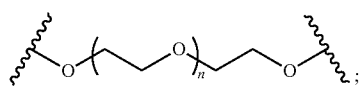

wherein n is 0-100;

B₂ is

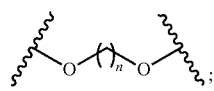

wherein n is 2-100; and

B₃ is

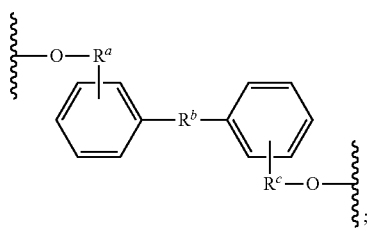

wherein $R^a$, $R^b$, and $R^c$ independently are selected from optionally substituted alkylene, optionally substituted alkenylene, optionally substituted alkynylene, optionally substituted heteroalkylene, optionally substituted cycloalkylene, and optionally substituted heterocyclylene.

In certain embodiments, $R^a$ and $R^c$ are the same. In certain embodiments, $R^a$ and $R^c$ are alkyl or heteroalkyl. In certain particular embodiments, $R^a$ and $R^c$ are alkyloxyl, such as polyethoxyl. In certain embodiments, $R^a$ and $R^c$ are unsubstituted. In certain embodiments, $R^a$ and $R^c$ are substituted one or more times.

In certain embodiments, $R^b$ is a heteroatom (e.g., oxygen or nitrogen). In certain embodiments, $R^b$ is alkyl or heteroalkyl. In certain embodiments, $R^b$ is unsubstituted methylene (i.e., CH₂) or substituted methylene (e.g., C(CH₃)₂).

In certain embodiments, variable B is selected from:

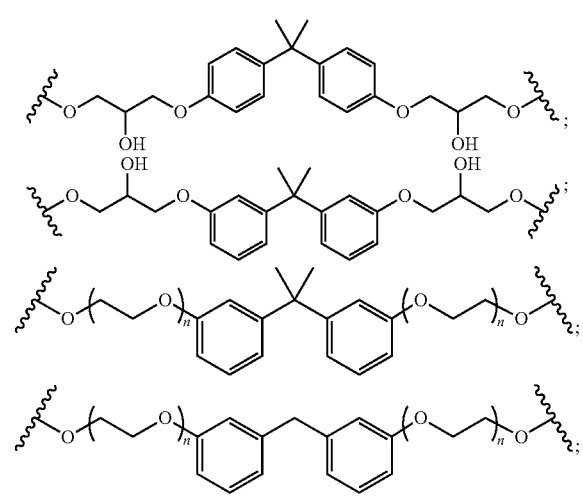

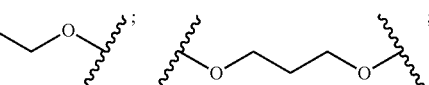

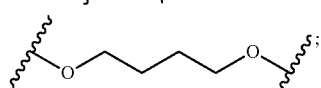

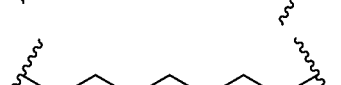

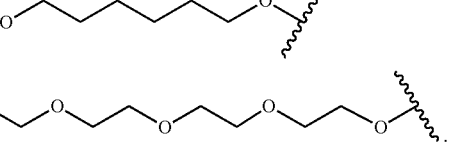

When present, n is 1-100. In certain embodiments, n is 1-10. In certain embodiments, n is 1-5.

Variable D

Variable D is a monovalent radical comprising a primary amine group. each D independently is $D_1$, $D_2$, $D_3$, or $D_4$, wherein:

$D_1$ is

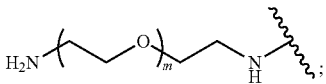

$D_2$ is

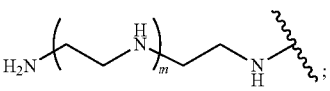

$D_3$ is

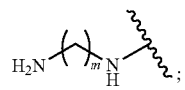

and $D_4$ is

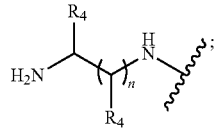

wherein each $R_4$ independently is hydrogen, halogen, hydroxyl, alkyl, or heteroalkyl. When present, m is 0 to 20. When present, n is 1-10.

In certain embodiments, D is selected from:

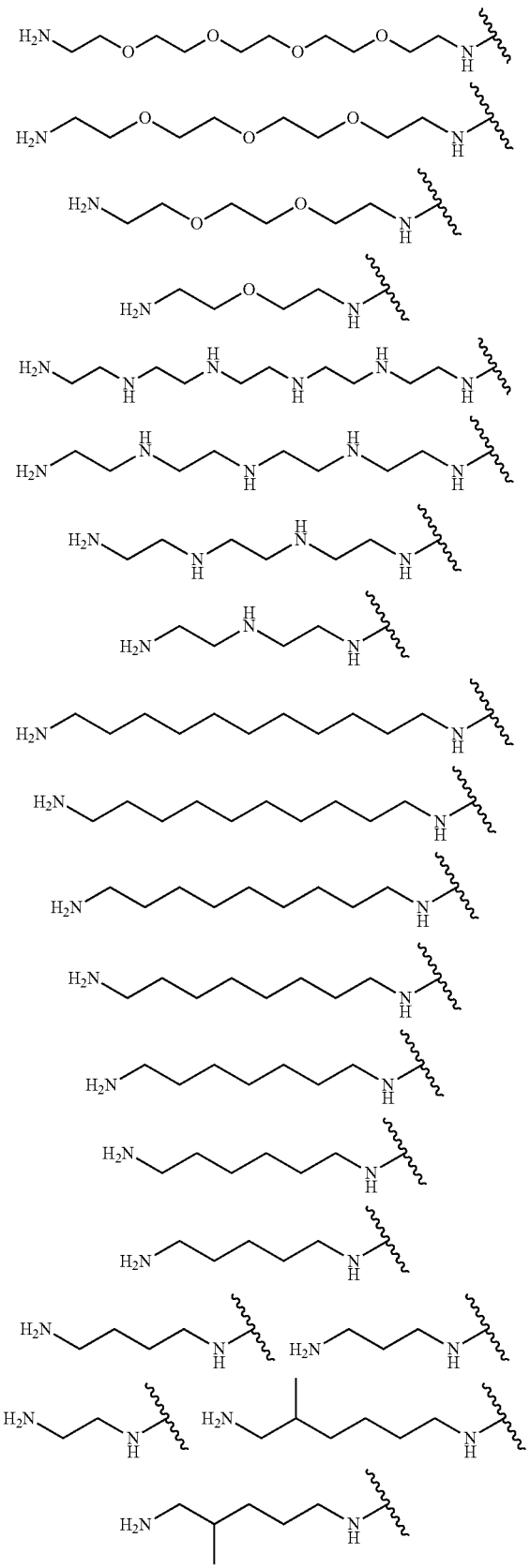

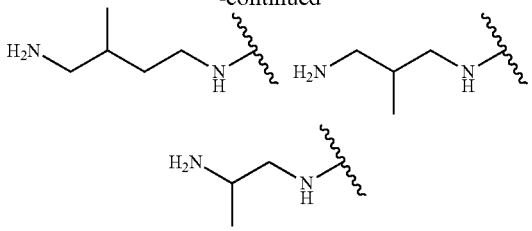

In certain embodiments, D is selected from:

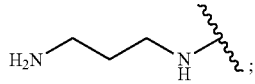
(1)

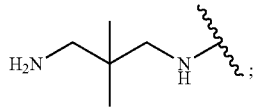
(2)

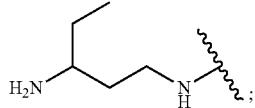
(3)

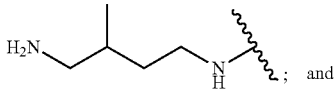
; and (4)

(5)

[structure 5]

Variable R

Variable R is a monovalent radical. Each R may be the same or different. In certain embodiments, each R is the same. In certain embodiments, R is alkyl. In certain embodiments, R is hydrogen.

Molecular Weight

Polymers of Formula (I) may be prepared or used as described in WO 2002/031025, WO 2004/106411, and WO 2008/011561, the entire contents of which are incorporated by reference.

Molecular weight is influenced by the molar ratio of diacrylate monomer (corresponding to the diradical B) to the amine monomers corresponding to diradicals $A_1$ and $A_2$. A higher molar ratio of diacrylate monomer to amine monomers will lead to lower molecular weight. A B:A molar ratio of about 1 will lead to greater molecular weight.

In certain embodiments, polymers of formula (I) have a molecular weight in the range of 1-100 kDa, 5-50 kDa, 10-40 kDa, or 15-30 kDa. In certain embodiments, the polymers of the invention have a molecular weight in the range of 15-24 kDa. In certain particular embodiments, the polymers of the invention have a molecular weight of about 15 kDa, about 16 kDa, about 17 kDa, about 18 kDa, about 19 kDa, about 20 kDa, about 21 kDa, about 22 kDa, about 23 kDa, or about 24 kDa.

Biodegradability and Biocompatibility

In certain embodiments, the polymers of the invention are biodegradable or biocompatible. As used herein, "biodegradable" polymers are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain embodiments, the chemical reactions relied upon to break down the biodegradable polymers are uncatalyzed. Biodegradability is a particular advantage of these PBAE delivery vectors, particularly for repeat administration where non-degradable vectors like PEI may accumulate or be difficult for the body to metabolize. The term "biocompatible," as used herein is intended to describe compounds that are not toxic to cells. Polymers are "biocompatible" if their addition to cells in vitro results in less than or equal to 20% cell death, and their administration in vivo does not induce inflammation or other such adverse effects.

Compositions

The present invention contemplates a polymer of the invention, e.g., a polymer of Formula (I), as a component of a composition. For example, in certain embodiments, provided is a composition comprising a polymer of the invention, or salt thereof, and optionally an excipient.

PEG Lipids

In certain embodiments, the composition further comprises a PEG lipid. In some embodiments, the PEG lipid is a PEG-diacylglycerol (DAG), a PEG-dialkyloxypropyl (DAA), a PEG-phospholipid, a PEG-ceramide (Cer), or a mixture thereof. In some embodiments, PLGA is conjugated to a lipid-terminating PEG forming PLGA-DSPE-PEG. In some embodiments, a PEG lipid is selected from PEG-c-DOMG and 1,2-Dimyristoyl-sn-glycerol, methoxypolyethylene Glycol (PEG-DMG), 1,2-Distearoyl-sn-glycerol, methoxypolyethylene Glycol (PEG-DSG), PEG-c-DOMG, 1,2-Distearoyl-sn-glycerol, methoxypolyethylene glycol (PEG-DSG) 1,2-Dipalmitoyl-sn-glycerol, methoxypolyethylene glycol (PEG-DPG), PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates, polyamide oligomers (e.g., ATTA-lipid conjugates), and mixtures thereof. In some embodiments, the PEG is a PEG-dilauryloxypropyl (C12), a PEG-dimyristyloxypropyl (C14), a PEG-dipalmityloxypropyl (C16), a PEG-distearyloxypropyl (C18), PEG-c-DOMG, PEG-DMG, or a mixture thereof.

In certain embodiments, the PEG lipid is a PEGylated fatty acid. Representative fatty acids comprise carbon chains of 8-26 carbon atoms. In certain embodiments, the fatty acids comprise carbon chains of 8-18 carbon atoms. In certain particular embodiments, the PEGylated fatty acid comprises a carbon chain having 18 carbon atoms.

The PEG lipid comprises one or more PEG (polyethylene glycol) chains. In certain embodiments the PEG lipid has one or two PEG chains. In a particular embodiment, the PEG lipid has one PEG chain. In certain embodiments, the PEG has an average molecular weight in the range of 1000-5000 Da. In certain embodiments, the PEG has an average molecular weight in the range of 1000-3000 Da. In certain embodiments, the PEG has an average molecular weight of 2000 Da. In a particular embodiment, the PEG lipid is C18-PEG2000.

The PEG lipid is present in compositions described herein in the amount of 1-10 mol % with reference to the polymer (i.e., the polymer represents 100 mol %). In certain embodiments, the PEG lipid is present in the amount of 1-5 mol %.

Steroids

Compositions, as described herein, may further comprise a steroid. In certain embodiments, the steroid is cholesterol or a cholesterol derivative. In certain embodiments, the composition does not contain a steroid. When present, the steroid is present in the amount of 1-50 mol % with reference to the polymer.

Phospholipids

Compositions, as described herein, may further comprise a phospholipid. The phospholipid is present in compositions described herein in the amount of 1-50 mol % with reference to the polymer. In certain embodiments, the phospholipid is present in the amount of 20-50 mol %. In certain embodiments, the phospholipid is present in the amount of 20 mol %.

The structure of the phospholipid molecule generally consists of two hydrophobic fatty acid "tails" and a hydrophilic "head" consisting of a phosphate group. The two components are joined together by a glycerol molecule. The phosphate groups can be modified with simple organic molecules such as choline, ethanolamine or serine. In certain embodiments, the phospholipid is selected from distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 1-stearoyl-2-oleoyl-phosphatidyethanolamine (SOPE), phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, and palmitoyloleyolphosphatidylglycerol (POPG). In a particular embodiment, the phospholipid is DOPE.

Agents

Compositions, as described herein, may further comprise one or more agents. The agent may be a therapeutic, diagnostic, or prophylactic agent. The agent may be an organic molecule, inorganic molecule, nucleic acid, protein, peptide, polynucleotide, targeting agent, an isotopically labeled chemical compound, vaccine, or an immunological agent In certain embodiments, the agents are organic compounds with pharmaceutical activity. In another embodiment of the invention, the agent is a clinically used drug (e.g., a drug approved in the United States by the FDA or in Europe by the EMA). In certain embodiments, the drug is an antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, nutritional agent, etc.

In certain embodiments, the agent to be delivered is a mixture of agents. The mixture may include 2-10 agents. For example, the mixture may include 2, 3, 4, 5, 6, 7, 8, 9 or 10 agents.

Polynucleotides

In certain embodiments, compositions as described herein comprise a polynucleotide. The polynucleotide may be any nucleic acid including, but not limited to, RNA and DNA.

In certain embodiments, the polynucleotide is DNA. In certain particular embodiments, the DNA is genomic DNA, synthetic DNA, a synthetic analog of DNA, cDNA or a DNA/RNA hybrid.

In certain embodiments, the polynucleotide is RNA. In certain embodiments, the polynucleotide is mRNA, siRNA, ssRNA, dsRNA, shRNA, miRNA. In certain particular embodiments, the polynucleotide is mRNA.

In certain embodiments, the polynucleotide is an RNA that carries out RNA interference (RNAi). The phenomenon of RNAi is discussed in greater detail, for example, in the following references, each of which is incorporated herein by reference: Elbashir et al., 2001, *Genes Dev.,* 15:188; Fire et al., 1998, *Nature,* 391:806; Tabara et al., 1999, *Cell,* 99:123; Hammond et al., *Nature,* 2000, 404:293; Zamore et al., 2000, *Cell,* 101:25; Chakraborty, 2007, *Curr. Drug Targets,* 8:469; and Morris and Rossi, 2006, *Gene Ther.,* 13:553.

In certain embodiments, the polynucleotide is a dsRNA (double-stranded RNA).

In certain embodiments, the polynucleotide is an siRNA (short interfering RNA).

In certain embodiments, the polynucleotide is an shRNA (short hairpin RNA).

In certain embodiments, the polynucleotide is an miRNA (micro RNA). Micro RNAs (miRNAs) are genomically encoded non-coding RNAs of about 21-23 nucleotides in length that help regulate gene expression, particularly during development (see, e.g., Bartel, 2004, *Cell,* 116:281; Novina and Sharp, 2004, *Nature,* 430:161; and U.S. Patent Publication 2005/0059005; also reviewed in Wang and Li, 2007, *Front. Biosci.,* 12:3975; and Zhao, 2007, *Trends Biochem. Sci.,* 32:189; each of which are incorporated herein by reference).

In certain embodiments, the polynucleotide is an antisense RNA.

In some embodiments, an RNA can be designed and/or predicted using one or more of a large number of available algorithms. To give but a few examples, the following resources can be utilized to design and/or predict dsRNA, siRNA, shRNA and/or miRNA: algorithms found at Alnylum Online, Dharmacon Online, OligoEngine Online, Molecula Online, Ambion Online, BioPredsi Online, RNAi Web Online, Chang Bioscience Online, Invitrogen Online, LentiWeb Online GenScript Online, Protocol Online; Reynolds et al., 2004, *Nat. Biotechnol.,* 22:326; Naito et al., 2006, *Nucleic Acids Res.,* 34:W448; Li et al., 2007, *RNA,* 13:1765; Yiu et al., 2005, *Bioinformatics,* 21:144; and Jia et al., 2006, *BMC Bioinformatics,* 7: 271; each of which is incorporated herein by reference).

The polynucleotide may be of any size or sequence, and may be single- or double-stranded. In certain embodiments, the polynucleotide is greater than 100 base pairs long. In certain embodiments, the polynucleotide is greater than 1000 base pairs long and may be greater than 10,000 base pairs long. The polynucleotide is optionally purified and substantially pure. Preferably, the polynucleotide is greater than 50% pure, more preferably greater than 75% pure, and most preferably greater than 95% pure. The polynucleotide may be provided by any means known in the art. In certain embodiments, the polynucleotide has been engineered using recombinant techniques (for a more detailed description of these techniques, please see Ausubel et al. *Current Protocols in Molecular Biology* (John Wiley & Sons, Inc., New York, 1999); *Molecular Cloning: A Laboratory Manual,* 2nd Ed., ed. by Sambrook, Fritsch, and Maniatis (Cold Spring Harbor Laboratory Press: 1989); each of which is incorporated herein by reference). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry.

The polynucleotide may be modified by chemical or biological means. In certain embodiments, these modifications lead to increased stability of the polynucleotide. Modifications include methylation, phosphorylation, end-capping, etc.

Derivatives of polynucleotides may also be used in the present invention. These derivatives include modifications in the bases, sugars, and/or phosphate linkages of the polynucleotide. Modified bases include, but are not limited to, those found in the following nucleoside analogs: 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugars include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in this art, the modified polynucleotides are preferably prepared using synthetic chemistry in vitro.

The polynucleotide may be in any form. For example, the polynucleotide may be a circular plasmid, a linearized plasmid, a cosmid, a viral genome, a modified viral genome, an artificial chromosome, etc.

The polynucleotide may be of any sequence. In certain embodiments, the polynucleotide encodes a protein or peptide. The encoded proteins may be enzymes, structural proteins, receptors, soluble receptors, ion channels, pharmaceutically active proteins, cytokines, interleukins, antibodies, antibody fragments, antigens, coagulation factors, albumin, growth factors, hormones, insulin, etc. The polynucleotide may also comprise regulatory regions to control the expression of a gene. These regulatory regions may include, but are not limited to, promoters, enhancer elements, repressor elements, TATA box, ribosomal binding sites, stop site for transcription, etc. In certain embodiments, the polynucleotide is not intended to encode a protein. For example, the polynucleotide may be used to fix an error in the genome of the cell being transfected.

The polynucleotide may also be provided as an antisense agent or RNA interference (RNAi) agent (Fire et al. *Nature* 391:806-811, 1998; incorporated herein by reference). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular mechanisms of action of antisense drugs" *Biochim. Biophys. Acta* 1489(1): 31-44, 1999; Crooke "Evaluating the mechanism of action of antiproliferative antisense drugs" *Antisense Nucleic Acid Drug Dev.* 10(2):123-126, discussion 127, 2000; *Methods in Enzymology* volumes 313-314, 1999; each of which is incorporated herein by reference). The binding may be by conventional base pair complementarity, or, for example, in the case of binding to DNA duplexes, through specific interactions in the major groove of the double helix (i.e., triple helix formation) (Chan et al. *J. Mol. Med.* 75(4):267-282, 1997; incorporated herein by reference).

Compositions of the invention comprising an agent, wherein the agent is a polynucleotide, may be characterized in terms of an N/P ratio (i.e., the ratio of moles of the amine groups of the polymer of the invention to moles of the phosphate groups of the polynucleotide). In certain embodiments, the N/P ratio of compositions of the invention is in the range of 1-100, 25-100, 50-100, 50-75, 25-75, and 25-50. In a particular embodiment, compositions of the invention comprising a polynucleotide agent are characterized by an N/P ratio of 50.

Particles

The polymers of the present invention are useful as drug delivery vehicles. The polymers may be used to encapsulate agents including polynucleotides, small molecules, proteins, peptides, metals, organometallic compounds, etc. The polymers have several properties that make them particularly suitable in the preparation of drug delivery vehicles. These include: 1) the ability of the lipid to complex and "protect" labile agents; 2) the ability to buffer the pH in the endosome; 3) the ability to act as a "proton sponge" and cause endosomolysis; and/or 4) the ability to neutralize the charge on negatively charged agents. In certain embodiments, the polymers are used to form particles containing the agent to be delivered. These particles may include other materials, such as steroids (e.g., cholesterol), proteins, carbohydrates, synthetic polymers (e.g., PEG, PLGA), lipids, and natural polymers.

In certain embodiments, the particle is a microparticle or a nanoparticle. In certain embodiments, the diameter of the particles range from between 1 micrometer to 1,000 micrometers. In certain embodiments, the diameter of the particles range from between from 1 micrometer to 100 micrometers. In certain embodiments, the diameter of the particles range from between from 1 micrometer to 10 micrometers. In certain embodiments, the diameter of the particles range from between from 10 micrometer to 100 micrometers. In certain embodiments, the diameter of the particles range from between from 100 micrometer to 1,000 micrometers. In certain embodiments, the particles range from 1-5 micrometers. In certain embodiments, the diameter of the particles range from between 1 nm to 1,000 nm. In certain embodiments, the diameter of the particles range from between from 1 nm to 100 nm. In certain embodiments, the particles range from 1-5 nm. In certain embodiments, the diameter of the particles range from between from 1 nm to 10 nm. In certain embodiments, the diameter of the particles range from between from 10 nm to 100 nm. In certain embodiments, the diameter of the particles range from between from 100 nm to 1,000 nm. In certain embodiments, the diameter of the particles is greater than 300 nm, e.g., between 300-400 nm, 300-500 nm, 300-600 nm, 300-700 nm, 300-800 nm, 300-900 nm, or 300-1000 nm. In certain embodiments, the diameter of the particles range from between 1 pm to 1,000 pm. In certain embodiments, the diameter of the particles range from between from 1 pm to 100 pm. In certain embodiments, the diameter of the particles range from between from 1 pm to 10 pm. In certain embodiments, the diameter of the particles range from between from 10 pm to 100 pm. In certain embodiments, the diameter of the particles range from between from 100 pm to 1,000 pm. In certain embodiments, the particles range from 1-5 pm. If the particles prepared by any of the above methods have a size range outside of the desired range, the particles can be sized, for example, using a sieve.

In some embodiments, particles of a composition as described herein comprise an agent, and the percentage of the particles that comprise an agent is between about 1 and about 100% (e.g., about 1%, about 2%, about 3%, about 4%, about 5%, about 10%, about 15%, about 20%, about 30%, about 40%, about 50%, about 60%, about 70%, about 80%, about 90%, or about 100%). In some embodiments, the percentage of the particles that comprise an agent is less than about 50%, e.g., less than about 40%, less than about 35%, less than about 30%, less than about 25%, less than about 20%, less than about 15%, or less than about 10%. In some embodiments, the percentage of the particles that comprise an agent is between about 5% and about 50%, about 5% and about 40%, about 5% and about 30%, about 5% and about 25%, or about 5% and about 20%. In some embodiments, the percentage of the particles that comprise an agent is between about 5% and 90%. In some embodiments, the percentage of the particles that comprise an agent is between about 5% and about 75%. In the some embodiments, the percentage of particles that comprise an agent is between about 5% and about 50%. In the some embodiments, the percentage of the particles that comprise an agent is between about 10% and about 25%.

In some embodiments, the total amount of the agent present in the particle is greater than about 5% (e.g., about 6%, about 7%, about 8%, about 9%, about 10%, about 12%, about 15%, about 20%, about 25%, about 30%, or more) of the total size or weight of the conjugate or particle. In some embodiments, the total amount of the agent present in the conjugate or particle is greater than about 10% (e.g., about 12%, about 15%, about 20%, about 25%, about 30%, or more) of the total size or weight of the conjugate or particle.

Without being bound by theory, the polymers or particles disclosed herein may improve the efficiency of an agent by one or more of increasing the localization and/or release (e.g., preferential release) of the agent to a target cell (e.g., a cancer or a fibrotic cell; a cell associated with a hypoxic environment), or increasing the half-life of the agent, thus resulting in a significantly higher amount of a released agent at a target site (e.g., a tumor or liver (e.g., cirrhotic cell). According, the conjugates and particles disclosed herein can be more effective therapeutically than the free agent (e.g., due to enhanced drug uptake in the target tissue) and/or allow for a lower therapeutic dose of the agent, e.g., without substantially compromising the resulting drug concentration at a target tissue. In some embodiments, the conjugates and particles disclosed herein can reduce the adverse effect associated with systemic administration of an agent in free form (e.g., not coupled to a polymer, conjugate or particle described herein).

Without being bound by theory, due to the localized delivery of the compositions described herein (e.g., the agent-containing particles), a lower dose or amount of the agent in the particles can be administered (e.g., through local sustained delivery) compared to the agent in free form. In other embodiments, the agent-containing particles are administered at a dose or amount of the agent that is less than the dose or amount of said agent in free form to have a desired effect (e.g., a desired therapeutic effect).

In some embodiments, the agent is incorporated into a particle at a dose that is less than the dose or amount of said agent in free form to have a desired effect (e.g., a desired therapeutic effect), e.g., the standard of care dose for the intended use of the free agent. In one embodiment, the agent are incorporated into the particles at a dose or amount of the agent that is less than the standard of care dose of the agent for a desired therapy (e.g., a dose that is less than about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, or about 0.95 that of the standard of care dose of the agent).

In some embodiments, the agent is incorporated into a particle at a dose equivalent to the dose or amount of said agent in free form to have a desired effect (e.g., a desired therapeutic effect), e.g., the standard of care dose for the intended use of the free agent. In these embodiments, the particle produces a greater therapeutic effect and/or a less adverse effect than the free agent. In certain embodiments, the particle increases the amount of the agent delivered to a tissue or cell in need thereof and reduces the amount of the agent exposed to a non-target tissue or cell, as compared to the free agent.

In some embodiments, the agent is incorporated into a particle at a dose higher than the dose or amount of said agent in free form to have a desired effect (e.g., a desired therapeutic effect), e.g., the standard of care dose for the intended use of the free agent. In some embodiments, the agent is incorporated into a particle at a dose higher than the dose or amount of said agent in free form that would produce an adverse effect by systemic administration (e.g., a reduction in blood pressure). In some embodiments, since the particle described herein releases the agent at a target site based on pH microenvironment, other non-target sites (e.g., blood vessels) with different pH would be less likely to be exposed to the agent.

Methods of Preparing Particles

Particles comprising polymers of the invention may be prepared using any method known in the art. These include, but are not limited to, lyophilization, spray drying, single and double emulsion solvent evaporation, solvent extraction, phase separation, simple and complex coacervation, and other methods well known to those of ordinary skill in the art. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, etc.). The method of preparing the particle and the conditions (e.g., solvent, temperature, concentration, air flow rate, etc.) used may also depend on the agent being encapsulated and/or the composition of the matrix.

Methods developed for making particles for delivery of encapsulated agents are described in the literature (for example, please see Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al. *Reactive Polymers* 6:275-283, 1987; Mathiowitz et al. *J. Appl. Polymer Sci.* 35:755-774, 1988; each of which is incorporated herein by reference).

In certain embodiments, the particle is produced by lyophilization. In certain embodiments, the lyophilized particle retains at least about 20%, at least about 30%, at least about 40%, at least about 50%, at least about 60%, at least about 70%, at least about 80%, or at least about 90% efficacy after storage for 14-90 days at −80° C.

Compositions, as described herein, may be useful in a variety of medical and non-medical applications. For example, pharmaceutical compositions comprising a polymer of the invention and an excipient may be useful in the delivery of an effective amount of an agent to a subject in need thereof. Nutraceutical compositions comprising a polymer of the invention and an excipient may be useful in the delivery of an effective amount of a nutraceutical, e.g., a dietary supplement, to a subject in need thereof. Cosmetic compositions comprising a polymer of the invention and an excipient may be formulated as a cream, ointment, balm, paste, film, or liquid, etc., and may be useful in the application of make-up, hair products, and materials useful for personal hygiene, etc.

The composition may comprise one type of polymer of the invention but may also comprise any number of different types, e.g., 1, 2, 3, 4, 5, 6, 7, 8, 9, 10 or more different types of polymers of the invention.

Accordingly, provided herein in another aspect is a composition comprising a polymer of the invention, e.g., a polymer of Formula (I). In certain embodiments, the composition is a cosmetic composition. In certain embodiments, the composition is a pharmaceutical composition and further comprises a pharmaceutically acceptable carrier.

Pharmaceutical Compositions

Compositions as described herein may be combined with one or more pharmaceutical excipients to form a pharmaceutical composition that is suitable to administer to animals including humans. As would be appreciated by one of skill in this art, the excipients may be chosen based on the route of administration as described below, the agent being delivered, time course of delivery of the agent, etc.

Pharmaceutical compositions of the present invention and for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

These and other aspects of the present invention will be further appreciated upon consideration of the following Examples, which are intended to illustrate certain particular embodiments of the invention but are not intended to limit its scope, as defined by the claims.

Methods

In certain aspects, provided herein is a method of treating a disease, disorder, or condition from which a subject suffers, comprising administering to the subject in need thereof an effective amount of a composition as described herein. In certain embodiments, the disease, disorder, or condition is selected from the group consisting of proliferative disorders, inflammatory disorders, autoimmune disorders, painful conditions, and diseases of the lung, spleen, and liver. In certain embodiments, the disease, disorder or condition from which a subject suffers is caused by an abnormality in a gene or chromosome of the subject.

In certain embodiments, the method is for treating lung disease. In certain particular embodiments, the lung disease is asthma, chronic obstructive pulmonary disease (COPD), chronic bronchitis, emphysema, pulmonary hypertension, pulmonary fibrosis (e.g., idiopathic pulmonary fibrosis, fibrotic interstitial lung disease, interstitial pneumonia, fibrotic variant of non-specific interstitial pneumonia, or cystic fibrosis), sarcoidosis, influenza, pneumonia, tuberculosis, or lung cancer. In certain embodiments, the lung cancer is bronchogenic carcinoma, small cell lung cancer (SCLC), non-small cell lung cancer (NSCLC), or adenocarcinoma of the lung.

In certain embodiments, the composition further comprises, in addition to the polymer of the invention, a therapeutic agent useful in treating the disease, disorder, or condition. In certain embodiments, the polymer of the invention encapsulates the other (therapeutic) agent. In certain embodiments, the polymer of the invention and the other (therapeutic) agent form a particle (e.g., a nanoparticle, a microparticle, a micelle, a liposome, a lipoplex).

In certain embodiments, the condition is a proliferative disorder and, in certain embodiments, the composition further includes an anti-cancer agent. Anti-cancer agents encompass biotherapeutic anti-cancer agents as well as chemotherapeutic agents.

In certain embodiments, the condition is an inflammatory disorder and, in certain embodiments, the composition further includes an anti-inflammatory agent. In certain embodiments, the inflammatory disorder is inflammation associated with a proliferative disorder, e.g., inflammation associated with cancer.

In certain embodiments, the condition is an autoimmune disorder and, in certain embodiments, the composition further includes an immunomodulatory agent.

In certain embodiments, the condition is a painful condition and, in certain embodiments, the composition further includes an analgesic agent.

In certain embodiments, the painful condition is inflammatory pain. In certain embodiments, the painful condition (e.g., inflammatory pain) is associated with an inflammatory disorder and/or an autoimmune disorder.

In certain embodiments, the condition is a liver disease and, in certain embodiments, the composition further includes an agent useful in treating liver disease.

Administration

Compositions as described herein may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. Compositions are preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the composition described herein is suitable for topical administration to the eye of a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a polymer described herein. In certain embodiments, a dose described herein includes independently between 1 mg and 3 mg, inclusive, of a polymer described herein. In certain embodiments, a dose described herein includes independently between 3 mg and 10 mg, inclusive, of a polymer described herein. In certain embodiments, a dose described herein includes independently between 10 mg and 30 mg, inclusive, of a polymer described herein. In certain embodiments, a dose described herein includes independently between 30 mg and 100 mg, inclusive, of a polymer described herein.

Dose ranges as described herein provide guidance for the administration of provided compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

The composition can be administered concurrently with, prior to, or subsequent to one or more additional agents, which are different from the composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the polymer or composition described herein in a single dose or administered separately in different doses. The particular combination to employ in a regimen will take into account compatibility of the polymer described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

Formulated, Biodegradable Polymeric Nanoparticles for Nucleic Acid Delivery

A key feature of PBAE synthesis is its relative simplicity. The reaction proceeds through the Michael addition of an amine to a diacrylate under mild conditions with high conversion.[25] PBAE terpolymers incorporate an additional alkylamine in the backbone.[26] Previous studies seeking to optimize PBAE nanoparticles have focused on the synthesis of libraries using a diverse set of monomers,[27,28] and altering polymer end-capping[29], molecular weight[30], and alkylamine chain length (in the case of terpolymers)[26]. The simultaneous evaluation of such synthesis parameters was investigated in the context of a single diacrylate/amine pair. Specifically, the end capping group, the length of the alkylamine carbon chain, the molar ratio of diacrylate to amines (alters the molecular weight[31]), and the molar ratio of the alkylamine to 4-(2-amino methyl) morpholine (Table 1) were varied. The diacrylate and amine chosen for this purpose, bisphenol A glycerolate and 4-(2-amino methyl) morpholine, respectively (FIG. 1A), were identified as efficacious in previous studies of terpolymers[26] and were the most effective in vivo following formulation with mRNA and PEG-lipid[24].

Because previous studies demonstrated that co-formulating polymer-nucleic particles with PEG-lipid can enhance function, the utility of PEG-lipids was explored with the materials developed here.[24] Formulation of PEG-lipid with nucleic acid and these materials requires the use of two phases: an organic phase (ethanol) to dissolve the polymer and PEG-lipid, and an acidic aqueous phase (sodium acetate buffer, 25 mM). These phases must be mixed and then dialyzed against PBS to remove organic solvent and to reach physiological pH. This extra processing makes traditional methods of high-throughput particle synthesis less practical. Thus, instead of performing a full-factorial screen, experimental design was utilized in order to reduce the number of polymers/formulations necessary to explore the design space including all of the variables of interest. This statistical method was previously utilized to optimize lipid nanoparticle formulations[17], but had not before been applied to PBAE synthesis. To this end, JMP software was utilized to design a partial factorial screen of 30 polymers (Table 2) within the parameter space detailed in Table 1. Polymers were synthesized according to a previously reported protocol.[24] Briefly, diacrylate and amine monomers were dissolved in N,N-dimethylformamide with an excess of diacrylate and the step polymerization was allowed to proceed for 48 hours at 90° C. Following polymerization, an excess of end-capping monomer was added and reacted at room temperature for 24 hours. The polymer was then purified via excess monomer removal by multiple washes in diethyl ether.

Figure 2:
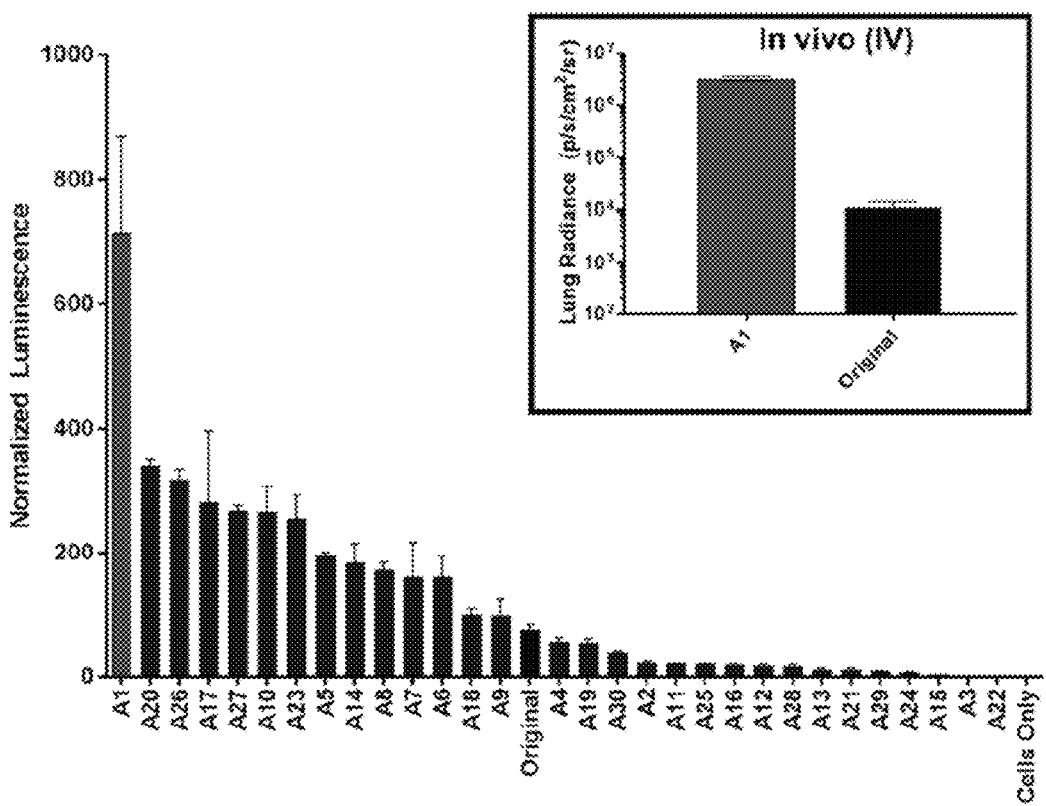
FIG. 2. A partial factorial screen for optimizing PBAE synthesis parameters reveals several polymers more potent than the original when delivered in vitro in HeLa cells (n=4). The top-performing polymer, A1, is two orders of magnitude more potent in vivo in mouse lungs after IV delivery than the original, corresponding well to the in vitro results (n=3). All particles were synthesized with luciferase-coding mRNA at an N/P of 57 with 7 wt % C14-PEG2000 PEG-lipid.[32]

For formulation, polymers were dissolved in DMSO at 100 mg/mL, and the resulting solution was co-dissolved in ethanol with 7 wt % PEG-lipid, mixed with an equal volume of luciferase-encoding mRNA diluted in 25 mM sodium acetate buffer by pipetting, and dialyzed against PBS. The resulting nanoparticles were used to transfect HeLa cells (0.2 ng/μL mRNA dose), which were assayed for luminescence 24 hours following transfection. As can be seen in FIG. 2, several polymers were more potent than the original polymer, with the top-performing variant, referred to hereafter as A1 (FIG. 2), over two orders of magnitude more effective than the original. Importantly, this difference was also observed in vivo (FIG. 2), suggesting that in terms of relative efficacy, this in vitro screen recapitulated in vivo results. The statistical model generated showed that the end cap had the only statistically significant effect on efficacy (FIGS. 6A-6D), with end cap 1, the end cap used in A1, having the strongest positive correlation with efficacy. End-cap screening alone has already been performed for a large set of PBAE materials[29] and demonstrated that the 5 used herein are the most effective and as such subsequent synthesis screens were not performed. However, even without subsequent optimization, the potency of the polymer was improved using only a fraction of the available design space, demonstrating the power of experimental design for the rapid optimization of PBAE synthesis.

Figure 1B:
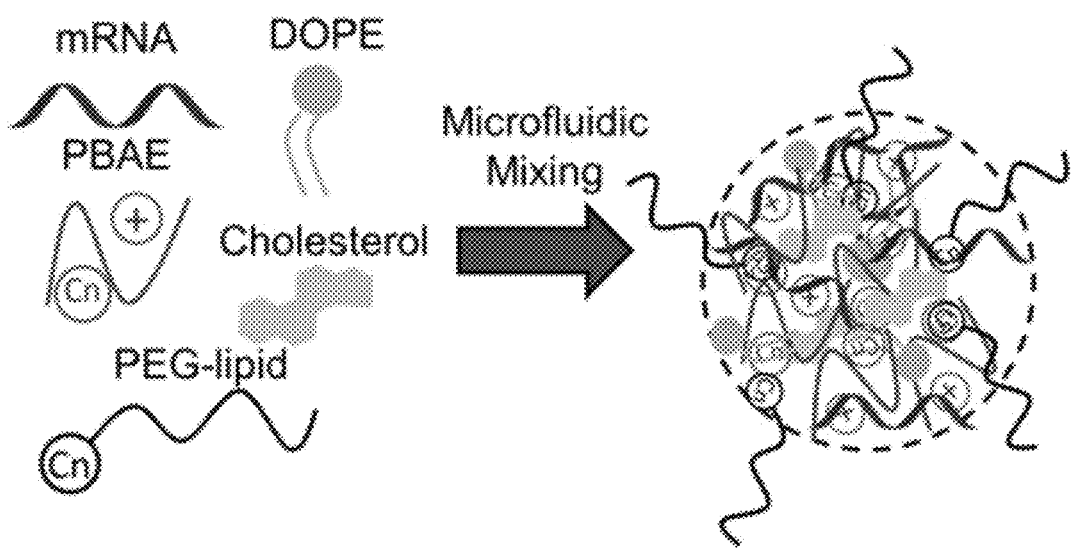

In addition to optimizing the polymer synthesis, the nanoparticle formulation, which has been shown to have a significant effect on mRNA delivery[17], was also optimized. Because the effects of formulation, such as changes in serum stability or biodistribution[24], are not always identifiable in vitro, formulation screens were performed in vivo. The improvements in delivery through non-covalent formulation of PBAE terpolymers with PEG-lipid[26,32] suggest that incorporation of other hydrophobic moieties may also improve function. As such, lipid nanoparticle formulation strategies were adapted for use with PBAE materials. In particular, the utility of 1,2-dioleoyl-sn-glycero-3-phosphoethanolamine (DOPE) and cholesterol when co-formulated with PBAE polymers were investigated.[17] In addition, polymer N/P ratio, the PEG MW in the PEG-lipid, the phospholipid length in the PEG-lipid, and the molar composition of PEG-lipid in the formulation (FIG. 1B) were altered.

Figure 3A:
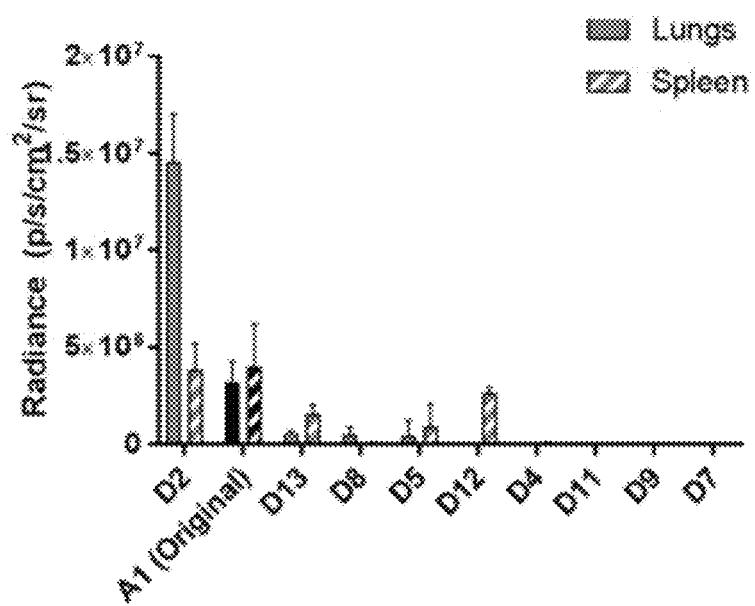
FIGS. 3A-3D. Luciferase-encoding mRNA was delivered via A1 PBAE nanoparticles intravenously in mice, and luminescence in various organs was assessed at 24 hours.
Figure 16A:
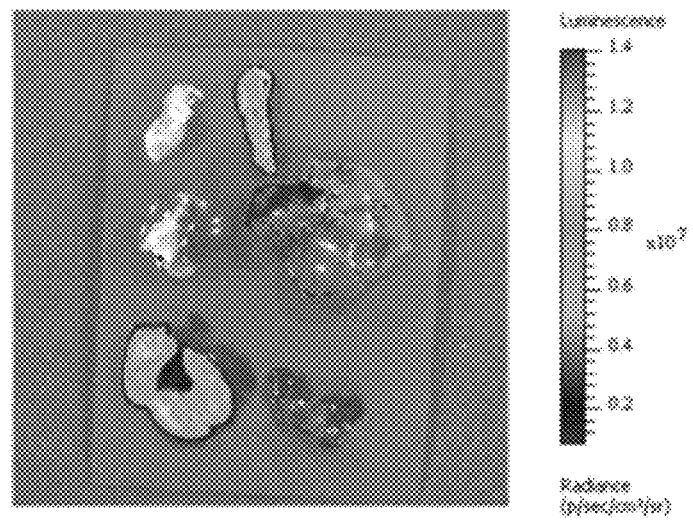
FIGS. 16A-16C. Representative luminescent images showing distribution of mRNA translation 24 hours following IV administration of control A1 particles formulated with 7 mol % C14-PEG2000 (FIG. 16A), optimized A1-L3 particles (FIG. 16B), and in vivo jetPEI (FIG. 16C). All particles administered at 0.5 mg/kg mRNA dose.
Figure 16B:
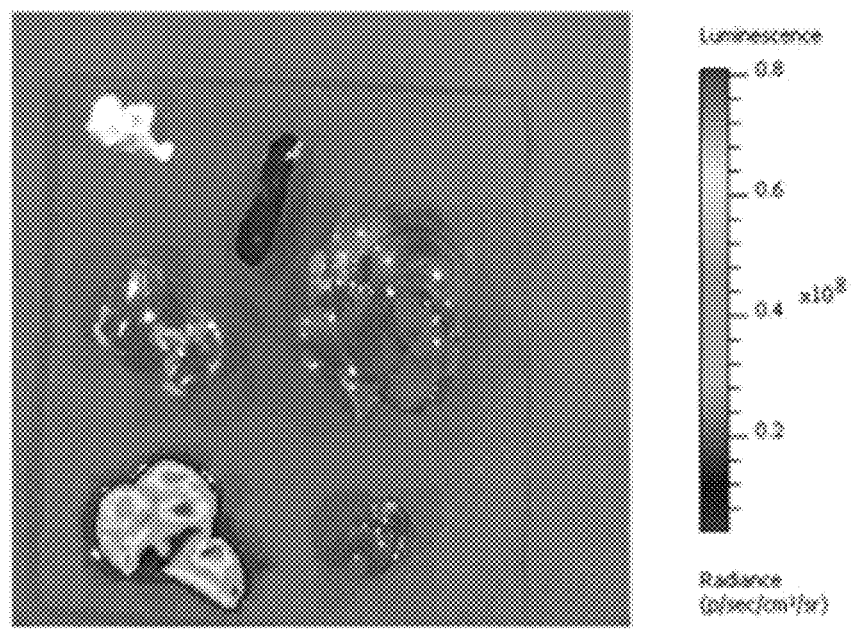
Figure 16C:
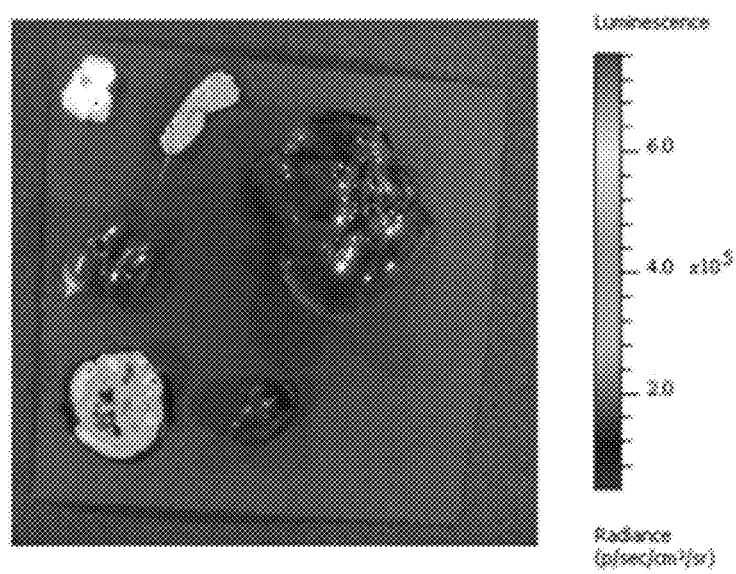

Given that formulation with these moieties in the context of a PBAE terpolymer nanoparticle had not been reported, the potential design space was exceptionally broad. As such, a definitive screen, a special three-level screening design useful in narrowing a design space, was utilized.[33] The parameter ranges chosen can be found in Table 3. Additionally, to ensure proper mixing of all components, these particles were formulated using a microfluidic device that has been shown to consistently synthesize lipid nanoparticles with similar components.[34] As with the in vitro screen, luciferase-coding mRNA was used as a reporter, as it would provide a means of quantifying protein production via image analysis while allowing for the visualization of the biodistribution of mRNA translation. Synthesized particles were injected intravenously in female C57 BL/6 mice (0.5 mg mRNA/kg mouse), and the mouse organs were excised and imaged for luminescence using an IVIS imaging apparatus 24 hours following injection (FIGS. 16A-16C). FIG. 3A shows the results of this screen in the lungs and spleen, the two organs where luminescence was most prominent in the control particle (A1 polymer with 7 mol % C14-PEG2000 PEG-lipid, FIGS. 16A-16C). Only one formulation ($D_2$) was more potent than the original formulation, and only one parameter, DOPE mol %, was statistically significant (FIGS. 7A-7D). However, the goal of the definitive screen was mainly to exclude less important variables.[17]

Figure 3B:
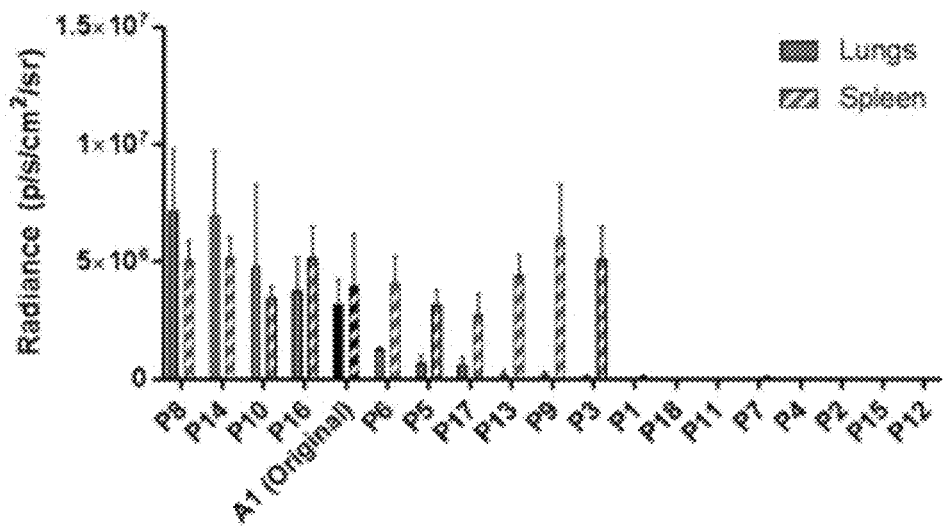

A subsequent partial factorial screen was based off of a combination of the statistical model obtained from the screen as well as the parameter levels used in the D2 formulation (FIG. 3A, Table 3). Specifically, cholesterol and PEG-lipid lipid chain length were eliminated and the remaining parameters were narrowed or altered in range. The parameters for this screen can be seen in Table 5, and a more detailed discussion of how these new parameters were chosen can also be found in the supporting information. FIG. 3B shows that, as one would expect from successive screening, multiple formulations were more potent in the lungs than the original formulation. However, the partial factorial screen revealed several formulations that also transfected the spleen, and the overall lung-specificity of even those particles most effective in the lungs was decreased. To better understand the relationship between formulation and organ-specificity, the effects of PEG-lipid incorporation, which had a significant effect on both lung and spleen efficacy, were investigated (FIGS. 8A-9D). Another dependent variable, particle diameter, was also strongly correlated with PEG-lipid incorporation (FIGS. 10A-10D), so the relationship between particle size and efficacy was also investigated. As can be seen in FIG. S11, there were two distinct diameter regions: very small diameter (<100 nm), which corresponded to low efficacy, and large (>300 nm) diameter, which corresponded with high efficacy in both lung and spleen, with the spleen showing particularly consistent efficacy. Previous studies have reported that larger particles tend to be endocytosed by splenocytes. As for small-diameter particles, the two primary parameters exerting significant negative correlation on particle size were PEG MW and PEG-lipid mol %. This, too, is consistent with the data demonstrating that too much PEG-shielding of PBAE nanoparticles ablates their efficacy.

Figure 3C:
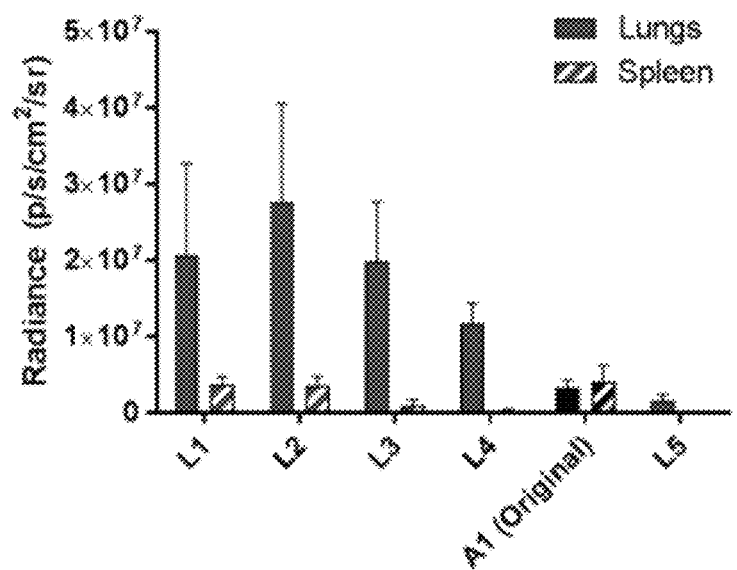
Figure 3D:
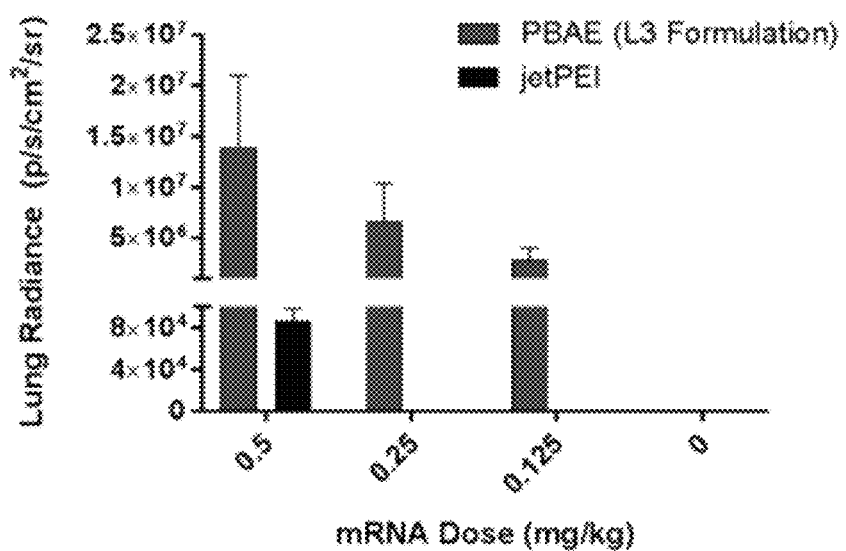
Figure 14:
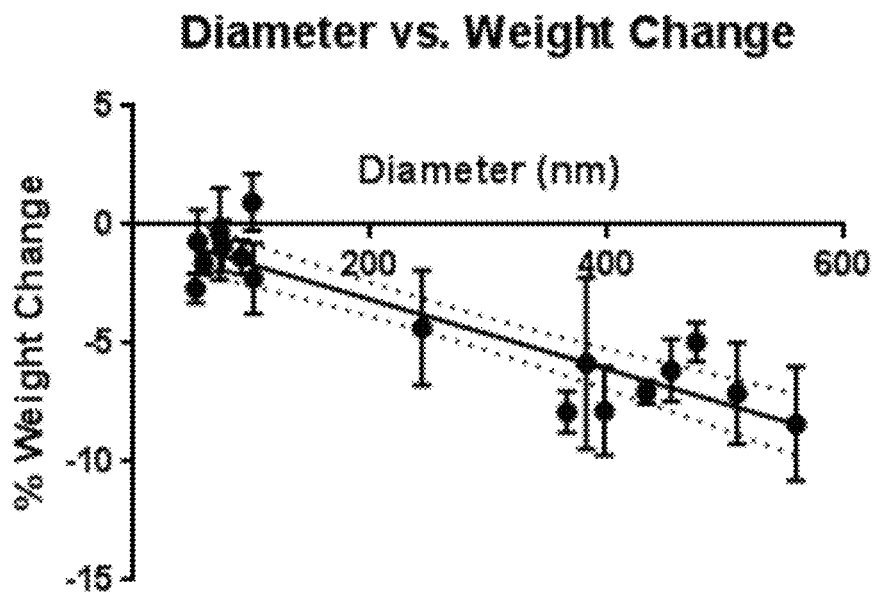
FIG. 14. Correlation between particle diameter and weight loss in mice at 24 hours for the partial factorial formulation screen. Dotted lines indicate 95% confidence interval for a liner regression model (n=3).
Figure 15A:
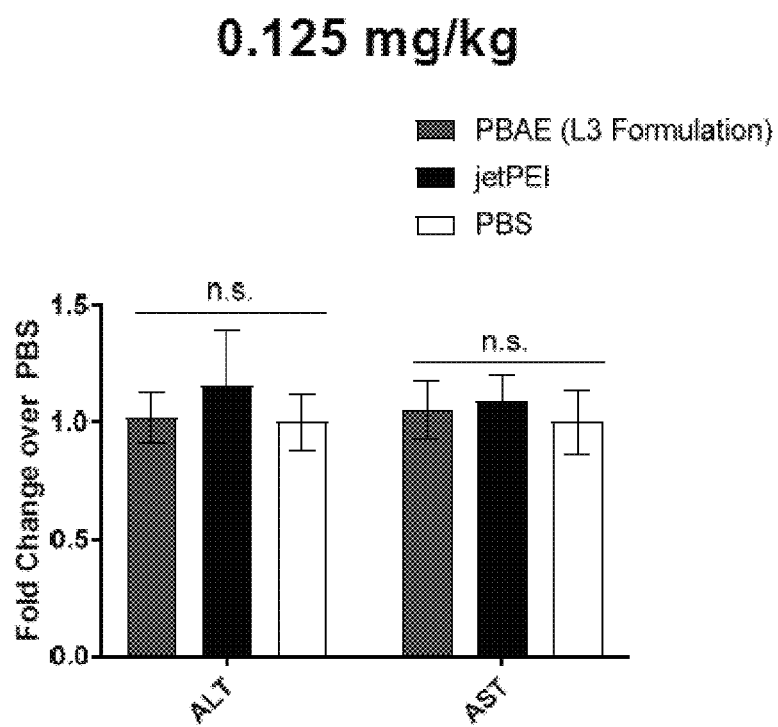
FIGS. 15A-15C. Liver enzyme levels (* indicates p<0.05) following optimized A1-L3 nanoparticle injection of 0.125 mg/kg (FIG. 15A), 0.25 mg/kg (FIG. 15B) and 0.5 mg/kg (FIG. 15C) at 24 hours (n=3).
Figure 15B:
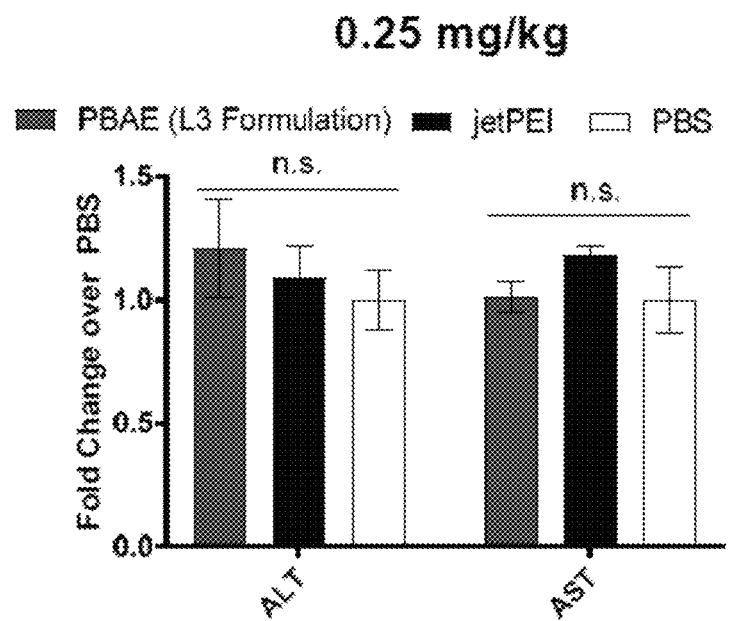
Figure 15C:
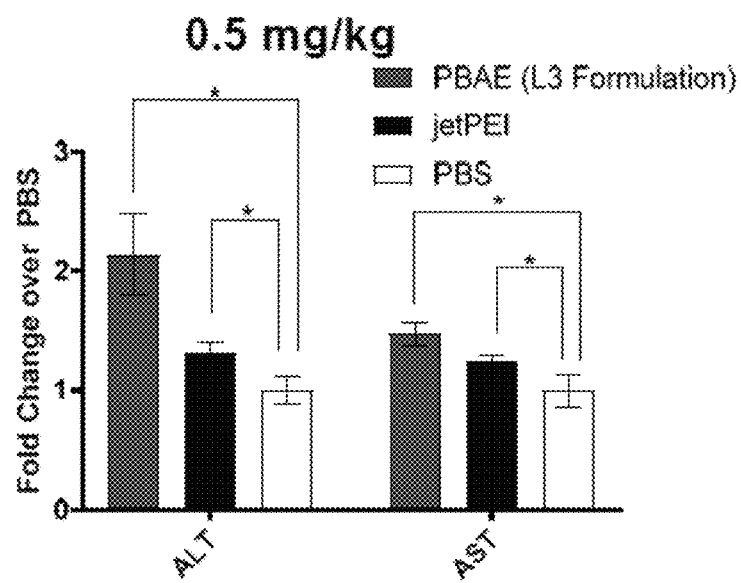
Figure 17:
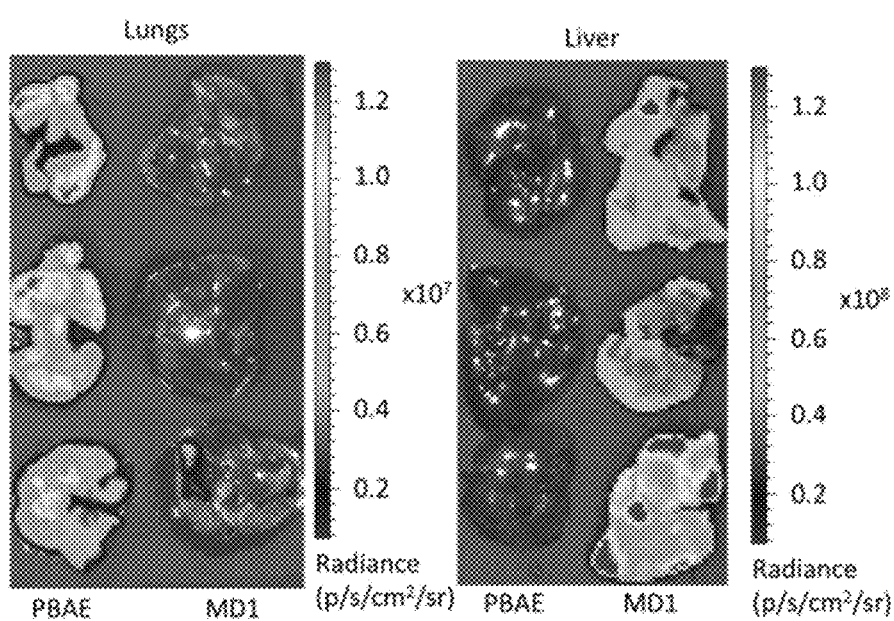
FIG. 17. Comparison of luciferase mRNA delivery efficacy in both lungs and liver at 24 hours using optimized A1-L3 nanoparticles and a leading lipid nanoparticle, cKK-E12 (also known as MD1)[45] (0.5 mg/kg mRNA dose).
Figure 18A:
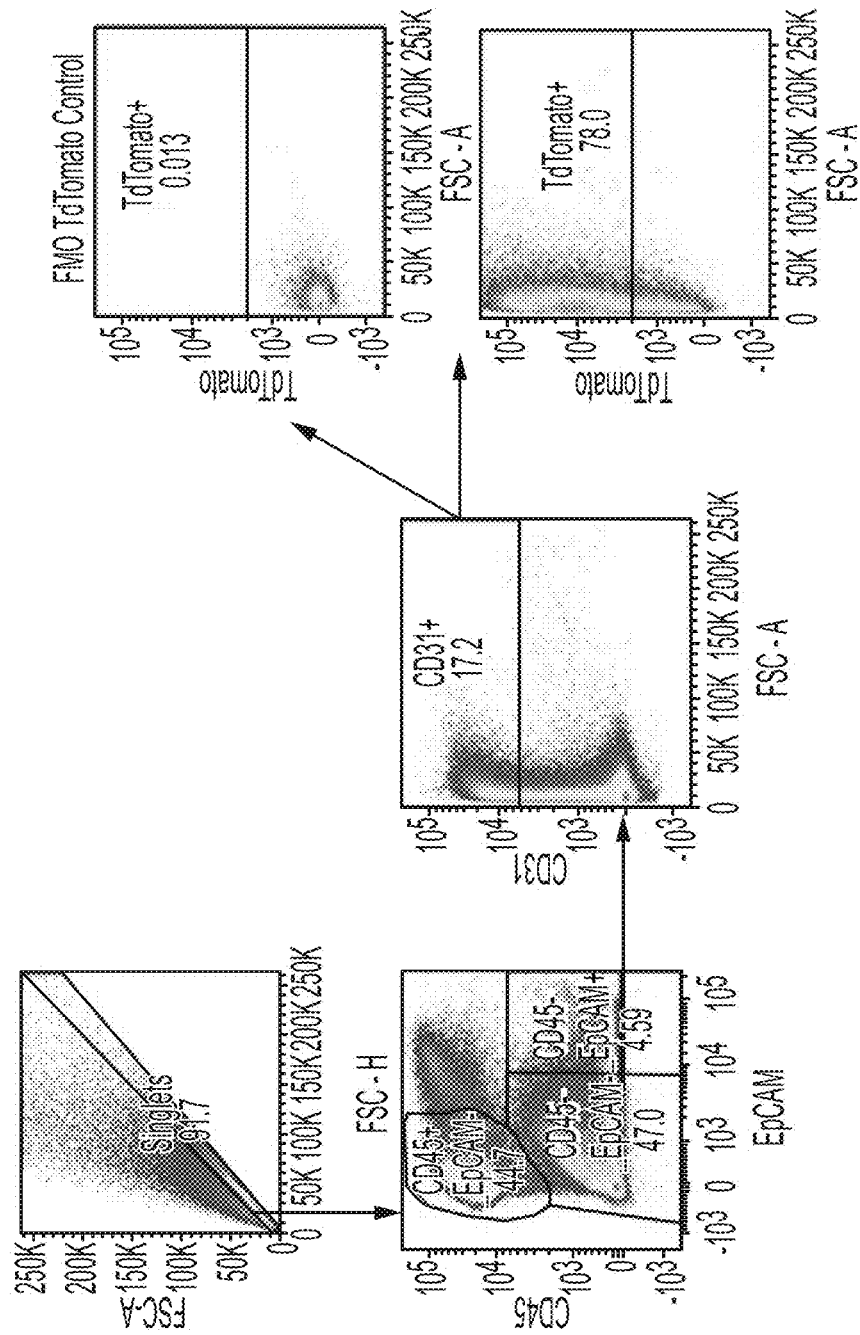
FIGS. 18A-18B. Gating strategy for identifying tdTomato positive endothelial (FIG. 18A) and immune (FIG. 18B) cells.
Figure 18B:
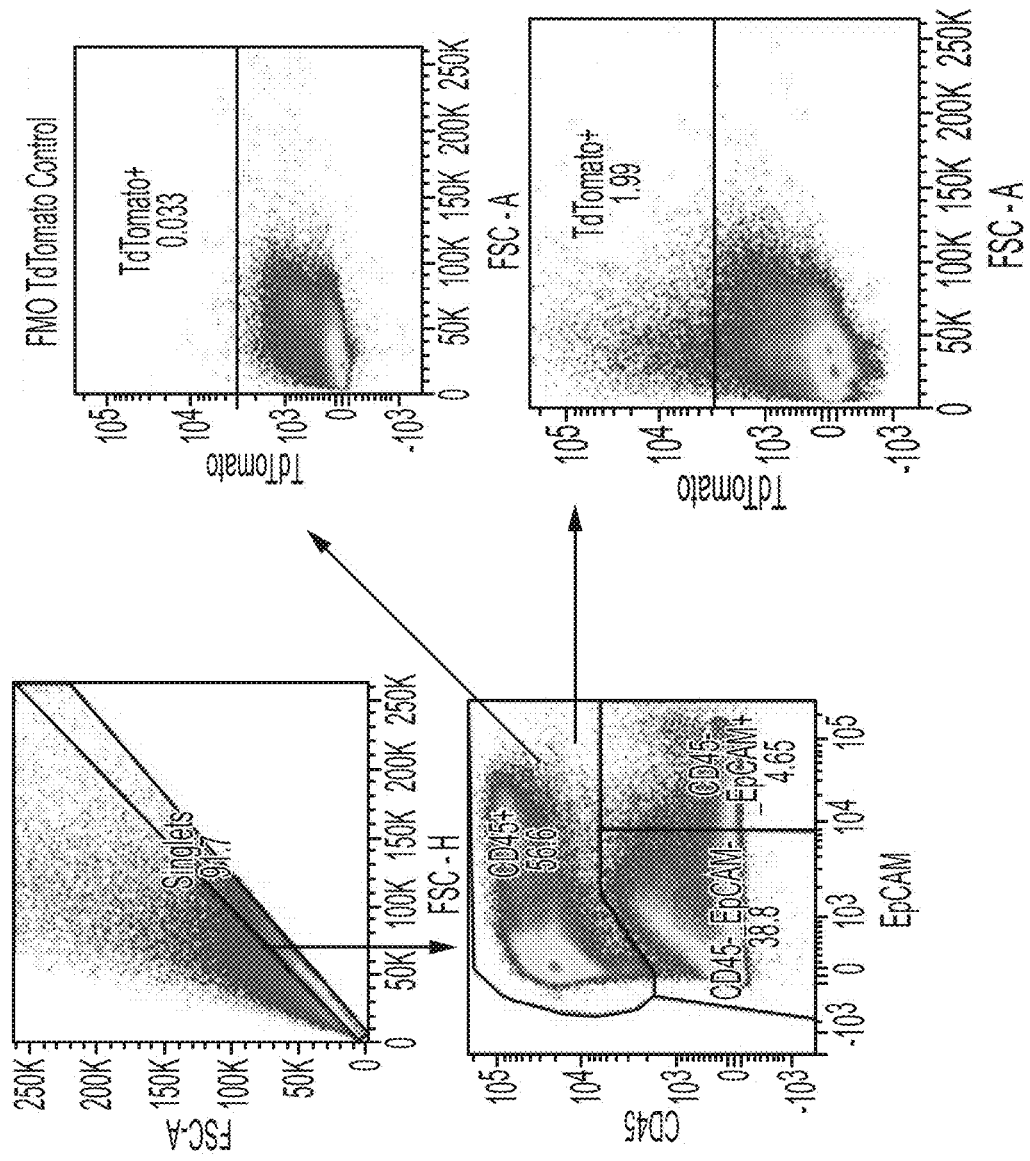
Figure 19:
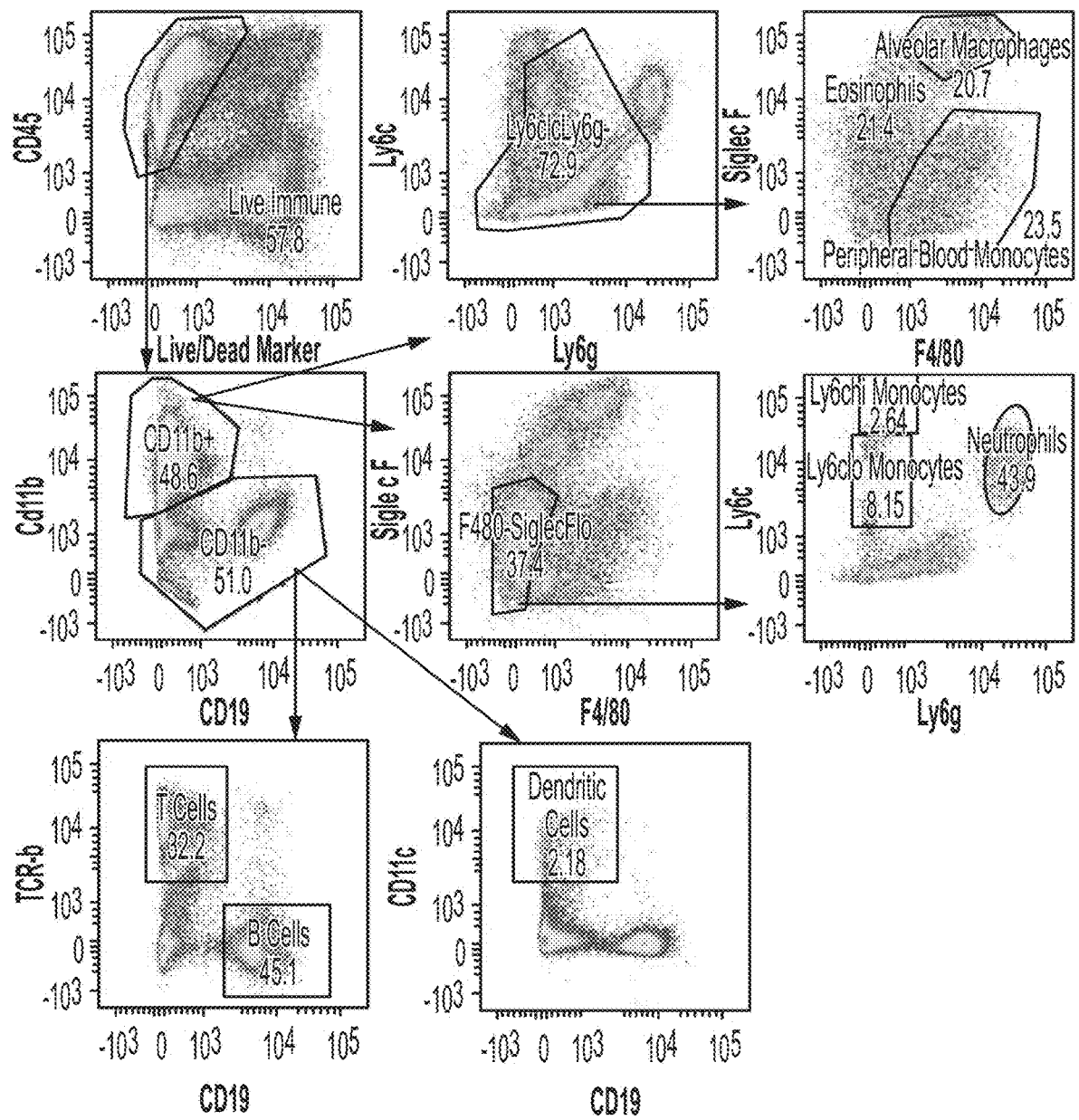
FIG. 19. Gating strategy for identifying lung immune cell populations.

For this final PEG-lipid content-based screen, nanoparticles were synthesized with an N/P of 50, 20 mol % DOPE, and 1-7 mol % C18-PEG2000. All particles synthesized in this range, which yielded particle diameters within the region of interest (FIG. 12), showed improved lung specificity (FIG. 3C). Although formulation L2 (1.5 mol % PEG-lipid) showed the highest efficacy, L3 (5 mol % PEG-lipid) was chosen as the optimized, lung-targeting formulation (Table 1). L3 was not significantly less effective than L2, but it was almost half the size, which the data correlates with generally decreased weight loss following intravenous injection in mice (FIG. 14). Overall, this optimized particle (referred to hereafter as A1-L3) was multiple orders of magnitude more effective than the commercially available in vivo jetPEI reagent across multiple doses (FIG. 3D), and did not significantly alter liver enzyme levels at an intermediate dose (FIGS. 15A-15C). This particle also demonstrated a high degree of lung specificity compared to MD1 (also known as cKK-E12) lipid nanoparticles (FIG. 17).[16,36]

In general, the correlation between nanoparticle size and efficacy is tenuous at best[37], especially when one considers that the particle size measured in solution may not be the same in the context of plasma. Thus, it is not expected that this relationship will be fully translatable to all other mRNA delivery platforms. Nevertheless, for these specific nanoparticles, a correlation between size and lung-specificity was identified (FIGS. 10A-12, FIG. 3C).

Having identified an optimized, lung-targeting particle, it was sought to determine cell populations within the lungs that were being transfected by this formulation. A mouse line expressing a tdTomato fluorophore cassette containing an upstream Lox-P flanked stop codon was utilized. After administering and expressing Cre-recombinase mRNA, this stop codon can be removed from the cassette, causing the cells which successfully translate Cre to constitutively express tdTomato[38]. Using this method, it is possible to identify—with single cell resolution—those cells to which mRNA is delivered.

Figure 4A:
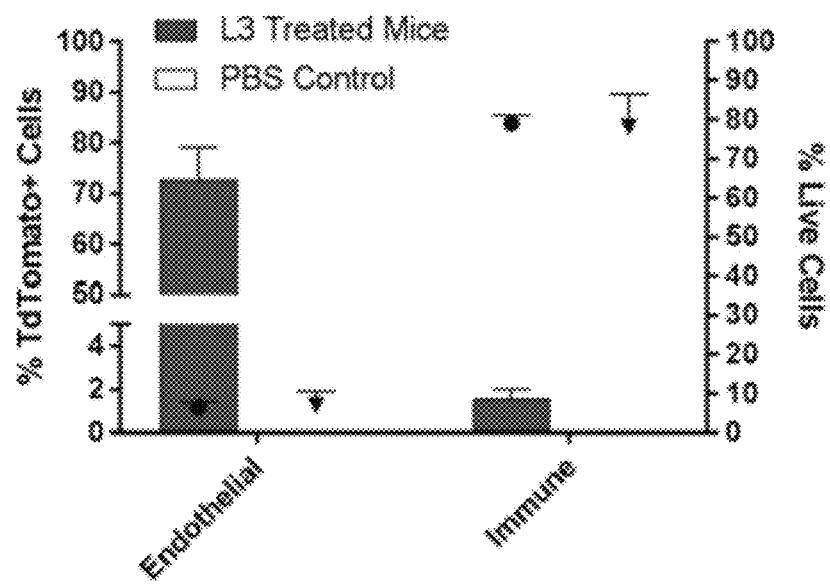
FIGS. 4A-4B. Analysis of lung cell types transfected using Ai14 Cre/lox reporter mice.
Figure 4B:
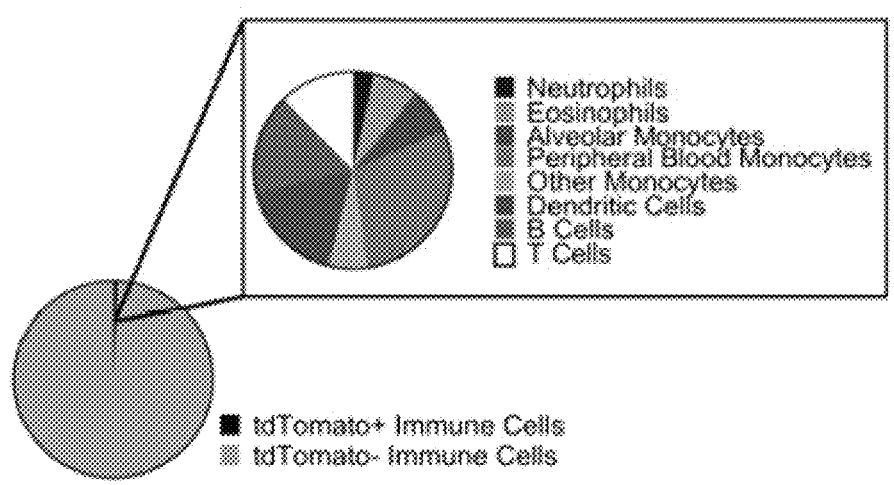
Figure 5A:
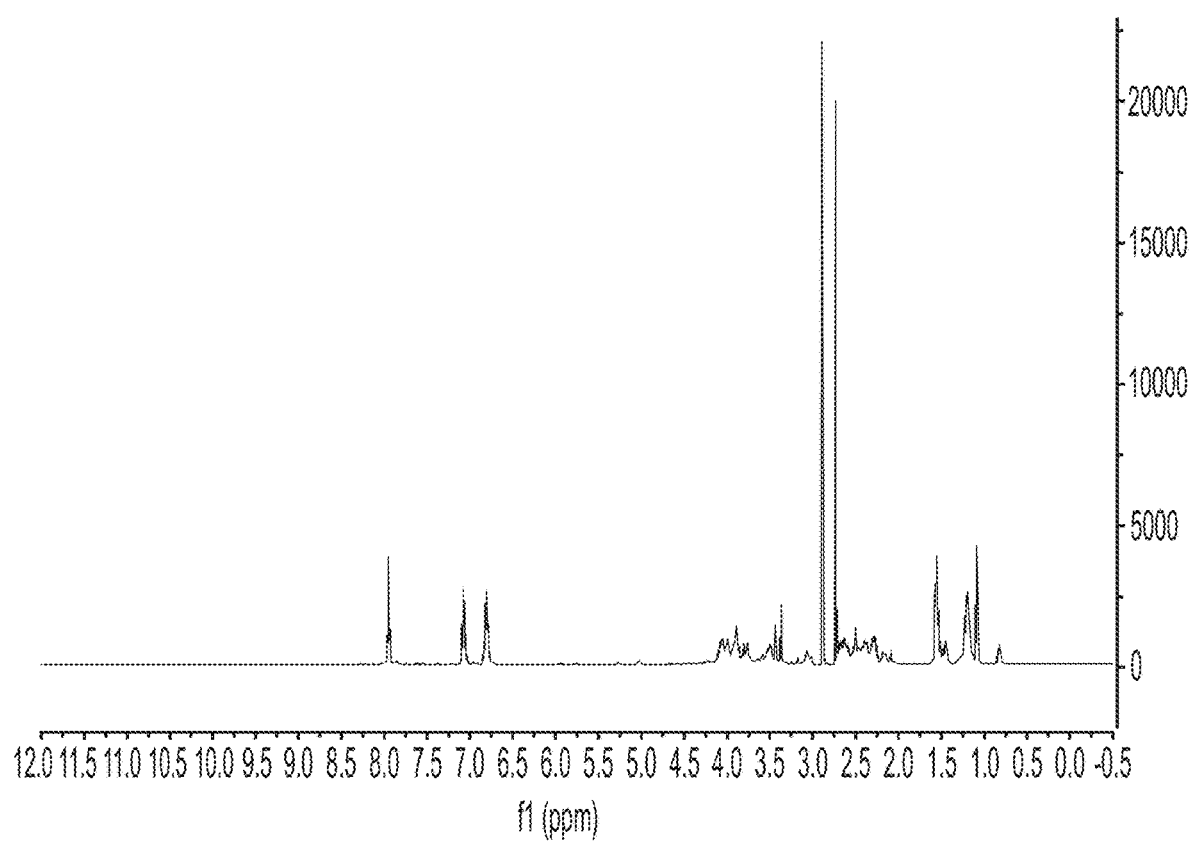
FIGS. 5A-5C. NMR (FIG. 5A), IR (FIG. 5B), and GPC (FIG. 5C) analysis of poly(bisphenol A glycerolate-co-4-(2-amino methyl) morpholine) end capped with 1,3-diamino-propane (A1 polymer).
Figure 5B:
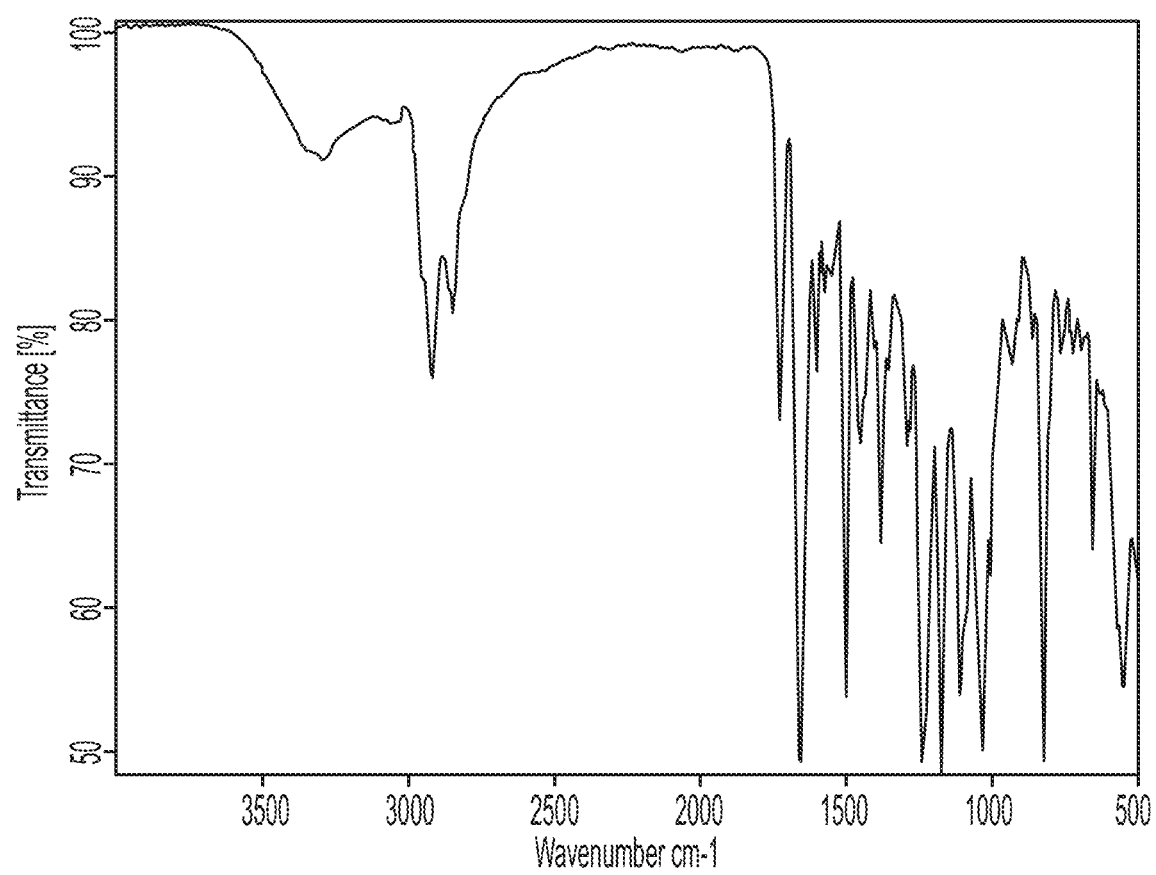
Figure 5C:
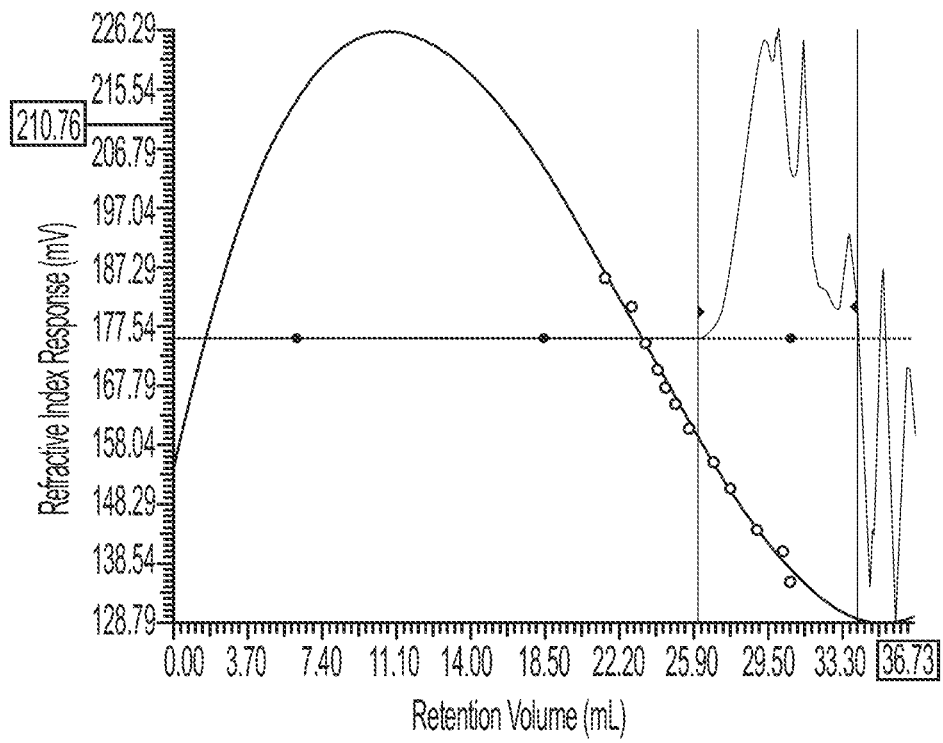
Figure 5C:
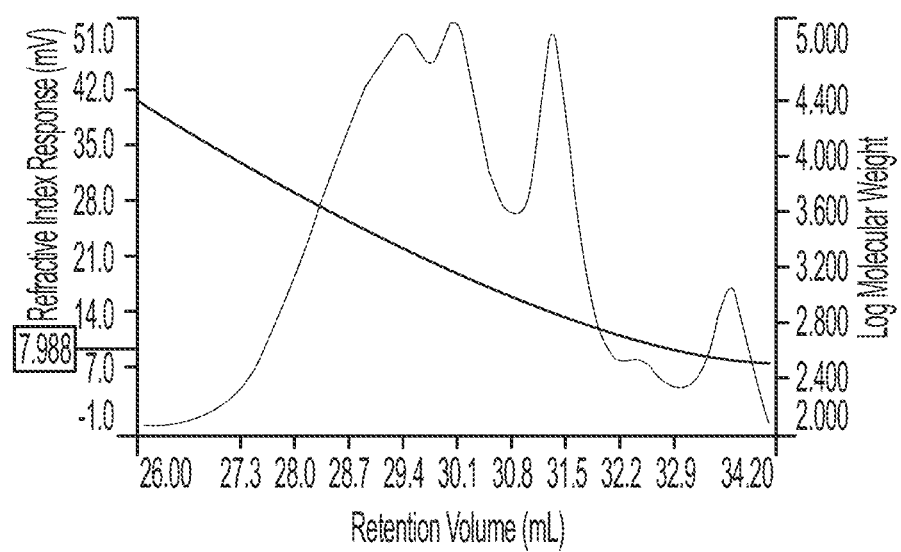
Figure 20:
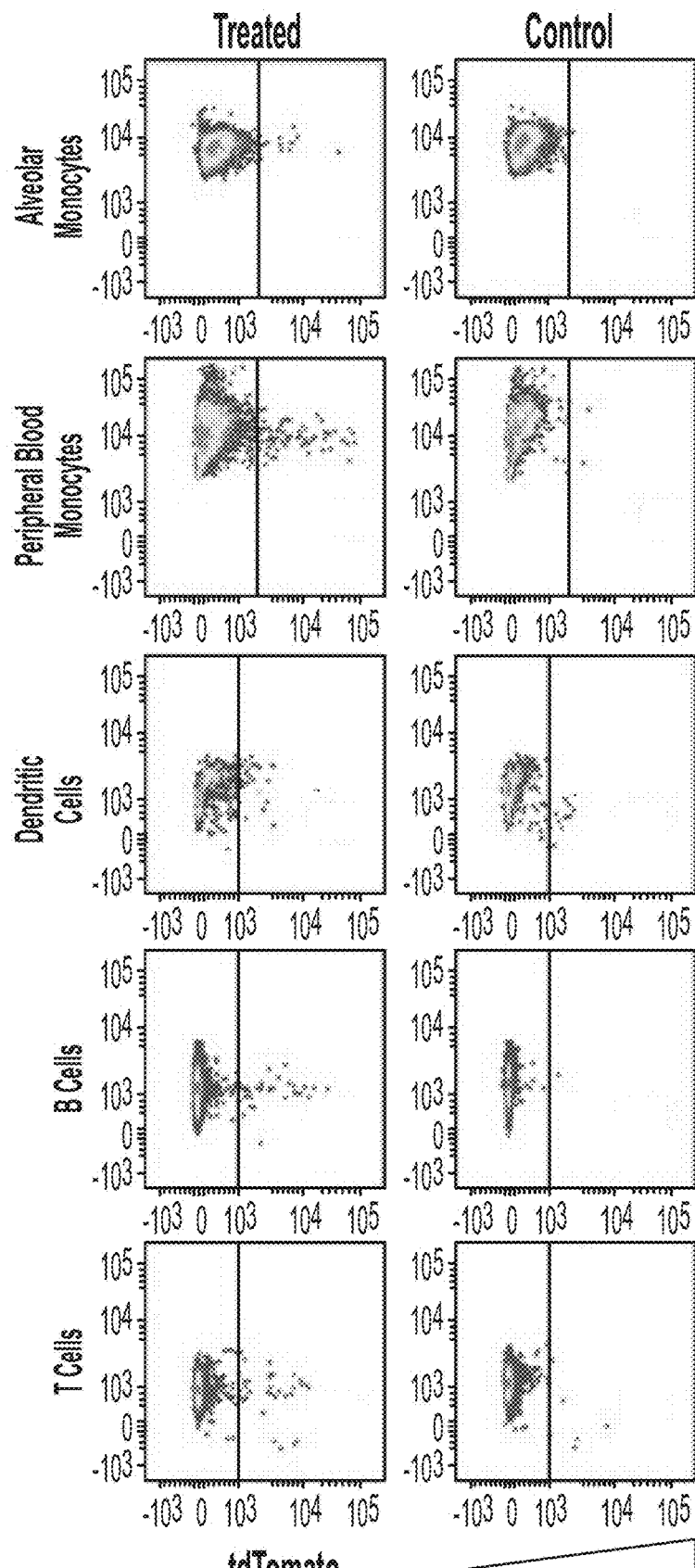
FIG. 20. Gating for tdTomato positive immune cells (x axis).

A1-L3 nanoparticles were formulated with Cre-encoding mRNA, and delivered intravenously. Forty-eight (48) hours later, the mouse lungs were harvested and processed into a single-cell suspension, and analyzed using multi-color flow cytometry (FACS) analysis. This formulation primarily transfected the lung endothelium, with ~75% of endothelial cells expressing tdTomato (FIG. 4A). The number of immune cells transfected (~2%) was low by comparison (FIG. 4A).[39] As shown in FIG. 4B, the majority of immune cells expressing protein are dendritic cells and various monocytes, although a portion T and B cells were also transfected. (FIG. 20).

In conclusion, the design of experiments was utilized to optimize a degradable, polymeric nanoparticle both in terms of polymer synthesis as well as nanoparticle formulation. This methodology allowed for the development of a polymer formulation two orders-of-magnitude more effective than its pre-optimized form in vitro and in vivo (FIG. 2), and the use of successive formulation screens sequentially increased the efficacy of the nanoparticles while additionally allowing for the identification of formulations that maintain lung-specificity (FIG. 3). The utility of these design of experiment methods in the context of a polymeric nanoparticle rather than a lipid nanoparticle further demonstrates its potential for in vivo optimization of RNA delivery vehicles.[17] The use of experimental design in vivo may also be used to optimize nanoparticles for other organs as well. Moreover, the high level of mRNA expression in the lungs, coupled with these particles' ability to transfect pulmonary endothelial and immune cells (FIG. 4) suggests that these particles may be useful in a variety of therapeutic contexts.

Polymers were synthesized by dissolving diacrylate, amine, and alkyl amine monomers (concentration 1M) in anhydrous N,N-dimethylformamide at various molar ratios for 48 hours at 90° C. End-capping monomer was then added at room temperature and reacted for an additional 24 hours, followed by 2-3 washes with diethyl ether. Polymers were stored at −80 to −20° C. and dissolved in DMSO for formulation. Nanoparticles were synthesized by dissolving mRNA in sodium acetate buffer (pH 5.2) and polymer/hydrophobic moieties in ethanol as a separate phase. The two phases were mixed either by hand at a 1:1 v/v ratio or by microfluidic device at a 3:1 aqueous:ethanol v/v ratio. Statistical design and analysis was done using JMP software.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Experimental Section

General Methods and Instruments

Polymers were synthesized by dissolving diacrylate, amine, and alkyl amine monomers (concentration 1M) in anhydrous N, N-dimethylformamide at various molar ratios for 48 hours at 90° C. End-capping monomer was then added at room temperature and reacted for an additional 24 hours, followed by 2-3 washes with diethyl ether. Polymers were stored at −80 to −20° C. and dissolved in DMSO for formulation. Nanoparticles were synthesized by dissolving mRNA in sodium acetate buffer (pH 5.2) and polymer/hydrophobic moieties in ethanol as a separate phase. The two phases were mixed either by hand at a 1:1 v/v ratio or by microfluidic device at a 3:1 aqueous:ethanol v/v ratio. Statistical design and analysis was done using JMP software.

All animal experiments were approved by the MIT Institutional Animal Care and Use Committee and were consistent with local, state, and federal regulations as applicable.

Additional experimental details can be found in the examples.

Example 1: Chemical Synthesis and Characterization

Representative Synthesis of A1 Polymer

All monomers were pre-dissolved in N,N-dimethylformamide at a concentration of 1 M. To a 5 mL glass scintillation vial were added the bisphenol A glycerolate diacrylate (200 mg, 0.41 mmol, 1.2 equiv), 4-(2-amino methyl) morpholine (22 mg, 0.17 mmol, 0.5 equiv), and dodecyl amine (32 mg, 0.17 mmol, 0.5 equiv). The vial was then sealed, covered in aluminum foil, and heated to 90° C. After 48 hours, the reaction was cooled to room temperature. The vial was opened to the air and end-capping amine 1,3-diaminopropane was added in excess (38 mg, 0.51 mmol) and mixed until completely dissolved. The end-capping reaction was allowed to proceed at room temperature for 24 hours, after which the reaction was diluted in diethyl ether at a ratio of 4:1 ether:crude product v/v and vigorously vortexed. The heterogeneous mixture was then centrifuged for 2 minutes at 1250×g. The liquid was then decanted, leaving behind the polymeric solid. The ether wash/centrifugation/decanting process was repeated an additional time, and then the solid was dried under reduced pressure. The resulting polymer was characterized by gel permeation chromatography (GPC), infrared spectroscopy (IR), and 1H nuclear magnetic resonance (NMR). The polymer was stored neat at −20 to −80° C., with samples taken and dissolved in DMSO at 100 mg/mL as needed.

Other polymer variants were synthesized as above, with molar ratios, end-capping monomer, and alkylamine monomer adjusted as necessary. For library synthesis, diacrylate scale was kept at 200 mg for all reactions, and end-capping monomer was added at a ratio of 1 mmol per 500 mg of diacrylate plus amines.

Instrumentation and Methods

Proton nuclear magnetic resonance (1H and 13C NMR) spectra were recorded with a Varian inverse probe INOVA-500 spectrometer (with a Magnex Scientific superconducting actively-shielded magnet), are reported in parts per million on the δ scale, and are referenced from the residual protium in the NMR solvent (DMSO-d6: δ2.50)[40] displaying a window range of 9 to −0.5 ppm.

Infrared data (IR) were obtained with a Bruker Alpha FTIR spectrometer. Samples were collected neat on a ZnSe ATR crystal, and spectra are reported as percent absorbance as a function of frequency of absorption (cm−1). Gel Permeation Chromatography (GPC) was carried out in tetrahydrofuran (THF) on Styragel columns utilizing a Malvern Viscotek™ TDA 305 triple detection system. Samples were filtered over 0.2 μm PTFE filters before injection using a 1.0 mL/minute flow rate. Molecular weights and polydispersities were determined by comparing to a linear polystyrene standard.

Example 2: Extended Experimental Methods

Materials

Bisphenol A glycerolate, 4-(2-amino methyl) morpholine, octyl amine (alkylamine C8), dodecyl amine (alkylamine C12), octadecyl amine (alkylamine C18), 1,3-diaminopropane (end cap 1), 1,3-diaminopentane (end cap 3), 2-methyl-1,5-diaminopentane (end cap 4), and cholesterol were purchased from Aldrich (St. Louis, Mo.). 2,2-dimethyl-1,3-diaminopropane (end cap 2) was purchased from TCI America (Mountain View, Calif.). (Poly-ethylene oxide)4-bis-amine (end cap 5) was purchased from Molecular Biosciences (Boulder, Colo.). Heparin sodium salt from porcine intestinal mucosa was obtained from Alfa Aesar (Haverhill, Mass.). 14:0 PEG1000 PE (C14-PEG1000), 14:0 PEG2000 PE (C14-PEG2000), 14:0 PEG3000 PE (C14-PEG3000), 14:0 PEG5000 PE (C14-PEG5000), 16:0 PEG1000 PE (C16-PEG1000), 16:0 PEG2000 PE (C16-PEG2000), 16:0 PEG3000 PE (C16-PEG3000), 16:0 PEG5000 PE (C16-PEG5000), 18:0 PEG1000 PE (C18-PEG1000), 18:0 PEG2000 PE (C18-PEG2000), 18:0 PEG3000 PE (C18-PEG3000), and 18:0 PEG5000 PE (C18-PEG5000), and 1,2-dioleoyl-sn-glycero-3-phosphoethanolamine (DOPE) were purchased from Avanti Polar Lipids (Alabaster, Ala.). jetPEI and in vivo jetPEI were obtained from VWR (Radnor, Pa.). Firefly luciferase-encoding mRNA was generously provided by Shire Pharmaceuticals (Lexington, Mass.). All chemical reagents were used as received with no further purification. NLS-Cre mRNA 100% modified with pseudouridine and 5-methylcytidine, capped with Cap 0, and polyadenylated was purchased from Tri-Link Biotechnologies (San Diego, Calif.).

mRNA Synthesis

Luciferase-encoding mRNA was a generous gift from Translate Bio, and was synthesized by an in vitro transcription from a plasmid DNA template encoding for the firefly luciferase gene. The in vitro transcription was followed by the addition of a 5' cap structure (Cap 1) using a vaccinia virus-based guanylyl transferase system. FLuc mRNA contained a 5' UTR consisting of a partial sequence of the cytomegalovirus (CMV) immediate early 1 (IE1) gene, a coding region as described below, a 3' UTR consisting of a partial sequence of the human growth hormone (hGH) gene, and a 3' polyA tail (~300 nt).

(SEQ ID NO: 1)
AUGGAAGAUGCCAAAAACAUUAAGAAGGGCCCAGCGCCAUUCUACCCACU

CGAAGACGGGACCGCCGGCGAGCAGCUGCACAAAGCCAUGAAGCGCUACG

CCCUGGUGCCCGGCACCAUCGCCUUUACCGACGCACAUAUCGAGGUGGAC

AUUACCUACGCCGAGUACUUCGAGAUGAGCGUUCGGCUGGCAGAAGCUAU

GAAGCGCUAUGGGCUGAAUACAAACCAUCGGAUCGUGGUGUGCAGCGAGA

AUAGCUUGCAGUUCUUCAUGCCCGUGUUGGGUGCCCUGUUCAUCGGUGUG

GCUGUGGCCCCAGCUAACGACAUCUACAACGAGCGCGAGCUGCUGAACAG

CAUGGGCAUCAGCCAGCCCACCGUCGUAUUCGUGAGCAAGAAAGGGCUGC

AAAAGAUCCUCAACGUGCAAAAGAAGCUACCGAUCAUACAAAAGAUCAUC

AUCAUGGAUAGCAAGACCGACUACCAGGGCUUCCAAAGCAUGUACACCUU

CGUGACUUCCCAUUUGCCACCCGGCUUCAACGAGUACGACUUCGUGCCCG

AGAGCUUCGACCGGGACAAAACCAUCGCCCUGAUCAUGAACAGUAGUGGC

-continued
AGUACCGGAUUGCCCAAGGGCGUAGCCCUACCGCACCGCACCGCUUGUGU

CCGAUUCAGUCAUGCCCGCGACCCCAUCUUCGGCAACCAGAUCAUCCCCG

ACACCGCUAUCCUCAGCGUGGUGCCAUUUCACCACGGCUUCGGCAUGUUC

ACCACGCUGGGCUACUUGAUCUGCGGCUUUCGGGUCGUGCUCAUGUACCG

CUUCGAGGAGGAGCUAUUCUUGCGCAGCUUGCAAGACUAUAAGAUUCAAU

CUGCCCUGCUGGUGCCCACACUAUUUAGCUUCUUCGCUAAGAGCACUCUC

AUCGACAAGUACGACCUAAGCAACUUGCACGAGAUCGCCAGCGGCGGGGC

GCCGCUCAGCAAGGAGGUAGGUGAGGCCGUGGCCAAACGCUUCCACCUAC

CAGGCAUCCGCCAGGGCUACGGCCUGACAGAAACAACCAGCGCCAUUCUG

AUCACCCCCGAAGGGGACGACAAGCCUGGCGCAGUAGGCAAGGUGGUGCC

CUUCUUCGAGGCUAAGGUGGUGGACUUGGACACCGGUAAGACACUGGGUG

UGAACCAGCGCGGCGAGCUGUGCGUCCGUGGCCCCAUGAUCAUGAGCGGC

UACGUUAACAACCCCGAGGCUACAAACGCUCUCAUCGACAAGGACGGCUG

GCUGCACAGCGGCGACAUCGCCUACUGGGACGAGGACGAGCACUUCUUCA

UCGUGGACCGGCUGAAGAGCCUGAUCAAAUACAAGGGCUACCAGGUAGCC

CCAGCCGAACUGGAGAGCAUCCUGCUGCAACACCCCAACAUCUUCGACGC

CGGGGUCGCCGGCCUGCCCGACGACGAUGCCGGCGAGCUGCCCGCCGCAG

UCGUCGUGCUGGAACACGGUAAAACCAUGACCGAGAAGGAGAUCGUGGAC

UAUGUGGCCAGCCAGGUUACAACCGCCAAGAAGCUGCGCGGUGGUGUUGU

GUUCGUGGACGAGGUGCCUAAAGGACUGACCGGCAAGUUGGACGCCCGCA

AGAUCCGCGAGAUUCUCAUUAAGGCCAAGAAGGGCGGCAAGAUCGCCGUG

UAA

Scrambled-sequence mRNA was transcribed from a DNA plasmid containing a T7 promoter upstream of the coding region. The plasmid was linearized using restriction enzyme Xbal (New England Biolabs, Ipswich, Mass.) and transcribed using the HiScribe T7 RNA Synthesis Kit (New England Biolabs). mRNA was capped with the Vaccinia Capping System (New England Biolabs), and the cap was modified to Cap1 using mRNA cap 2'-O-Methyltransferase (New England Biolabs). A polyA (estimated to be approximately 100 nucleotides long) tail was added to the RNA using a Poly(A) Polymerase Kit (New England Biolabs). mRNA was purified after the transcription and tailing steps using MEGAClear RNA purification columns (Life Technologies, Beverly, Mass.). RNA concentration was determined using a NanoDrop 1000 (Thermo Scientific, Cambridge, Mass.). The mRNA sequence used is given below:

(SEQ ID NO. 2)
AUGGUUCGAGGGUGAACGAAGCGACUGUCUCGGCGGUUCCCCUAGCCAC

GGGUGAGAGAGUUGACGCCGCGAGUCGCGAGUGGACAGUGCGGCUGCGGC

UCGGACGUUGACCGACAGUGAGAGGACCGGCACACAGAGCCCACACCUCC

CGUCAGCCAUUCGCUACCUUGUGAGGCGUUGGGACUCUUUUCCGGUGGGG

AUCCGCCGAUCACGACGCCUUGCUAGACCGGGGGCUGUGAAUCCACCCAA

GAUCUUUAUCUGGCUGGGUGGCGACUGCGCGCUUGACGCGCGACCGACCC

CGAGCAAAGUCAUAACAUAGUGGAGCCUGGUUGUGUGGCUGUCGAAUACC

-continued
CCUUUGGCGUGUUCAGGACGAAGGGGCGUCAUUUGUCACCGGUGAUCACC

AUCGUGCCAGACCGAGCGCACACUACACGAGCUGCUUAGACCGCAUAUCA

UACGGAAGGGUCUCCCUACUUCCCACGACUCCUUUUGACAGUUCUCACAU

CCUCGUGAGUCAGCGCCCGCGAGCCUAUUUUACGUGGCACUAGGCCUCCG

ACCCAGUCGCCUCACCACACGAAACCCUGUA

Figure 13:
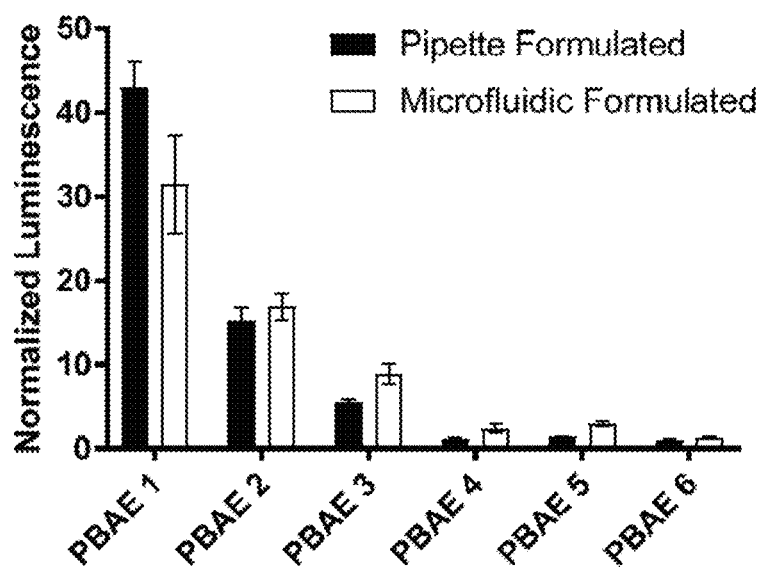
FIG. 13. Pilot study with various PBAEs (used in previous studies[44]) delivering luciferase-coding mRNA in HeLa cells demonstrating little difference between microfluidic formulated and pipette formulated particles when PEG-lipid (7 mol %) is the only additional excipient added (n=4).

Nanoparticle Synthesis mRNA was diluted in 25 mM sodium acetate (NaOAc) buffer while the appropriate amounts of polymer and PEG-lipid were co-dissolved in 200 proof ethanol. For particles synthesized by hand mixing, the aqueous:ethanol phase ratio was 1:1 v/v, and particle formation was performed by adding the ethanol phase to the aqueous phase and mixing vigorously. Nanoparticles formulated via microfluidic device[41] were synthesized at a 3:1 v/v ratio of mRNA phase to the polymer phase. For particles formulated with only PEG-lipid, little difference in efficacy was apparent between the pipette-mixing and microfluidic-mixing strategies (FIG. 13). Nanoparticles were then dialyzed against PBS in a 20000 MWCO cassette at 4° C. for 2-3 hours. jetPEI nanoparticles were made according to supplier protocol. Briefly, jetPEI and RNA were diluted in equal volumes of the provided buffer in order to yield the desired N/P. The jetPEI phase was added to the RNA phase and was mixed by vortexing, and the resulting nanoparticles were incubated at room temperature for 15 minutes prior to use. All particles were used no earlier than 15 minutes and no later than 4 hours following synthesis.

Nanoparticle Characterization

The mRNA concentration in dialyzed particles was determined via a modified Quant-iT RiboGreen RNA assay (Thermo Fisher). A nanoparticle dilution of ~1 ng μL-1 mRNA was made in TE buffer (pH 8.5) and mRNA standards were made ranging from 2 ng μL-1 to 0.125 ng μL-1. 50 μL of each solution was added to separate wells in a 96-well black polystyrene plate. To each well was added either 50 μL of 10 mg/mL heparin in TE buffer, which disrupted the electrostatic forces binding the polymer and mRNA to allow for accurate quantification of nanoparticle mRNA content, or 50 μL of un-supplemented TE buffer. The plate was incubated at 37° C. for 15 minutes with shaking at 350 rpm. Following the incubation, the diluted RiboGreen reagent was added (100 μL per well), and the plate was incubated as before for 3 minutes. RiboGreen fluorescence was measured according to the supplied protocol using a Tecan plate reader, and the mRNA standard was used to determine nanoparticle mRNA concentration. It should be noted that two separate standards were made: one with and one without 10 mg/mL heparin. The particles in heparin were used to determine mRNA concentration, and encapsulation efficiency was determined via the following equation:

$$EE = \left(1 - \frac{Conc_{TE}}{Conc_{Hep}}\right)$$

where $Conc_{TE}$ and $Conc_{Hep}$ are the concentration readings for particles without and with heparin, respectively. Nanoparticle size was measured via dynamic light scattering via a standard (ZetaPALS, Brookhaven Instruments) or high-throughput (Dyna Pro Plate Reader, Wyatt) system. For size measurement, particles were diluted in PBS at a 1:16 v/v ratio and an intensity average measurement was reported for particle size.

In Vitro Transfections

HeLa cells (ATCC) were cultured in Dulbecco's Modified Eagle Medium (Invitrogen) supplemented with 10% v/v heat inactivated fetal bovine serum (Invitrogen) and 1% v/v Penicillin Streptomycin (Invitrogen). 24 hours before transfection, cells were seeded onto a 96-well polystyrene tissue culture plate (20,000 cells per well, 100 µL media containing serum and antibiotic per well). In a typical example, mRNA-loaded nanoparticles were diluted to 5 ng µL-1 in buffer and mixed with media such that the volume ratio of nanoparticle solution to media was 1:9. The media in the plate was aspirated, and the nanoparticle-containing media was added to the wells, in this case at a final concentration of 50 ng mRNA per well. 24 hours following transfection, cell viability was assayed using a MultiTox-Fluor Multiplex Cytotoxicity Assay (Promega) and cellular luminescence was quantified using Bright-Glo Assay kits (Promega), both of which were measured using a Tecan plate reader. Cellular luminescence was normalized to live cell fluorescent signal. No wash step was used following particle transfection.

Animal Studies

All animal experiments were approved by the M.I.T. Institutional Animal Care and Use Committee and were consistent with local, state, and federal regulations as applicable. Female C57BL/6 mice (Charles River Laboratories, 18-22 g) were intravenously injected with nanoparticles via the tail vein. For luciferase imaging experiments, mice were injected intraperitoneally with 130 µL of 30 mg mL-1 D-luciferin (PerkinElmer) in PBS 24 hours after injection. 10 minutes following luciferin injection, mice were sacrificed via CO2 asphyxiation. Six organs were collected (pancreas, spleen, kidneys, liver, lungs, and heart) and imaged for luminescence using an IVIS imaging apparatus (PerkinElmer) with the luminescence being quantified using Living Image Software (PerkinElmer). For Cre mRNA experiments, female B6.Cg-Gt(ROSA)26Sortm14(CAG-td-Tomato)Hze/J (Ai14) mice (Jackson Laboratories, 18-22 g) were intravenously injected with nanoparticles via the tail vein. 48 hours post-injection, mice were sacrificed via CO2 asphyxiation and their lungs were harvested for single cell processing. Saline-treated wild type C57BL/6 mice were used as controls for experiments probing gross immune and endothelial expression. To account for differences in immune cell populations following nanoparticle treatment, Ai14 mice treated with A1-L3 PBAEs carrying a scramble mRNA sequence were used as controls for experiments identifying transfected immune cell subpopulations.

Liver Enzyme Level Testing

Alanine transaminase (ALT) and aspartate transaminase (AST) activity kits were purchased from Sigma Aldrich (St. Louis, Mo.). Whole blood was obtained from mice via tail vein bleed 24 hours following nanoparticle dosing in serum collection tubes (Sarstedt). The tubes were then centrifuged according to manufacturer instruction to enable plasma collection. Plasma was then diluted in sample buffer from activity kits, and the colorimetric assay was run per manufacturer instruction. ALT and AST levels were normalized to PBS-treated mice.

Flow Cytometry

Lungs were digested in a mixture of collagenase I (450 U), collagenase XI (125 U), and DNase I (2 U) in 1 mL PBS at 37° C. with constant agitation for 1 hour. The digest was passed through a 70 µm filter, followed by centrifugation. The supernatant was then removed, and cells were treated with red blood cell lysis buffer for 5 minutes at 4° C. The lysis buffer was then quenched with PBS, and the cells were then centrifuged again with the supernatant removed afterwards. The cells were then suspended in flow buffer (PBS containing 0.5% BSA and 2 mM EDTA) and passed through a 40 µm filter. Cells were incubated with viability dye (eBioscience Fixable Viability Dye eFluor 780, Invitrogen) at a 1:1000 dilution at 4° C. for 30 minutes, followed by a wash with flow buffer. Surface staining of cells with fluorescent antibodies was then performed using the antibodies and dilutions listed in Table 7 at 4° C. in flow buffer for 30-60 minutes. Following surface staining, cells were washed twice with and then re-suspended in flow buffer for analysis.

Gating strategies for cell population identification can be found in FIGS. 18A-20, and antibodies and dilutions can be found in Table 7. Data was collected using a BD LSR II or Fortessa cytometer (BD Biosciences) and analyzed with FlowJo software (Ashland, Oreg.).

Statistics

Data were expressed as mean±SD for groups of at least three replicates, or as individual values with the mean indicated. All statistical analyses for design of experiments modeling were performed using JMP Pro 12 software. Other statistical analysis (e.g. of graphical data) were performed using an unpaired, two-tailed student's t test in Graphpad Prism 7.

Example 3: Experimental Design Methodology

In general, experimental design applies statistical methodologies in order to reduce a design space while maintaining enough information to determine variables (or combinations of variables) which have a significant effect on an outcome. In other words, experimental design strategically "picks" a limited number of test conditions from a full factorial set that will maximize (based on the desired resolution) the conclusions that can be drawn about independent variable effects on dependent variables. There are many algorithms that can be used determine which conditions will be chosen from the set[42], which leads to a variety of ways in which experimental design can be executed and a variety of interaction levels between dependent variables that can be accurately assessed. The majority of this section will be focused on the specifics of design choices made for this particular study. For a more general explanation of applying experimental design to nanoparticle formulation, the reader is directed to the supplementary information of the following paper.[43]

Synthesis Screen

All experimental design was done using JMP Pro 12 software. The variables and their levels for the synthesis screen are shown in Table 1. For the synthesis screen, the main concern was with first order effects, and as such the default JMP algorithm was applied to determine conditions for a fractional factorial screen for main effects. All continuous variables were to be tested at three levels (in order to observe any nonlinear effects) along with 5 levels of the categorical end-capping variable (corresponding to 5 different end caps tested), and 30 conditions were chosen to be tested (Table 2). In all cases, due to the range of values obtained, the log 10 of luciferase expression was used to build the statistical model in order to keep samples with very high (or very low) efficacy from skewing the results.

TABLE 1

Parameter range for synthesis screen.

| Parameter | Range | "A1" PBAE |
|---|---|---|
| Diacrylate:Total Amine Ratio | 1:1-1.2:1 | 1.2:1 |
| Alkylamine:Amine Ratio | 1:9-1:1 | 1:1 |
| Hydrophobic Amine Length | 8-18 | 12 |
| End Cap | 5 monomers | 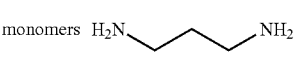 |

TABLE 2

Conditions for synthesis screen.

| Polymer ID | Diacrylate:Amine Ratio | Alkylamine mol % | Alkylamine Length | End Cap ID |
|---|---|---|---|---|
| A1 | 1.2 | 50 | 12 | 1 |
| A2 | 1.1 | 50 | 8 | 3 |
| A3 | 1 | 50 | 18 | 2 |
| A4 | 1.1 | 10 | 12 | 5 |
| A5 | 1.1 | 50 | 8 | 1 |
| A6 | 1 | 50 | 12 | 3 |
| A7 | 1.1 | 50 | 18 | 5 |
| A8 | 1 | 10 | 12 | 1 |
| A9 | 1.1 | 30 | 18 | 4 |
| A10 | 1.2 | 30 | 18 | 1 |
| A11 | 1.1 | 10 | 18 | 1 |
| A12 | 1.2 | 30 | 8 | 2 |
| A13 | 1 | 50 | 12 | 2 |
| A14 | 1.1 | 30 | 12 | 4 |
| A15 | 1 | 50 | 12 | 4 |
| A16 | 1.1 | 30 | 12 | 3 |
| A17 | 1 | 10 | 8 | 4 |
| A18 | 1.2 | 10 | 12 | 5 |
| A19 | 1.2 | 10 | 8 | 4 |
| A20 | 1.2 | 50 | 18 | 4 |
| A21 | 1.2 | 50 | 8 | 5 |
| A22 | 1.2 | 10 | 8 | 3 |
| A23 | 1 | 30 | 8 | 1 |
| A24 | 1 | 10 | 18 | 3 |
| A25 | 1.1 | 10 | 18 | 2 |
| A26 | 1.1 | 10 | 8 | 2 |
| A27 | 1 | 30 | 18 | 5 |
| A28 | 1 | 30 | 8 | 5 |
| A29 | 1.2 | 30 | 12 | 2 |
| A30 | 1.2 | 30 | 18 | 3 |

Figures 6A, 6B, 6C:
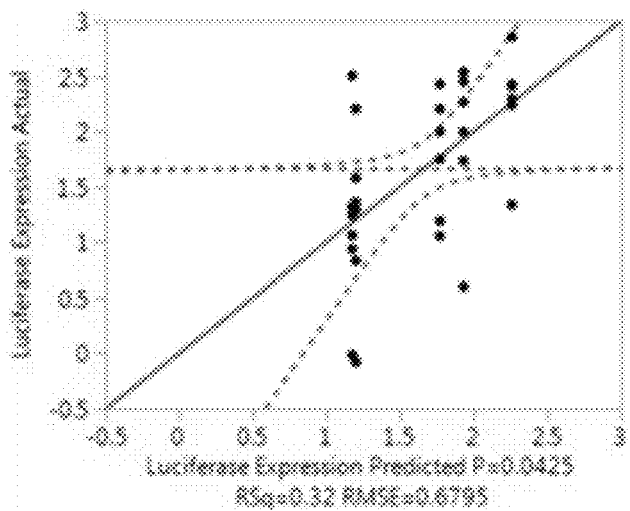
FIGS. 6A-6D. Model results before (FIG. 6A) and after (FIG. 6B) non-significant effects were removed. Note that the 122 end cap is not included because all of the parameter estimates of the discrete attributes under the "end cap" variable will sum to 0 (that is, only 4/5 attributes within the "end cap" variable are independent). The ultimate model prediction versus the actual results is shown in (FIG. 6C), with its residuals given in (FIG. 6D).
Figures 6D, 7A, 7B:
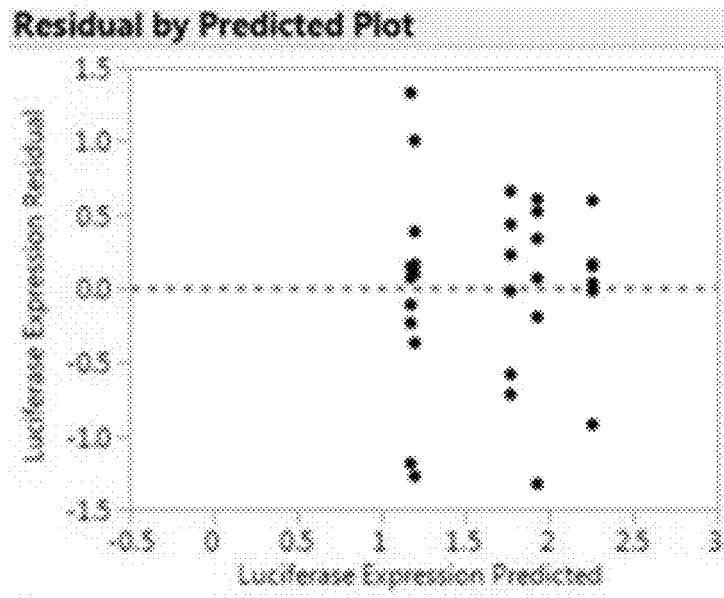
FIGS. 7A-7D. Definitive screen model results before (FIG. 7A) and after (FIG. 7B) non-significant effects were removed. The ultimate model prediction versus the actual results is shown in (FIG. 7C), with its residuals given in (FIG. 7D).
Figure 7C:
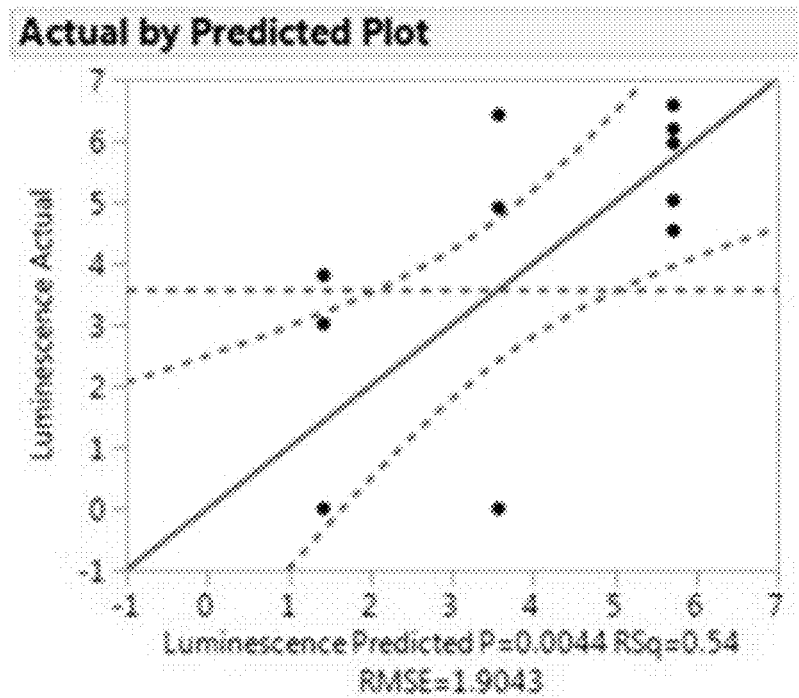
Figure 7D:
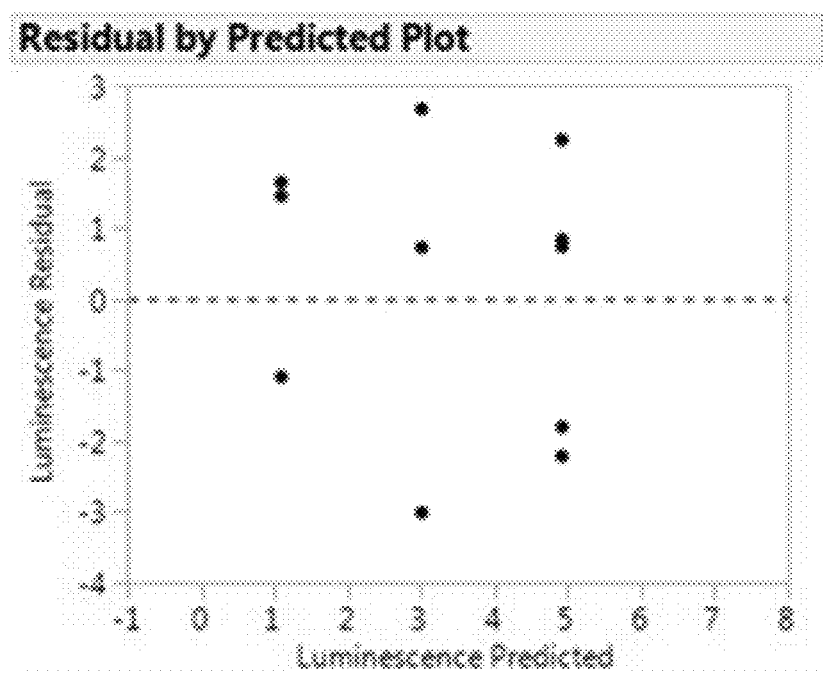
Figures 8A, 8B, 8C:
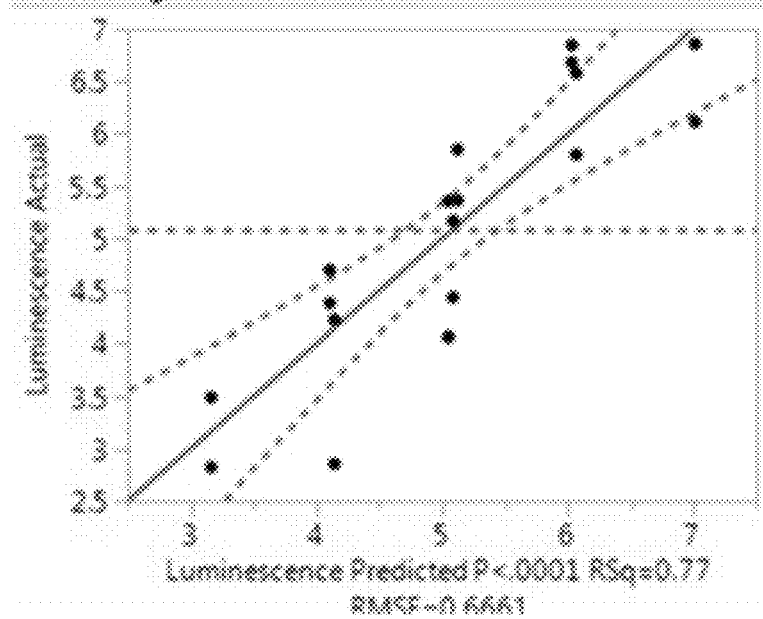
FIGS. 8A-8D. Partial factorial formulation screen lung efficacy model results before (FIG. 8A) and after (FIG. 8B) non-significant effects were removed. The ultimate model prediction versus the actual results is shown in (FIG. 8C), with its residuals given in (FIG. 8D).
Figures 8D, 9A:
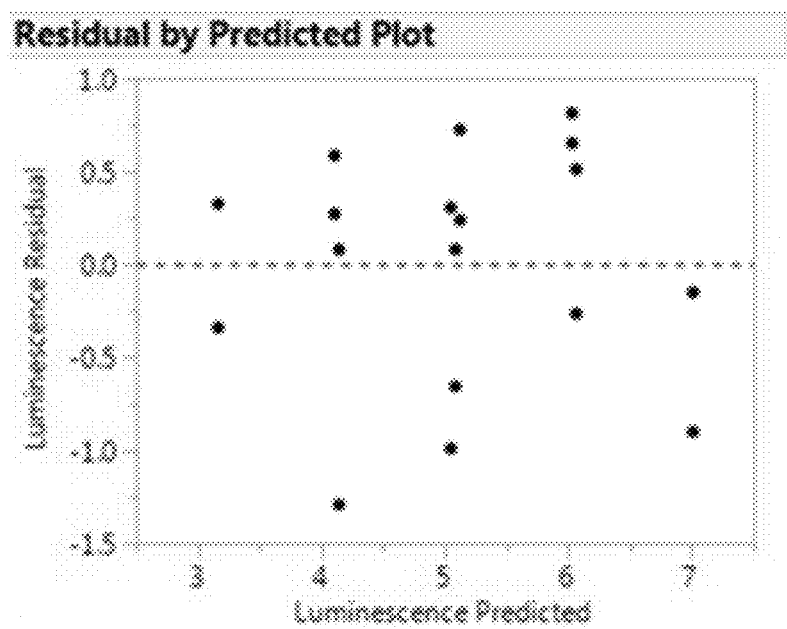
FIGS. 9A-9D. Partial factorial formulation screen spleen efficacy model results before (FIG. 9A) and after (FIG. 9B) non-significant effects were removed. The ultimate model prediction versus the actual results is shown in (FIG. 9C), with its residuals given in (FIG. 9D).
Figures 9B, 9C:
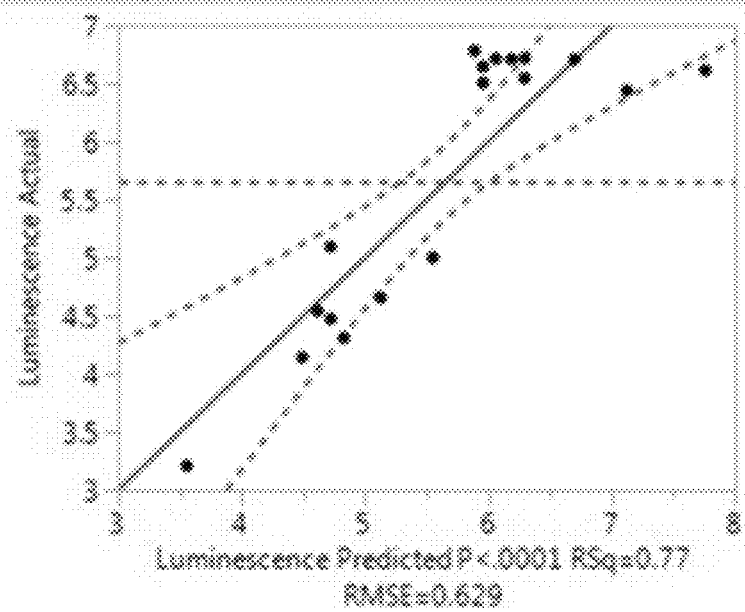
Figures 9D, 10A:
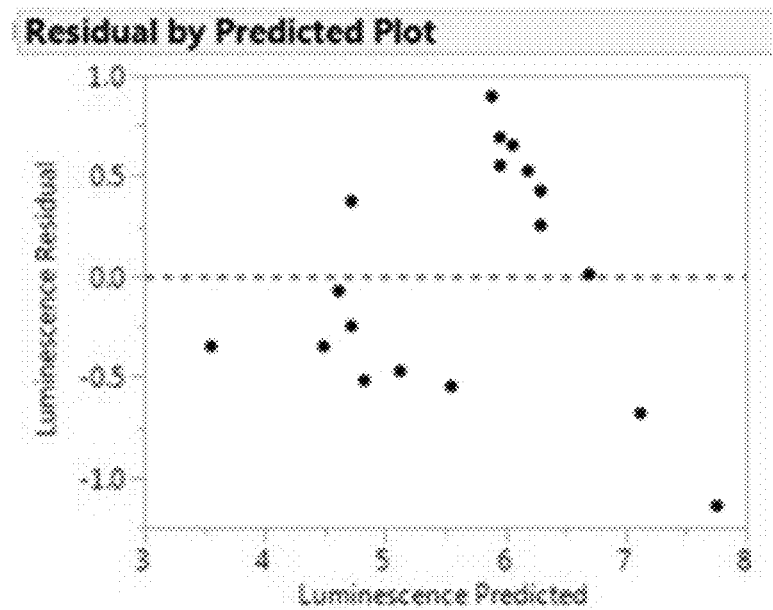
FIGS. 10A-10D. Partial factorial formulation screen nanoparticle diameter model results before (FIG. 10A) and after (FIG. 10B) non-significant effects were removed. The ultimate model prediction versus the actual results is shown in (FIG. 10C), with its residuals given in (FIG. 10D).
Figures 10B, 10C:
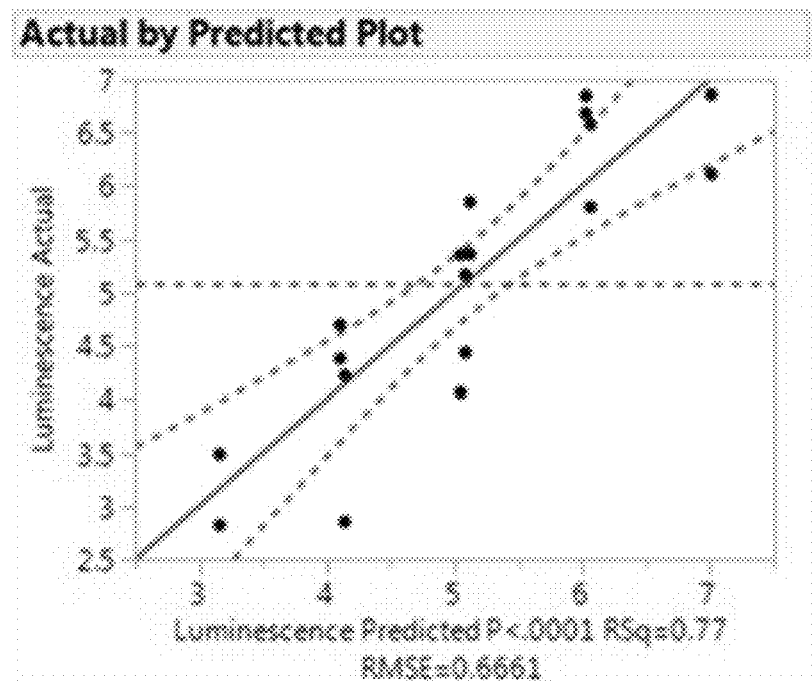
Figure 10D:
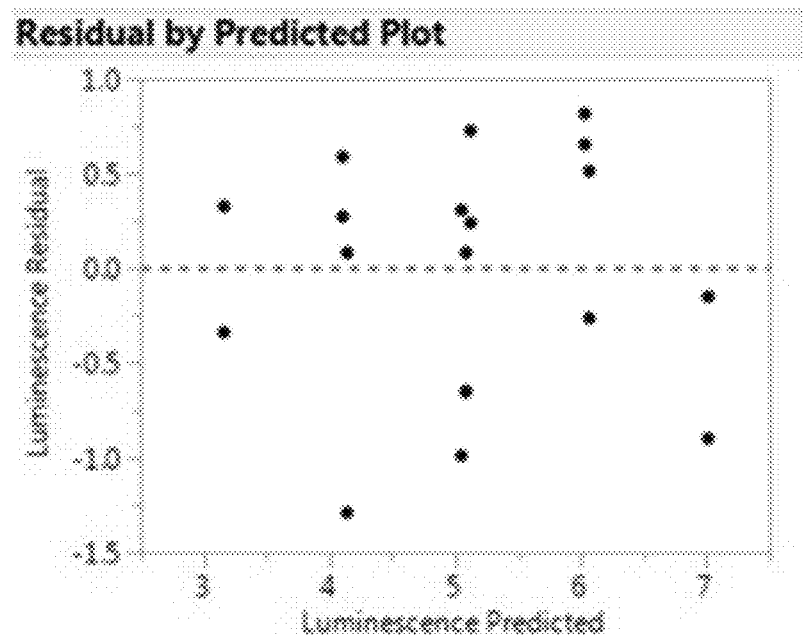

FIG. 6A displays the parameter estimates (i.e. the probability a parameter has a significant effect) for the statistical model (based on a linear least squares regression) before eliminating insignificant variables and FIG. 6B displays the same table after elimination of insignificant variables. As can be seen, only the end capping variable, specifically only the 103 monomer, remained, meaning it is the only variable that exhibited a statistically significant effect on the model. As stated in the text, since previous large-scale end capping screens already identified the 5 end caps used herein as the most potent for PBAE nucleic acid delivery, further optimization was not deemed necessary.

Importantly, a distinction must be made between variables which are statistically significant as main variables to the model and variables which exhibit an observable effect on the system. Clearly, the end cap was not the only variable to affect particle efficacy, as not all polymers end capped with a given monomer had the same efficacy. The other variables simply were not statistically significant in and of themselves, meaning: 1) The variables were only significant at a higher order, which cannot accurately be estimated by a model designed to screen for main effects, or, perhaps less likely, 2) The effect of the variable exhibited no definitive unidirectional trend, which is possible for levels >2.

Definitive Formulation Screen

A definitive screen was chosen for the first formulation screen in an attempt to narrow the large design space that came with limited research into hydrophobic formulations with PBAE terpolymer nanoparticles. Table 3 displays the variable ranges chosen, based off of values commonly used for lipid nanoparticles.[4] Model analysis, as done previously, revealed that DOPE mol % was the only statistically significant variable (FIGS. 7A-7D). This, and the formulation parameters for the D2 formulation which outperformed the original, was taken into account in designing the next screen.

TABLE 3

Parameter ranges for synthesis screens.

| Parameter | Definitive Screen Range | Partial Factorial Screen Range | PEG-lipid Screen Range | "L3" Formulation |
|---|---|---|---|---|
| N/P | 25-100 | 50-75 | X | 50 |
| PEG-lipid mol % | 1-10 | 2-9 | 1-7 | 5 |
| PEG-lipid PEG MW | 1000-5000 | 1000-3000 | X | 2000 |
| PEG-lipid C length | 12-18 | X | X | 18 |
| DOPE mol % | 0-20 | 20-50 | X | 20 |
| Cholesterol mol % | 0-50 | X | X | 0 |

TABLE 4

Conditions for definitive formulation screen.

| Formulation ID | N/P | PEG-lipid C Length | PEG-lipid PEG MW | PEG-lipid mol % | Cholesterol mol % | DOPE mol % |
|---|---|---|---|---|---|---|
| D1 | 62.5 | 14 | 1000 | 1 | 0 | 0 |
| D2 | 100 | 18 | 1000 | 5.5 | 0 | 20 |
| D3 | 100 | 14 | 5000 | 10 | 0 | 10 |
| D4 | 25 | 14 | 1000 | 10 | 25 | 20 |
| D5 | 25 | 16 | 5000 | 1 | 0 | 20 |
| D6 | 100 | 18 | 5000 | 1 | 25 | 0 |
| D7 | 25 | 14 | 5000 | 5.5 | 50 | 0 |
| D8 | 62.5 | 16 | 3000 | 5.5 | 25 | 10 |
| D9 | 62.5 | 18 | 5000 | 10 | 50 | 20 |
| D10 | 100 | 16 | 1000 | 10 | 50 | 0 |
| D11 | 25 | 18 | 3000 | 10 | 0 | 0 |
| D12 | 25 | 18 | 1000 | 1 | 50 | 10 |
| D13 | 100 | 14 | 3000 | 1 | 50 | 20 |

Partial Factorial Formulation Screen

As with the synthesis screen, the interest was in identifying key main effects from remaining variables using a partial factorial screen. The parameter space (Table 5) was shifted from the definitive screen according to the following logic:

- Cholesterol was eliminated as it had by far the least influence on the definitive screen model, and the $D_2$ formulation had no cholesterol (FIG. 7A).
- DOPE mol % had its lowest value adjusted to 20 mol % since it demonstrated a significant positive effect on efficacy in the previous model.
- PEG-lipid mol % had its range decreased to center on the D2 formulation value of 5.5 mol %.
- N/P range was moved upward to account for the N/P of 100 in the D2 formulation, but was lowered from the max of 100 due to concerns regarding particle toxicity and stability.
- PEG-lipid PEG MW range was adjusted closer to the value in the D2 formulation; the range was not centered on D2 as pilot studies revealed issues with particle stability with PEG MWs less than 1000.
- PEG-lipid lipid length was eliminated in order to limit the variable number (and therefore maximize the information available from a given number of runs); this variable was chosen because 2 other PEG-lipid variables were already included. PEG-lipids with 18-carbon tails were chosen for subsequent screens based on the D2 formulation.

Table 5 shows the formulations generated using the JMP software to develop a partial factorial screen consisting of 18 conditions.

TABLE 5

Conditions for partial factorial formulation screen.

| Formulation ID | N/P | PEG-lipid MW | PEG-lipid mol % | DOPE mol % |
|---|---|---|---|---|
| P1 | 50 | 2000 | 9 | 35 |
| P2 | 75 | 1000 | 9 | 50 |
| P3 | 75 | 1000 | 5.5 | 35 |
| P4 | 75 | 3000 | 9 | 20 |
| P5 | 75 | 2000 | 2 | 50 |
| P6 | 50 | 1000 | 2 | 20 |
| P7 | 50 | 1000 | 5.5 | 50 |
| P8 | 50 | 3000 | 2 | 20 |
| P9 | 62.5 | 1000 | 9 | 20 |
| P10 | 75 | 2000 | 5.5 | 20 |
| P11 | 50 | 2000 | 9 | 35 |
| P12 | 62.5 | 3000 | 9 | 50 |
| P13 | 62.5 | 2000 | 2 | 50 |
| P14 | 62.5 | 2000 | 5.5 | 20 |
| P15 | 50 | 3000 | 5.5 | 50 |
| P16 | 75 | 3000 | 2 | 35 |
| P17 | 62.5 | 1000 | 2 | 35 |
| P18 | 62.5 | 3000 | 5.5 | 35 |

Given the lack of lung specificity of these formulations (FIG. 3), two separate models for this screen were built: one for lung efficacy (FIG. 8A-8D) and one for spleen efficacy (FIGS. 9A-9D). As can be seen, both have a strong negative correlation with PEG-lipid mol %. This also prompted an investigation into the particle diameter. Thus, a third model was built, using particle diameter as the dependent variable of interest (FIGS. 10A-10D).

Figure 11:
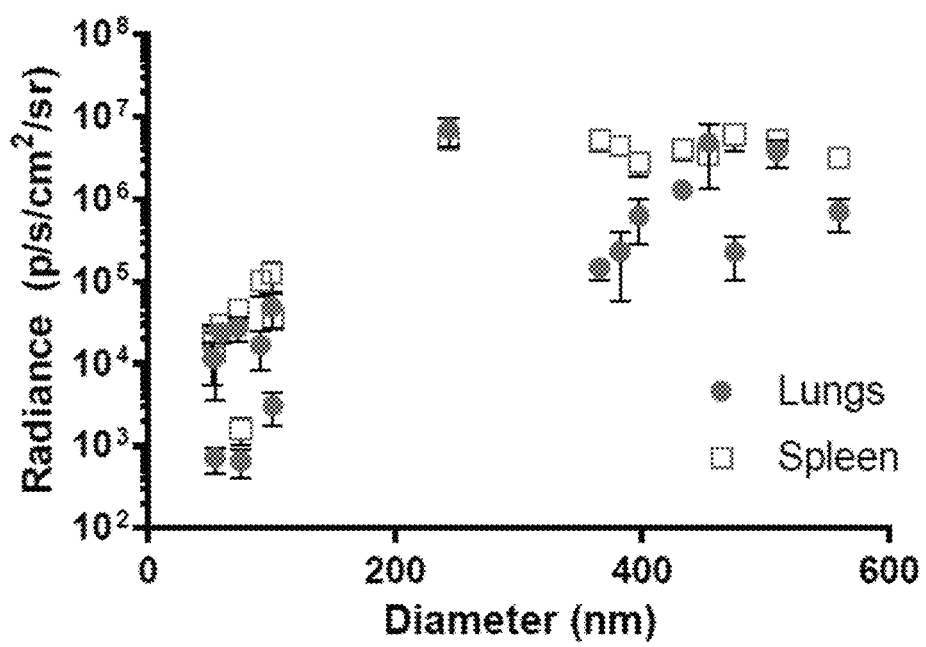
FIG. 11. Correlation between diameter and luciferase signal for the partial factorial formulation screen. The two clusters of diameter, <100 nm and >300 nm, correspond with low efficacy and consistently high spleen efficacy, respectively (n=3).

PEG-lipid mol % had a significant effect on particle diameter, just as it did on spleen and lung efficacy. Therefore any correlation between particle size and efficacy was investigated, both in the lungs and spleen. As can be seen in FIG. 11, the diameters clustered into a "large" (>300 nm diameter) and "small" (<100 nm diameter) region, which corresponded with consistent spleen efficacy and low overall efficacy, respectively. Thus, particles within the "middle" region with respect to diameter may result in greater lung specificity.

PEG-Lipid Screen

Figure 12:
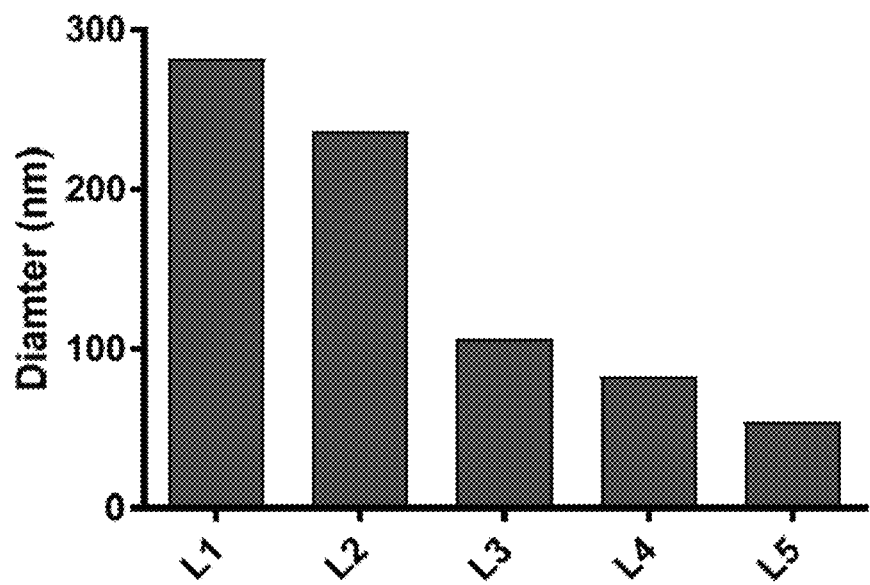
FIG. 12. Diameters of particles from the PEG-lipid screen.

For this final screen, the goal was to vary the PEG-lipid content of the nanoparticles in order to obtain particles within the range of interest. As for setting the other parameters varied in the previous screen, the logic was as follows:

- N/P was not a significant variable in either the lungs or the spleen, and was therefore set to the bottom of the tested range (50) to minimize toxicity
- PEG MW was set to 2000, as the only formulation within the ~100-~300 nm range from the previous screen, P14, had a PEG MW of 2000
- DOPE mol % was set to 20; the definitive screen showed a strong positive correlation between DOPE mol % and efficacy (0-20), while the partial factorial screen (0-50 mol %) showed a strong negative correlation between the two, suggesting 20 mol % to be the near optimum Table 6 shows the conditions used for this screen, based on PEG-lipid amounts that yielded particle diameters within the range of interest (FIG. 12). As shown in FIGS. 3A-3D, these particles were more lung specific, and both the specificity and efficacy were dependent on PEG-lipid incorporation.

TABLE 6

Conditions for the PEG-lipid screen.

| Formulation ID | PEG-lipid mol % |
|---|---|
| L1 | 1 |
| L2 | 1.5 |
| L3 | 5 |
| L4 | 6 |
| L5 | 7 |

TABLE 7

Antibodies used in FACS analysis

| Antigen | Color | Dilution | Supplier | Clone |
|---|---|---|---|---|
| CD31 | AF488 | 1:300 | BioLegend | MEC13.3 |
| CD45 | BV421 | 1:300 | BioLegend | 104 |
| CD45.2 (Immune Subtype Study) | BUV737 | 1:100 | Becton Dickinson | 104 |
| TCR-β | BV421 | 1:200 | BioLegend | H57-597 |
| Ly6G | BV510 | 1:400 | BioLegend | 1A8 |
| Siglec F | BV605 | 1:200 | Becton Dickinson | E50-2440 |
| Ly6C | AF488 | 1:400 | Becton Dickinson | HK1.4 |
| CD11c | PerCP/Cy5.5 | 1:250 | BioLegend | N418 |
| F4/80 | PE/Cy7 | 1:250 | BioLegend | BM8 |
| CD19 | APC | 1:300 | BioLegend | 6D5 |
| CD11b | AF700 | 1:400 | BioLegend | M1/70 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

REFERENCES

1. J. C. Kaczmarek, P. S. Kowalski, D. G. Anderson, Genome Med. 2017, 9, 60.
2. A. Yamamoto, M. Kormann, J. Rosenecker, C. Rudolph, Eur. J. Pharm. Biopharm. 2009, 71, 484.
3. S. F. Dowdy, Nat. Biotechnol. 2017, 35, 222.
4. K. J. Kauffman, M. J. Webber, D. G. Anderson, J. Control. Release 2016, 240, 227.
5. S. Guan, J. Rosenecker, Gene Ther. 2017, 24, 133.
6. N. Pardi, A. J. Secreto, X. Shan, F. Debonera, J. Glover, Y. Yi, H. Muramatsu, H. Ni, B. L. Mui, Y. K. Tam, F. Shaheen, R. G. Collman, K. Karikó, G. A. Danet-Desnoyers, T. D. Madden, M. J. Hope, D. Weissman, Nat. Commun. 2017, 8, 14630.
7. C. R. Stadler, H. Bähr-Mahmud, L. Celik, B. Hebich, A. S. Roth, R. P. Roth, K. Karikó, Ö. Türeci, U. Sahin, Nat. Med. 2017, 3.
8. X. Su, J. Fricke, D. G. Kavanagh, D. J. Irvine, Mol. Pharm. 2011, 8, 774.
9. J. S. Chahal, O. F. Khan, C. L. Cooper, J. S. McPartlan, J. K. Tsosie, L. D. Tilley, S. M. Sidik, S. Lourido, R. Langer, S. Bavari, H. L. Ploegh, D. G. Anderson, Proc. Natl. Acad. Sci. 2016, 113, E4133.
10. E. Schrom, M. Huber, M. Aneja, C. Dohmen, D. Emrich, J. Geiger, G. Hasenpusch, A. Herrmann-Janson, V. Kretzschmann, O. Mykhailyk, P. Pasewald, P. Oak, A. Hilgendorff, D. Wohlleber, H.-G. Hoymann, D. Schaudien, C. Plank, C. Rudolph, R. Kubisch-Dohmen, Mol. Ther.—Nucleic Acids 2017, 7, 350.
11. F. DeRosa, B. Guild, S. Karve, L. Smith, K. Love, J. R. Dorkin, K. J. Kauffman, J. Zhang, B. Yahalom, D. G. Anderson, M. W. Heartlein, Gene Ther. 2016, 23, 699.
12. A. J. Mahiny, A. Dewerth, L. E. Mays, M. Alkhaled, B. Mothes, E. Malaeksefat, B. Loretz, J. Rottenberger, D. M. Brosch, P. Reautschnig, P. Surapolchai, F. Zeyer, A. Schams, M. Carevic, M. Bakele, M. Griese, M. Schwab, B. Nurnberg, S. Beer-Hammer, R. Handgretinger, D. Hartl, C.-M. Lehr, M. S. D. Kormann, Nat. Biotechnol. 2015, 33, 584.
13. H. Yin, C.-Q. Song, J. R. Dorkin, L. J. Zhu, Y. Li, Q. Wu, A. Park, J. Yang, S. Suresh, A. Bizhanova, A. Gupta, M. F. Bolukbasi, S. Walsh, R. L. Bogorad, G. Gao, Z. Weng, Y. Dong, V. Koteliansky, S. A. Wolfe, R. Langer, W. Xue, D. G. Anderson, Nat. Biotechnol. 2016, 34, 328.
14. J. B. Miller, S. Zhang, P. Kos, H. Xiong, K. Zhou, S. S. Perelman, H. Zhu, D. J. Siegwart, Angew. Chemie Int. Ed. 2017, 56, 1059.
15. R. Kanasty, J. R. Dorkin, A. Vegas, D. Anderson, Nat. Mater. 2013, 12, 967.
16. O. S. Fenton, K. J. Kauffman, R. L. McClellan, E. A. Appel, J. R. Dorkin, M. W. Tibbitt, M. W. Heartlein, F. DeRosa, R. Langer, D. G. Anderson, Adv. Mater. 2016, 28, 2939.
17. K. J. Kauffman, J. R. Dorkin, J. H. Yang, M. W. Heartlein, F. DeRosa, F. F. Mir, O. S. Fenton, D. G. Anderson, Nano Lett. 2015, 15, 7300.
18. C. E. Green, A. M. Turner, Respir. Res. 2017, 18, 20.
19. N. G. J. Leus, H. W. M. Morselt, P. J. Zwiers, P. S. Kowalski, M. H. J. Ruiters, G. Molema, J. A. A. M. Kamps, Int. J. Pharm. 2014, 469, 121.
20. R. Bals, P. S. Hiemstra, Eur. Respir. J. 2004, 23, 327.
21. U. Griesenbach, E. W. F. W. Alton, Hum. Mol. Genet. 2013, 22, R52.
22. E. Y. Kim, J. T. Battaile, A. C. Patel, Y. You, E. Agapov, H. Grayson, L. A. Benoit, D. E. Byers, Y. Alevy, J. Tucker, R. Tidwell, J. W. Tyner, J. D. Morton, M. Castro, G. A. Patterson, R. A. Schwendener, J. D. Allard, G. Peltz, M. J. Holtzman, Nat. Med. 2008, 14, 633.
23. S. Grumelli, D. B. Corry, L. Song, L. Song, L. Green, J. Huh, J. Hacken, R. Espada, R. Bag, D. E. Lewis, F. Kheradmand, PLoS Med. 2004, 1, e8.

24. J. C. Kaczmarek, A. K. Patel, K. J. Kauffman, O. S. Fenton, M. J. Webber, M. W. Heartlein, F. DeRosa, D. G. Anderson, Angew. Chemie Int. Ed. 2016, 55, 13808.
25. D. M. Lynn, R. Langer, J. Am. Chem. Soc. 2000, 122, 10761.
26. A. a. Eltoukhy, D. Chen, C. a. Alabi, R. Langer, D. G. Anderson, Adv. Mater. 2013, 25, 1487.
27. D. G. Anderson, D. M. Lynn, R. Langer, Angew. Chemie Int. Ed. 2003, 42, 3153.
28. R. B. Shmueli, J. C. Sunshine, Z. Xu, E. J. Duh, J. J. Green, Nanomedicine Nanotechnology, Biol. Med. 2012, 8, 1200.
29. G. T. Zugates, W. Peng, A. Zumbuehl, S. Jhunjhunwala, Y.-H. Huang, R. Langer, J. a Sawicki, D. G. Anderson, Mol. Ther. 2007, 15, 1306.
30. A. a. Eltoukhy, D. J. Siegwart, C. a. Alabi, J. S. Rajan, R. Langer, D. G. Anderson, Biomaterials 2012, 33, 3594.
31. G. Odian, Principles of Polymerization, John Wiley & Sons, Inc., Hoboken, N.J., 2004.
32. J. C. Kaczmarek, A. K. Patel, K. J. Kauffman, O. S. Fenton, M. J. Webber, M. W. Heartlein, F. DeRosa, D. G. Anderson, Angew. Chem. Int. Ed. Engl. 2016, 1.
33. B. Jones, C. J. Nachtsheim, J. Qual. Technol. 2011, 43, 1.
34. D. Chen, K. T. Love, Y. Chen, A. A. Eltoukhy, C. Kastrup, G. Sahay, A. Jeon, Y. Dong, K. A. Whitehead, D. G. Anderson, J. Am. Chem. Soc. 2012, 134, 6948.
35. E. Blanco, H. Shen, M. Ferrari, Nat. Biotechnol. 2015, 33, 941.
36. Y. Dong, K. T. Love, J. R. Dorkin, S. Sirirungruang, Y. Zhang, D. Chen, R. L. Bogorad, H. Yin, A. J. Vegas, C. A. Alabi, G. Sahay, K. T. Olejnik, W. Wang, A. Schroeder, A. K. R. Lytton-Jean, D. J. Siegwart, A. Akinc, C. Barnes, S. A. Barros, M. Carioto, K. Fitzgerald, J. Hettinger, V. Kumar, T. I. Novobrantseva, J. Qin, V. Koteliansky, R. Langer, D. G. Anderson, Proc. Natl. Acad. Sci. 2014, 111, 5753.
37. K. a Whitehead, J. Matthews, P. H. Chang, F. Niroui, J. R. Dorkin, M. Severgnini, D. G. Anderson, ACS Nano 2012, 6, 6922.
38. K. J. Kauffman, M. A. Oberli, J. R. Dorkin, J. E. Hurtado, J. C. Kaczmarek, S. Bhadini, J. Wyckoff, R. Langer, A. Jaklenec, D. G. Anderson, Mol. Ther.—Nucleic Acids 2017, 10, 55.
39. A. Bantikassegn, X. Song, K. Politi, Am. J. Respir. Cell Mol. Biol. 2015, 52, 409.
40. G. R. Fulmer, A. J. M. Miller, N. H. Sherden, H. E. Gottlieb, A. Nudelman, B. M. Stoltz, J. E. Bercaw, K. I. Goldberg, Organometallics 2010, 29, 2176.
41. D. Chen, K. T. Love, Y. Chen, A. A. Eltoukhy, C. Kastrup, G. Sahay, A. Jeon, Y. Dong, K. A. Whitehead, D. G. Anderson, J. Am. Chem. Soc. 2012, 134, 6948.
42. J. B. Clark, A. M. Dean, Stat. Sin. 2001, 11, 537.
43. K. J. Kauffman, J. R. Dorkin, J. H. Yang, M. W. Heartlein, F. DeRosa, F. F. Mir, O. S. Fenton, D. G. Anderson, Nano Lett. 2015, 15, 7300.
44. J. C. Kaczmarek, A. K. Patel, K. J. Kauffman, 0. S. Fenton, M. J. Webber, M. W. Heartlein, F. DeRosa, D. G. Anderson, Angew. Chemie Int. Ed. 2016, 55, 13808.
45. Y. Dong, K. T. Love, J. R. Dorkin, S. Sirirungruang, Y. Zhang, D. Chen, R. L. Bogorad, H. Yin, A. J. Vegas, C. A. Alabi, G. Sahay, K. T. Olejnik, W. Wang, A. Schroeder, A. K. R. Lytton-Jean, D. J. Siegwart, A. Akinc, C. Barnes, S. A. Barros, M. Carioto, K. Fitzgerald, J. Hettinger, V. Kumar, T. I. Novobrantseva, J. Qin, V. Koteliansky, R. Langer, D. G. Anderson, Proc. Natl. Acad. Sci. 2014, 111, 5753.

The invention claimed is:

1. A composition comprising a polymer of Formula (I):

or a pharmaceutically acceptable salt thereof, wherein:

each A independently is $A_1$ or $A_2$;

$A_1$ is

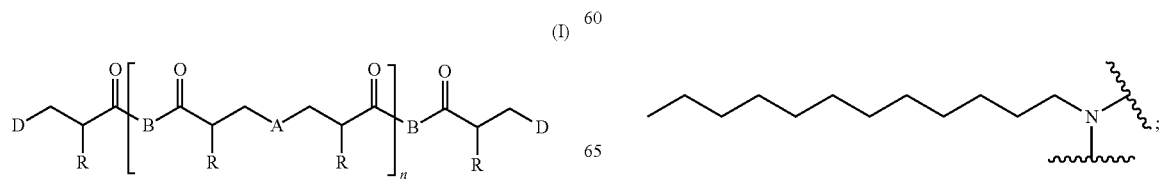

A₂ is

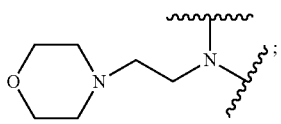 [SMILES: *N(*)CCN1CCOCC1]

B is

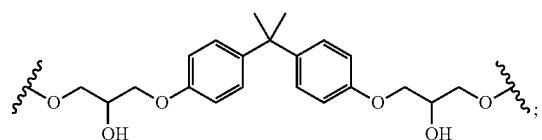 [SMILES: *OCC(O)COc1ccc(C(C)(C)c2ccc(OCC(O)CO*)cc2)cc1]

and

D is selected from:

(1) 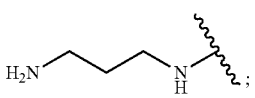

(2) 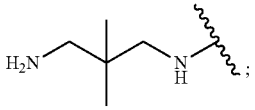

(3) 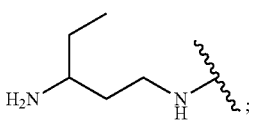

(4) 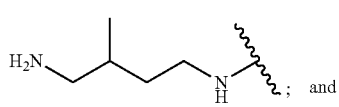

(5) 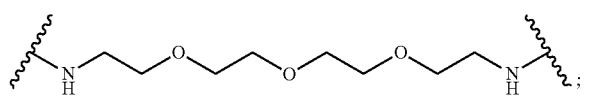

each R independently is hydrogen or optionally substituted aliphatic; and
n is 1-10000;

wherein the composition further comprises:
- a PEG lipid in an amount of 1-10 mol % with reference to the polymer;
- a phospholipid in an amount of up to 20 mol % with reference to the polymer; and
- a polynucleotide.

2. The composition of claim 1, wherein the PEG portion of the PEG lipid has an average molecular weight in the range of 1000-5000 Da.

3. The composition of claim 1, wherein the PEG lipid is present in the amount of 1-5 mol % with reference to the polymer.

4. The composition of claim 1, wherein the composition further comprises a steroid.

5. The composition of claim 4, wherein the steroid is present in the amount of 1-50 mol % with reference to the polymer.

6. The composition of claim 1, wherein the phospholipid is present in the amount of about 20 mol % with reference to the polymer.

7. The composition of claim 1, wherein the composition is characterized as having an N/P ratio of 25-100.

8. The composition of claim 1, wherein the composition is a pharmaceutical composition.

9. A method of delivering a polynucleotide to a cell, comprising exposing the cell to a composition of claim 1.

10. A method of treating a disease, disorder, or condition from which a subject suffers, comprising administering to the subject in need thereof an effective amount of a composition of claim 1.

11. The composition of claim 7, wherein the composition is characterized as having an N/P ratio of 50-100.

12. The composition of claim 1, wherein the polynucleotide is DNA.

13. The composition of claim 1, wherein the polynucleotide is RNA.

14. The composition of claim 13, wherein the RNA is dsRNA, siRNA, shRNA, miRNA, mRNA, or antisense RNA.

15. The composition of claim 1, wherein the polynucleotide encodes a protein or peptide.

16. The composition of claim 15, wherein the protein is an antigen.

17. The composition of claim 1, wherein D is

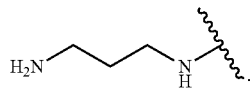

18. The composition of claim 1, wherein the composition is in the form of a particle.

19. The composition of claim 18, wherein the particle is a nanoparticle.

20. The composition of claim 8, wherein the pharmaceutical composition is formulated for intravenous administration.

21. The composition of claim 1, wherein the PEG lipid is C18-PEG2000.

22. The composition of claim 4, wherein the steroid is cholesterol.

23. The composition of claim 1, wherein the phospholipid is selected from distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 1-stearoyl-2-oleoyl-phosphatidyethanolamine (SOPE), phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, and palmitoyloleoylphosphatidylglycerol (POPG).

24. The composition of claim 23, wherein the phospholipid is DOPE.

25. The composition of claim 13, wherein the polynucleotide is mRNA.

26. The composition of claim 1, wherein the polynucleotide is chemically modified.

27. The method of claim 9, wherein the polynucleotide is DNA.

28. The method of claim 9, wherein the polynucleotide is RNA.

29. The method of claim 28, wherein the RNA is dsRNA, siRNA, shRNA, miRNA, mRNA, or antisense RNA.

30. The method of claim 9, wherein the polynucleotide is mRNA.

31. The method of claim 9, wherein the polynucleotide is chemically modified.

32. The method of claim 9, wherein the polynucleotide encodes a protein or peptide.

33. The method of claim 32, wherein the protein is an antigen.

34. The method of claim 10, wherein the disease, disorder, or condition is selected from the group consisting of proliferative disorders, inflammatory disorders, autoimmune disorders, painful conditions, and diseases of the lung, spleen, and liver.

\* \* \* \* \*